(12) United States Patent
Chu et al.

(10) Patent No.: US 9,441,217 B2
(45) Date of Patent: Sep. 13, 2016

(54) PLASTIDIAL NUCLEOTIDE SUGAR EPIMERASES

(75) Inventors: Chengcai Chu, Bejing (CN); Chunlai Li, Bejing (CN)

(73) Assignee: INSTITUTE OF GENETICS AND DEVELOPMENTAL BIOLOGY, Bejing (CN)

( * ) Notice: Subject to any disclaimer, the term of this patent is extended or adjusted under 35 U.S.C. 154(b) by 541 days.

(21) Appl. No.: 13/698,370

(22) PCT Filed: May 16, 2011

(86) PCT No.: PCT/CN2011/000852
§ 371 (c)(1),
(2), (4) Date: Jul. 11, 2013

(87) PCT Pub. No.: WO2011/143933
PCT Pub. Date: Nov. 24, 2011

(65) Prior Publication Data
US 2014/0059715 A1    Feb. 27, 2014

(30) Foreign Application Priority Data
May 17, 2010 (CN) .......................... 2010 1 0178405

(51) Int. Cl.
C12N 15/82       (2006.01)
C12N 9/90        (2006.01)

(52) U.S. Cl.
CPC ............. *C12N 9/90* (2013.01); *C12N 15/8261* (2013.01); *C12N 15/8273* (2013.01)

(58) Field of Classification Search
None
See application file for complete search history.

(56) References Cited

U.S. PATENT DOCUMENTS 6,992,236 B1 *   1/2006   Famodu et al. ............... 800/295
2006/0123505 A1 * 6/2006   Kikuchi et al. ............... 800/278

FOREIGN PATENT DOCUMENTS

CN    101117638 A        2/2008
CN    101117638 A *      2/2008
WO    2009003977 A2      1/2009

OTHER PUBLICATIONS

Fourgoux-Nicol et al, 1999, Plant Molecular Biology 40 :857-872.*
Higgins et al, 1992, Cabios, 8:189-191.*
Dörmann et al, 1996, Archives of Biochem. & Biophys., 327:27-34.*
Genbank Accession No. NM_001049575; Feb. 14, 2008.
Dormann, et al.; "Functional expression of uridine 5'-diphospho-glucose-4-epimerase (EC 5.1.3.2) from Arabidopsis thaliana in *Saccharomyces cerevisiae* and *Escherichia coli*"; Arhieves of Biochemistry and Biophysics (1996) 327:27-34.
International Search Report—PCT/CN2011/000852.

* cited by examiner

*Primary Examiner* — Jason Deveau Rosen
(74) *Attorney, Agent, or Firm* — Ballard Spahr LLP

(57) ABSTRACT

Isolated polynucleotides and polypeptides and recombinant DNA constructs of plastidial sugar epimerases useful for conferring improved agronomic performance including yield and drought are disclosed. Compositions (such as plants or seeds) having these recombinant DNA constructs, and methods utilizing these recombinant DNA constructs are also disclosed.

12 Claims, 11 Drawing Sheets

FIG. 11

SEQUENCE LISTING

```
<160> NUMBER OF SEQ ID NOS: 76

<210> SEQ ID NO 1
<211> LENGTH: 340
<212> TYPE: PRT
<213> ORGANISM: Oryza sativa

<400> SEQUENCE: 1

Met Gly Gly Ala Ala Val Ser Ser Leu Leu Ala Thr Pro Thr Pro Thr
1               5                   10                  15

Ser Arg Pro Arg Pro Val Ser Thr Thr Thr Ala Pro Phe Ser Val Asn
            20                  25                  30

Leu Ser Thr Ala Ala Ala Arg Ala Pro Arg Leu Leu Leu Leu Ser Arg
        35                  40                  45

Arg Pro Arg Pro Arg Pro Ala Ala Ala Val Leu Gly Val Ser Asp Asp
    50                  55                  60

Thr Gly Val Lys Met Ala Gly Ser Asp Ile Val Gly Lys Asn Asp Leu
65                  70                  75                  80
```

```
Leu Ile Val Gly Pro Gly Val Leu Gly Arg Leu Val Ala Glu Lys Trp
                85                  90                  95

Gln Glu Glu His Pro Gly Cys Lys Val Phe Gly Gln Thr Ala Ser Thr
            100                 105                 110

Asp His His Asn Glu Leu Ser Asn Ile Gly Ile Ile Pro Ser Leu Lys
        115                 120                 125

Gly Ser Thr Phe Pro Gln Lys Val Pro Tyr Val Ile Phe Cys Ala Pro
    130                 135                 140

Pro Ser Arg Ser Asp Asp Tyr Pro Gly Asp Val Arg Val Ala Ala Ser
145                 150                 155                 160

Asn Trp Thr Gly Glu Gly Ser Phe Val Phe Thr Ser Thr Ala Leu
                165                 170                 175

Tyr Asp Cys Ser Asp Asn Glu Leu Cys Asn Glu Asp Cys Pro Ser Val
            180                 185                 190

Pro Ile Gly Arg Ser Pro Arg Thr Asp Val Leu Leu Lys Ala Glu Asn
        195                 200                 205

Val Val Leu Glu Ala Gly Gly Cys Val Leu Arg Leu Ala Gly Leu Tyr
    210                 215                 220

Lys Ile Asp Arg Gly Ala His Phe Phe Trp Leu Arg Lys Gly Thr Leu
225                 230                 235                 240

Asp Thr Arg Pro Asp His Ile Ile Asn Gln Ile His Tyr Glu Asp Ala
                245                 250                 255

Ala Ser Leu Ala Ile Ala Ile Met Lys Lys Gly His Arg Gly Arg Ile
            260                 265                 270

Phe Leu Gly Cys Asp Asn Lys Pro Leu Ser Arg Gln Glu Ile Met Asp
        275                 280                 285

Ser Val Asn Arg Ser Gly Lys Phe Asp Thr Lys Phe Gln Gly Phe Thr
    290                 295                 300

Gly Thr Asp Gly Pro Leu Gly Lys Lys Met Glu Asn Ser Arg Thr Arg
305                 310                 315                 320

Ser Glu Ile Gly Trp Glu Pro Lys Tyr Pro Ser Phe Thr Glu Phe Leu
                325                 330                 335

Gly Leu Asp Ser
            340

<210> SEQ ID NO 2
<211> LENGTH: 336
<212> TYPE: PRT
<213> ORGANISM: Sorghum bicolor

<400> SEQUENCE: 2

Met Arg Ala Ala Ala Ala Ser Phe His Leu Ala Pro Ala Thr Asn
1               5                   10                  15

Pro Ala His Pro Arg Gly Ser Thr Thr Asp Ser Cys Ser Leu Lys Pro
            20                  25                  30

Ala Pro Thr Ala Gln Pro Pro Arg Leu Arg Ser Leu Ala Arg Arg Ala
        35                  40                  45

Pro Leu Val Cys Ala Ser Leu Gly Ile Ser His Asp Lys Gly Ser Asp
    50                  55                  60

Ile Ser Asp Pro Asn Val Gly Gln Asn Asp Leu Leu Ile Val Gly
65                  70                  75                  80

Pro Gly Val Leu Gly Arg Ile Val Ala Glu Lys Trp Gln Lys Glu His
                85                  90                  95

Pro Gly Cys Lys Val Tyr Gly Gln Thr Ala Ser Lys Asn His His Ser
            100                 105                 110
```

```
            100                 105                 110
Glu Leu Thr Asp Leu Gly Ile Ile Pro Ser Leu Lys Gly Thr Thr Ile
            115                 120                 125
His Gln Lys Val Pro His Val Ile Phe Cys Ala Pro Pro Ser Ser Ser
        130                 135                 140
Asp Asp Tyr Pro Gly Asp Val Arg Leu Ala Ala Ser Asn Trp Ser Gly
145                 150                 155                 160
Glu Gly Ser Phe Leu Phe Thr Ser Ser Thr Ala Leu Tyr Asp Cys Ser
                165                 170                 175
Asp Asn Ser Met Cys Asn Glu Asp Cys Ser Ser Val Pro Ile Gly Arg
            180                 185                 190
Ser Pro Arg Thr Asp Val Leu Leu Lys Val Glu Asn Val Val Leu Glu
        195                 200                 205
Ala Gly Gly Cys Val Leu Arg Leu Ala Gly Leu Tyr Lys Ile Asp Arg
    210                 215                 220
Gly Ala His Val Phe Trp Leu Arg Lys Gly Thr Leu Asp Thr Arg Pro
225                 230                 235                 240
Asp His Ile Ile Asn Gln Ile His Tyr Glu Asp Ala Ala Ser Leu Ala
                245                 250                 255
Val Ala Ile Met Lys Lys Arg Leu Arg Ser Arg Ile Phe Leu Gly Cys
            260                 265                 270
Asp Asn Lys Pro Leu Ser Arg Gln Glu Ile Met Asp Ala Val Asn Lys
        275                 280                 285
Ser Gly Lys Phe Asp Thr Lys Phe Glu Gly Phe Thr Gly Thr Asp Gly
    290                 295                 300
Pro Leu Gly Lys Arg Met Glu Asn Ser Lys Thr Arg Ala Glu Ile Gly
305                 310                 315                 320
Trp Glu Pro Lys Tyr Pro Ser Phe Thr Glu Phe Leu Gly Ile Ser Ser
                325                 330                 335

<210> SEQ ID NO 3
<211> LENGTH: 296
<212> TYPE: PRT
<213> ORGANISM: Sorghum bicolor

<400> SEQUENCE: 3

Met Ser Ala Ala Ala Asp Ser Ser Ser Ser Ser Ile Gly Ile
1               5                   10                  15
Pro Arg Asp Ala Ala Val Ser Ser Leu Ser Pro Glu Ser Val Ser Asn
                20                  25                  30
Asn Asp Leu Leu Ile Val Gly Pro Gly Val Leu Gly Arg Ile Val Ala
            35                  40                  45
Glu Met Trp Lys Gln Glu Tyr Pro Gly Cys Lys Val Cys Gly Gln Thr
    50                  55                  60
Ala Thr Thr Asp His His Ser Glu Leu Thr Asp Ile Gly Ile Ile Pro
65                  70                  75                  80
Ser Leu Lys Arg Ser Val Ala Gly Pro Lys Phe Pro Asn Val Ile Phe
                85                  90                  95
Cys Ala Pro Pro Tyr Arg Ser Glu Asp Tyr Ala Gly Asp Leu Arg Ile
            100                 105                 110
Ala Ala Ser Asn Trp Asn Gly Glu Gly Ser Phe Leu Phe Thr Ser Ser
        115                 120                 125
Thr Ala Val Tyr Asp Cys Ser Asp Asn Gly Phe Cys Gly Glu Asp Ser
    130                 135                 140
```

```
Pro Cys Val Ser Ile Gly Gln Ser Pro Arg Thr Asp Val Leu Leu Lys
145                 150                 155                 160

Ala Glu Asn Val Val Leu Glu Ala Gly Gly Cys Val Leu Arg Leu Ala
                165                 170                 175

Gly Leu Tyr Lys Ser Asp Arg Gly Pro His Val Tyr Trp Leu Ser Lys
            180                 185                 190

Gly Thr Leu Asp Val Arg Pro Asp His Ile Leu Asn Leu Ile His Tyr
        195                 200                 205

Glu Asp Ala Ala Ser Leu Ala Ile Ala Ile Met Lys Lys Arg Leu Arg
    210                 215                 220

Ser Arg Ile Phe Val Gly Cys Asp Asn Glu Pro Leu Ser Arg Leu Glu
225                 230                 235                 240

Ile Met Asp Arg Val Asn Arg Ser Gly Lys Phe Glu Thr Gln Phe Gln
                245                 250                 255

Gly Phe Thr Gly Thr Asp Gly Pro Leu Gly Lys Arg Met Glu Asn Ser
            260                 265                 270

Lys Thr Arg Ala Glu Leu Gly Trp Gln Pro Lys Tyr Pro Ser Phe Thr
        275                 280                 285

Glu Phe Leu Gly Leu Ser Asn Leu
    290                 295

<210> SEQ ID NO 4
<211> LENGTH: 336
<212> TYPE: PRT
<213> ORGANISM: Zea mays

<400> SEQUENCE: 4

Met Arg Ala Ala Ala Ala Ser Phe His Leu Ala Pro Ala Thr Lys
1               5                   10                  15

Pro Ala His Arg Arg Gly Cys Thr Thr Glu Ser Cys Ser Leu Lys Pro
                20                  25                  30

Ala Pro Thr Ala Arg Pro Pro Arg Leu Arg Ser Leu Ala Gly Arg Ala
            35                  40                  45

Pro Leu Val Cys Ala Ser Leu Gly Ile Ser His Asp Lys Gly Phe Asp
    50                  55                  60

Ile Ser Asp Pro Asn Val Val Gly Gln Asn Asp Leu Leu Ile Val Gly
65                  70                  75                  80

Pro Gly Val Leu Gly Arg Ile Ile Ala Glu Lys Trp Lys Lys Glu His
                85                  90                  95

Pro Ser Cys Lys Val Tyr Gly Gln Thr Ala Ser Lys Asn His His Asn
            100                 105                 110

Glu Leu Thr Asp Leu Gly Ile Ile Pro Ser Leu Lys Gly Thr Thr Val
        115                 120                 125

His Gln Lys Val Pro His Val Ile Phe Cys Ala Pro Pro Ser Gly Ser
    130                 135                 140

Asp Asp Tyr Pro Arg Asp Val Arg Leu Ala Ala Ser Asn Trp Thr Gly
145                 150                 155                 160

Glu Gly Ser Phe Leu Phe Thr Ser Ser Thr Ala Leu Tyr Asp Cys Ser
                165                 170                 175

Asp Asn Ser Met Cys Asn Glu Asp Cys Leu Ser Val Pro Ile Gly Arg
            180                 185                 190

Ser Pro Arg Thr Asp Ile Leu Leu Lys Val Glu Asn Val Val Leu Glu
        195                 200                 205

Ala Gly Gly Cys Val Leu Arg Leu Ala Gly Leu Tyr Lys Ile Asp Arg
    210                 215                 220
```

Gly Ala His Val Phe Trp Leu Arg Lys Gly Thr Leu Asp Thr Arg Pro
225                 230                 235                 240

Asp His Ile Ile Asn Gln Ile His Tyr Glu Asp Ala Ala Ser Leu Ala
            245                 250                 255

Val Ala Ile Met Lys Lys Gly Leu Arg Ser Arg Ile Phe Leu Gly Cys
        260                 265                 270

Asp Asn Lys Pro Leu Ser Arg Gln Glu Ile Met Asp Ala Val Asn Asn
    275                 280                 285

Ser Gly Lys Phe Asp Thr Lys Phe Gly Gly Phe Thr Gly Thr Asp Gly
290                 295                 300

Pro Leu Gly Lys Arg Met Glu Asn Ser Lys Thr Arg Ala Glu Ile Gly
305                 310                 315                 320

Trp Glu Pro Lys Tyr Pro Ser Phe Thr Glu Phe Leu Gly Ile Ser Ser
                325                 330                 335

<210> SEQ ID NO 5
<211> LENGTH: 359
<212> TYPE: PRT
<213> ORGANISM: Zea mays

<400> SEQUENCE: 5

Met Gly Arg Ala Ala Pro Leu Leu Pro Arg Pro Ile Ile Ala Gln
1               5                   10                  15

Phe His Leu His Pro His Leu Val His Gln Ser Cys Leu Pro Tyr
                20                  25                  30

Leu His Ala Thr Ala Pro Val Ala Ala Ser Ala Leu Phe Ala Pro
            35                  40                  45

Gly Pro Thr Ser Ser Pro Ser Val Arg Val Ser Arg Pro Arg Arg His
50                  55                  60

Ala Ser Met Ser Ala Ala Ala Asp Ser Ser Ser Ile Val Val Ser
65                  70                  75                  80

Gly Asp Ala Ala Val Ser Ser Leu Ser Pro Glu Ser Ile Glu His Asn
                85                  90                  95

Asp Leu Leu Ile Val Gly Pro Gly Val Leu Gly Arg Ile Val Ala Glu
            100                 105                 110

Met Trp Lys Gln Glu Tyr Pro Gly Cys Lys Val Tyr Gly Gln Thr Ala
        115                 120                 125

Thr Thr Asp His His Ser Glu Leu Thr Asp Ile Gly Ile Ile Pro Ser
    130                 135                 140

Leu Lys Gly Ser Val Pro Gly Pro Lys Phe Pro Tyr Val Ile Phe Cys
145                 150                 155                 160

Ala Pro Pro Tyr Arg Ser Glu Asp Tyr Ala Gly Asp Leu Arg Val Ala
                165                 170                 175

Ala Ser Asn Trp Asn Gly Lys Gly Ser Phe Leu Phe Thr Ser Ser Thr
            180                 185                 190

Ala Val Tyr Asp Cys Ser Asp Asn Gly Phe Cys Ser Glu Asp Ser Pro
        195                 200                 205

Cys Val Pro Ile Gly Gln Ser Thr Arg Thr Asp Val Leu Leu Lys Ala
    210                 215                 220

Glu Asn Val Val Leu Glu Ala Gly Gly Cys Val Leu Arg Leu Val Gly
225                 230                 235                 240

Leu Tyr Lys Ser Asp Arg Gly Pro His Val Tyr Trp Leu Ser Lys Gly
                245                 250                 255

Thr Leu Asp Val Arg Pro Asp His Ile Leu Asn Leu Ile His Tyr Glu

```
            260                 265                 270
Asp Ala Ser Leu Val Ile Ser Ile Met Lys Lys Arg Leu Arg Ser
        275                 280                 285

Cys Ile Phe Val Gly Cys Asp Asn Glu Pro Leu Ser Arg Leu Glu Ile
        290                 295                 300

Met Asp Arg Val Asn Arg Ser Arg Lys Phe Asp Thr Gln Phe His Gly
305                 310                 315                 320

Phe Thr Gly Thr Asp Gly Pro Leu Gly Lys Arg Met Asp Asn Ser Lys
                325                 330                 335

Thr Arg Ala Lys Leu Gly Trp Gln Pro Lys Tyr Pro Ser Phe Thr Glu
            340                 345                 350

Phe Leu Gly Leu Ser Asn Leu
            355

<210> SEQ ID NO 6
<211> LENGTH: 343
<212> TYPE: PRT
<213> ORGANISM: Vitis vinifera

<400> SEQUENCE: 6

Met Gly Thr Leu Gly Ser Thr Thr Thr Leu Ser Pro Tyr Phe Ser Ser
1               5                   10                  15

Lys Leu Ser Phe Ser Ser Ser Phe His Arg Leu Arg Phe Ser Ala Ser
            20                  25                  30

Arg Ser Phe Leu Ser Ile Phe Arg Asn Pro Ser Phe Arg Ala Lys Arg
        35                  40                  45

Ser Val Ser Thr Asp Thr Arg Leu Arg Val Ser Ala Ser Ser Thr Leu
    50                  55                  60

Gly Ala Pro Asn Glu Glu Met Glu Thr Ser Ser Phe Gly Leu Val Gly
65                  70                  75                  80

Glu Asn Asp Leu Leu Ile Val Gly Pro Gly Val Leu Gly Arg Leu Val
                85                  90                  95

Ala Glu Lys Trp Arg Glu His Pro Gly Cys Gln Ile Tyr Gly Gln
            100                 105                 110

Thr Met Thr Thr Asp His His Asp Glu Leu Val Lys Ile Gly Ile Asn
        115                 120                 125

Pro Ser Leu Lys Gly Val Lys Thr Thr His Gln Phe Pro Tyr Val Ile
    130                 135                 140

Phe Cys Ala Pro Pro Ser Arg Thr Ser Asp Tyr Pro Ala Asp Val Arg
145                 150                 155                 160

Leu Ala Ala Ser Asn Trp Ser Gly Glu Gly Ser Phe Leu Phe Thr Ser
                165                 170                 175

Ser Ser Ala Pro Phe Asp Cys Asn Asp Asn Gly Ser Cys Asp Glu Asp
            180                 185                 190

Gly Pro Val Pro Ile Gly Arg Ser Pro Arg Thr Asp Val Leu Leu
        195                 200                 205

Asn Ala Glu Lys Gly Val Leu Glu Phe Gly Gly Cys Val Leu Arg Leu
    210                 215                 220

Ala Gly Leu Tyr Lys Ala Asp Arg Gly Ala His Val Tyr Trp Leu Lys
225                 230                 235                 240

Lys Gly Thr Val Glu Ala Arg Pro Asp His Ile Leu Asn Leu Ile His
                245                 250                 255

Tyr Glu Asp Ala Ala Ser Leu Ala Val Ala Ile Leu Lys Lys Lys Arg
            260                 265                 270
```

```
His Gly Gln Ile Phe Leu Gly Cys Asp Asn His Pro Val Ser Arg Gln
            275                 280                 285

Glu Leu Met Asp Leu Val Asn Lys Ser Gly Lys Phe Ser Lys Lys Phe
        290                 295                 300

Glu Ala Phe Thr Gly Thr Ser Asp Pro Leu Gly Lys Arg Leu Asn Asn
305                 310                 315                 320

Ser Lys Thr Arg Glu Glu Ile Gly Trp Gln Pro Lys Tyr Pro Ser Phe
            325                 330                 335

Ser Gln Phe Leu Glu Ser Ile
            340

<210> SEQ ID NO 7
<211> LENGTH: 304
<212> TYPE: PRT
<213> ORGANISM: Populus balsamifera subsp. trichocarpa

<400> SEQUENCE: 7

Met Ala Ala Pro Leu Gln Val Ser Ala Phe Ser Thr Ile Gly Ala Arg
1               5                   10                  15

Asn Glu Glu Leu Gly Thr Ala Ser Ser Gly Leu Val Gly Glu Asn Asp
            20                  25                  30

Leu Leu Ile Val Gly Pro Gly Val Leu Gly Arg Leu Val Ala Glu Lys
        35                  40                  45

Trp Arg Gln Glu His Pro Gly Cys Gln Val Tyr Gly Gln Thr Val Thr
50                  55                  60

Thr Asp His His Asp Glu Leu Ile Lys Met Gly Ile Asn Pro Ser Leu
65                  70                  75                  80

Lys Gly Thr Lys Ala Thr Gln Gln Tyr Pro Tyr Val Ile Phe Cys Ala
            85                  90                  95

Pro Pro Ser Arg Thr Ser Asp Tyr Pro Gly Asp Val Arg Glu Ala Ala
            100                 105                 110

Leu Ser Trp Asn Gly Asp Gly Ser Phe Val Phe Thr Ser Ser Ser Ala
        115                 120                 125

Pro Tyr Asp Cys Phe Asp Asn Gly Gln Cys Asn Glu Asp Ser Pro Val
    130                 135                 140

Val Pro Ile Gly Arg Ser Pro Arg Thr Asp Val Leu Leu Lys Ala Glu
145                 150                 155                 160

Lys Val Val Leu Glu Ser Gly Gly Cys Ala Ile Arg Leu Ala Gly Leu
            165                 170                 175

Tyr Ile Ser Phe Ser Val Leu Asn Tyr Val Asp Phe Ile Asn Asn Arg
        180                 185                 190

Gly Ala His Ala Tyr Trp Leu Glu Lys Gly Thr Val Glu Val Arg Pro
    195                 200                 205

Asp His Ile Leu Asn Leu Ile His Tyr Glu Asp Ala Ala Ser Leu Ala
    210                 215                 220

Val Ala Ile Leu Lys Lys Lys Leu Arg Ser Arg Ile Phe Leu Gly Cys
225                 230                 235                 240

Asp Asn His Pro Leu Ser Arg Gln Glu Val Met Asp Leu Val Ala Lys
            245                 250                 255

Ser Gly Lys Phe Ser Lys Phe Val Ala Phe Thr Gly Thr Ser Asp
            260                 265                 270

Pro Leu Gly Lys Arg Leu Asn Asn Ser Lys Thr Arg Glu Glu Ile Gly
        275                 280                 285

Trp Glu Pro Glu Tyr Pro Ser Phe Ala His Phe Leu Gly Val Ser Lys
        290                 295                 300
```

<210> SEQ ID NO 8
<211> LENGTH: 351
<212> TYPE: PRT
<213> ORGANISM: Arabidopsis thaliana

<400> SEQUENCE: 8

Met Gly Phe Ile Ser Cys Ile Ser Phe Pro Thr Ile Asn Ser Arg Ile
1               5                   10                  15

Leu Ser Thr His His Phe Ser Lys His Ser Thr Ser Ala Ser Ser Ser
            20                  25                  30

Tyr Ser Leu Lys Phe Ala Leu Arg Arg Gln Glu Asp Lys Pro Lys Val
        35                  40                  45

Ser Phe Phe Leu Pro Leu Thr Ser Ser Leu Met Ala Thr Pro Ile Gln
    50                  55                  60

Ala Ser Ser Ser Ser Thr Ile Gly Glu Thr Ser Asp Gly Leu Lys Val
65                  70                  75                  80

Gln Ser His Val Ser Ile Gly Ala Asn Asp Leu Leu Ile Val Gly Pro
                85                  90                  95

Gly Val Leu Gly Arg Leu Val Ala Glu Gln Trp Arg Gln Glu His Pro
            100                 105                 110

Glu Ser Gln Ile Phe Gly Gln Thr Val Thr Thr Asn His His Gly Glu
        115                 120                 125

Leu Glu Asn Leu Gly Ile Lys Pro Ser Leu Lys Gly Thr Glu Tyr Gly
    130                 135                 140

Gly Lys Phe Ser Tyr Val Ile Phe Cys Ala Pro Pro Ser Gln Ser Ala
145                 150                 155                 160

Asp Tyr Ala Gly Glu Val Arg Asn Ala Ala Ser Asn Trp Asn Gly Glu
                165                 170                 175

Gly Ser Phe Leu Phe Thr Ser Ser Ala Pro Tyr Asp Cys Phe Asp
            180                 185                 190

Asn Gly Glu Cys Asn Glu Asp Ser Pro Val Val Pro Leu Gly Lys Ser
        195                 200                 205

Pro Arg Thr Asp Val Leu Leu Lys Ala Glu Lys Val Val Leu Glu Cys
    210                 215                 220

Gly Gly Thr Val Leu Arg Leu Ala Gly Leu Tyr Thr Glu Thr Arg Gly
225                 230                 235                 240

Ala His Thr Tyr Trp Leu Ser Lys Glu Thr Ile Asp Ala Arg Pro Asp
                245                 250                 255

His Ile Leu Asn Leu Ile His Tyr Glu Asp Ala Ala Ser Leu Ala Val
            260                 265                 270

Ala Ile Met Lys Lys Lys Ala Gly Ala Arg Ile Phe Leu Gly Cys Asp
        275                 280                 285

Asn His Pro Leu Ser Arg Gln Glu Val Met Asp Leu Met Ala Gln Ser
    290                 295                 300

Gly Lys Phe Asp Lys Lys Phe Lys Gly Phe Thr Ser Thr Ser Gly Pro
305                 310                 315                 320

Leu Gly Lys Lys Leu Asn Asn Ser Lys Thr Arg Ala Glu Ile Gly Trp
                325                 330                 335

Glu Pro Lys Tyr Pro Ser Phe Ala Gln Phe Phe Gly Val Ser Thr
            340                 345                 350

<210> SEQ ID NO 9
<211> LENGTH: 287
<212> TYPE: PRT

<213> ORGANISM: Ricinus communis

<400> SEQUENCE: 9

Met Ala Asn Pro Phe Gln Val Ser Ala Ser Ser Thr Met Gly Ala Thr
1               5                   10                  15

Asn Glu Glu Leu Asp Ala Val Ser Ser Leu Val Gly Glu Asn Asp
            20                  25                  30

Leu Leu Ile Val Gly Pro Gly Val Leu Gly Arg Leu Val Ala Glu Lys
        35                  40                  45

Trp Arg Gln Glu His Pro Gly Cys Gln Val Tyr Gly Gln Thr Leu Thr
    50                  55                  60

Thr Asp His His Asp Glu Leu Ile Lys Ile Gly Ile Asn Pro Ser Leu
65                  70                  75                  80

Lys Gly Thr Lys Pro Ile His Gln Phe Pro Tyr Val Ile Phe Cys Ala
                85                  90                  95

Pro Pro Ser Arg Thr Ser Asp Tyr Pro Gly Asp Val Arg Glu Ala Ala
            100                 105                 110

Leu Ser Trp Asn Gly Glu Gly Ser Phe Leu Phe Thr Ser Ser Ala
        115                 120                 125

Pro Tyr Asp Cys Tyr Asp Asn Gly Asp Cys Asp Glu Asp Ser Pro Val
130                 135                 140

Val Pro Ile Gly Arg Ser Pro Arg Thr Asp Val Leu Leu Lys Ala Glu
145                 150                 155                 160

Lys Val Val Leu Glu Ser Asp Gly Cys Val Tyr Lys Ala Asp Arg Gly
                165                 170                 175

Ala His Val Tyr Trp Leu Gln Lys Gly Ile Val Glu Val Arg Pro Asp
            180                 185                 190

His Ile Leu Asn Leu Ile His Tyr Glu Asp Ala Ala Ser Leu Ser Ile
        195                 200                 205

Ala Ile Leu Lys Lys Phe His Gly Arg Ile Phe Leu Gly Cys Asp
    210                 215                 220

Asn His Pro Leu Ser Arg Gln Glu Val Met Asp Leu Val Ala Lys Ser
225                 230                 235                 240

Gly Lys Phe Ser Lys Lys Phe Glu Ala Phe Thr Gly Thr Gly Asp Pro
                245                 250                 255

Ser Gly Lys Arg Leu Asn Asn Ser Lys Thr Arg Glu Glu Val Gly Trp
            260                 265                 270

Glu Pro Asn Tyr Pro Ser Phe Ala His Phe Leu Gly Val Ser Asp
        275                 280                 285

<210> SEQ ID NO 10
<211> LENGTH: 284
<212> TYPE: PRT
<213> ORGANISM: Physcomitrella patens

<400> SEQUENCE: 10

Met Ser Gly Lys Glu Thr Glu Leu Glu Cys Asn Glu Glu Arg Ser Gln
1               5                   10                  15

Ile Thr Thr Asn Ser His Ala Asp Leu Leu Val Val Gly Pro Gly Val
            20                  25                  30

Leu Gly Ser Leu Val Gly Arg Arg Trp Leu Glu Leu His Glu Gly Cys
        35                  40                  45

Arg Val Val Gly Gln Thr Asn Thr Thr Asn Arg His Glu Glu Leu Leu
    50                  55                  60

Ser Leu Gly Ile Phe Pro Val Thr Lys Asp Ser His Ser Gly Asp Lys

```
             65                  70                  75                  80
    Phe Pro Tyr Val Ile Phe Cys Ala Pro Pro Ser Gly Ser Glu Asn Tyr
                     85                  90                  95

Ala Ala Glu Val Arg Ala Ala Gln Arg Trp Asn Gly Glu Gly Ser
                    100                 105                 110

Leu Leu Phe Thr Ser Ser Phe Val Tyr Asp Val His Asp Asn Gly
                    115                 120                 125

His Cys Asp Glu Ser Ala Pro Ile Thr Glu Lys Gly Thr Ser Pro Arg
    130                 135                 140

Gly Asp Arg Leu Leu Asn Ala Glu Glu Val Leu Lys Val Asp Gly
    145                 150                 155                 160

Asn Val Val Arg Leu Ala Gly Leu Tyr Ala Arg Asp Arg Gly Ala His
                    165                 170                 175

Met Tyr Trp Leu Gln Lys Gly Thr Val Asp Ala Arg Pro Asp His Phe
                    180                 185                 190

Leu Asn Leu Ile His Tyr Glu Asp Ser Ala Asp Leu Cys Ile Glu Ile
                    195                 200                 205

Leu Arg Lys Asn Leu Arg Gly Gln Ile Phe Met Gly Cys Asp Asn Thr
    210                 215                 220

Pro Val Ser Arg Gln Asp Ile Met Asp Ile Met Met His Ser Gly Lys
    225                 230                 235                 240

Phe Ala Gly Asn Phe His Gly Phe Thr Lys Ser Asp Gly Pro Leu Gly
                    245                 250                 255

Lys Lys Met Asn Asn Ser Gln Thr Arg Glu Arg Leu Gly Trp Gln Pro
                    260                 265                 270

Lys Tyr Asn Ser Phe Lys Asp Tyr Val Ser Thr Leu
                    275                 280

<210> SEQ ID NO 11
<211> LENGTH: 355
<212> TYPE: PRT
<213> ORGANISM: Ostreococcus tauri

<400> SEQUENCE: 11

Met Ser His Ala Leu Met Ser Arg Ala His Val Thr Asn Val Ile
    1               5                   10                  15

Gln Thr Ser Ser Arg Ile Arg Lys Arg Ser Cys Thr Ser Lys His Phe
                    20                  25                  30

Pro Ser Phe Arg Ala Ala Ala Ala Ser Thr Ser Ser Ala Val Cys
                    35                  40                  45

Ala Ser Phe Thr Pro Pro Gly Ala Arg Glu His Asp Arg Asp Leu Leu
    50                  55                  60

Ile Val Gly Pro Gly Val Leu Gly Ser Arg Ile Ala Arg Val Trp Leu
    65                  70                  75                  80

Glu Lys Tyr Pro Gly Ala Val Val Gly Gln Thr Asn Thr Thr Asn
                    85                  90                  95

Ala His Ala Gly Leu Thr Ser Ile Gly Val Ser Pro Arg Thr Lys Asp
                    100                 105                 110

Phe Asp Asp Glu Pro Ser Ala Asn Arg Met Phe Pro Tyr Val Ile
                    115                 120                 125

Phe Ser Ala Pro Pro Ser Gly Ser Asp Asp Tyr Ala Gly Glu Val Glu
                    130                 135                 140

Ala Ala Leu Arg Tyr Trp Asn Gly Gly Gly Ala Phe Ala Phe Thr Ser
    145                 150                 155                 160
```

-continued

```
Ser Ser Ala Val Tyr Lys Asn Glu Ser Gly Asp Ala Cys Asp Glu Asp
            165                 170                 175

Ser Glu Thr Tyr Asp Leu Gly Thr Asn Pro Arg Val Asp Arg Leu Leu
        180                 185                 190

Lys Ala Glu Arg Ile Val Leu Asp Ala Gly Val Val Cys Arg Leu
        195                 200                 205

Ala Gly Leu Tyr His Ser Asp Arg Gly Ala His Lys Tyr Phe Ile Lys
        210                 215                 220

Thr Pro Ser Ile Asp Ser Arg Ala Asp Ala Leu Val Asn Leu Ile His
225                 230                 235                 240

Tyr Glu Asp Ala Ala Asp Leu Cys Val Ala Ala Met Asn Asn Gly Ser
                245                 250                 255

Lys Ser Ala Val Tyr Leu Gly Thr Asp Gly Val Pro Ile Thr Arg Gly
                260                 265                 270

Asp Ile Ala Arg Val Ala Val Glu Ser Gly Ala Tyr Gly Ala Asp Ala
            275                 280                 285

Arg Ala Pro Ser Phe Thr Lys Thr Glu Gly Pro Ile Gly Arg Val Met
        290                 295                 300

Ser Asn Asp Arg Thr Arg Thr Ala Leu Gly Trp Ala Pro Lys Tyr Val
305                 310                 315                 320

Ser Phe Glu Thr Phe Met Thr Arg Val Asn Ala Arg Asp Ala Tyr Ser
                325                 330                 335

Ala Ser Glu Lys Arg Pro Val Gly Trp Ala Pro Lys Gly Ser Ala His
                340                 345                 350

Ile Ala Thr
        355

<210> SEQ ID NO 12
<211> LENGTH: 344
<212> TYPE: PRT
<213> ORGANISM: Ostreococcus tauri

<400> SEQUENCE: 12

Met Arg Ala Ser Ser Ala Ser Pro Arg Ala His Arg Ala Phe Pro Ser
1               5                   10                  15

His Thr Ala Arg Lys Thr Ser Arg Glu Lys Ala Ser Ser Arg Ser Arg
            20                  25                  30

Ala Val Ala Ala Ala Ser Thr Ser Asp Ala Pro Gly Pro Phe Gly Asp
        35                  40                  45

Asp Arg Asn Leu Leu Val Val Gly Pro Gly Val Leu Gly Ser Arg Ile
    50                  55                  60

Ala Arg Val Trp Leu Ser Asn Phe Pro Gly Ala Val Val Gly Gln
65                  70                  75                  80

Thr Asn Thr Asp Ala Ala His Asp Gly Leu Arg Ser Val Gly Val Thr
                85                  90                  95

Pro Arg Thr Lys Asp Phe Gly Ala Asp Pro Thr Ala Thr Arg Arg
            100                 105                 110

Phe Pro Tyr Val Val Phe Ser Ala Pro Pro Ser Gly Ser Glu Asp Tyr
        115                 120                 125

Pro Gly Glu Val Ala Ala Leu Lys Tyr Trp Asp Gly Ser Gly Ala
    130                 135                 140

Phe Ala Phe Thr Ser Ser Ser Ala Val Tyr Lys Asn Glu Ala Gly Glu
145                 150                 155                 160

Ala Cys Asp Glu Glu Ser Glu Val Tyr Glu Ile Gly Thr Asn Pro Arg
                165                 170                 175
```

```
Val Asp Arg Leu Leu Lys Ala Glu Lys Val Leu Asp Ala Gly Gly
            180                 185                 190

Val Val Cys Arg Leu Ala Gly Leu Tyr His Ser Glu Arg Gly Ala His
            195                 200                 205

Lys Tyr Phe Ile Lys Thr Ser Ser Leu Asp Ser Arg Ala Asp Ala Leu
            210                 215                 220

Val Asn Leu Ile His Tyr Glu Asp Ala Ala Asp Leu Cys Phe Ala Ala
225                 230                 235                 240

Met Thr Lys Gly Ala Lys Ser His Ile Tyr Leu Gly Thr Asp Gly Val
                245                 250                 255

Pro Ile Thr Arg Glu Ala Ile Ala Arg Val Ser Val Glu Ser Gly Val
            260                 265                 270

Tyr Gly Ala Asp Ala Ala Pro Ala Phe Thr Lys Thr Asp Gly Pro
            275                 280                 285

Leu Gly Arg Ala Met Ser Asn Ser Arg Thr Lys Thr Glu Leu Asp Trp
            290                 295                 300

Ser Pro Arg Tyr Glu Ser Phe Glu Ser Phe Ala Leu Arg Gln Gly Ala
305                 310                 315                 320

Arg Asp Ser Tyr Ala Pro Trp Asn Ala Pro Thr Arg Ser Arg Gly Trp
                325                 330                 335

Thr Pro Ala Gly Ala Arg His Val
            340

<210> SEQ ID NO 13
<211> LENGTH: 294
<212> TYPE: PRT
<213> ORGANISM: Micromonas pusilla

<400> SEQUENCE: 13

Met Ala Ala Val Ser Glu Ser Cys Cys Arg Asp Leu Leu Val Val Gly
1               5                   10                  15

Pro Gly Val Leu Gly Ser Leu Val Cys Gln Arg Trp Leu Lys Thr Phe
            20                  25                  30

Pro Ala Ala Thr Val Ile Gly Gln Thr Asn Thr Asp Ala Ser His Glu
        35                  40                  45

Arg Leu Val Ala Leu Gly Ile Ser Pro Arg Leu Lys Ala Asp Ala Gly
    50                  55                  60

Glu Ser Arg Arg Phe Pro Phe Val Val Phe Ser Ala Pro Pro Ser Gly
65                  70                  75                  80

Ser Asp Asp Tyr Thr Ala Glu Val Glu Ala Ala Leu Lys Leu Trp Asp
                85                  90                  95

Gly Thr Gly Gly Phe Val Phe Thr Ser Ser Thr Ala Val Tyr Ala Gly
            100                 105                 110

Lys Asp Gly Glu Asp Cys Asp Glu Thr Thr Ala Gln Phe Gln Ile Gly
        115                 120                 125

Glu Ser Pro Arg Ala Asp Lys Leu Leu Asn Ala Glu Ala Ala Val Leu
    130                 135                 140

Gly Ala Gly Gly Cys Val Val Arg Leu Ser Gly Leu Tyr His Ser Gln
145                 150                 155                 160

Arg Gly Ala His Met Tyr Phe Leu Lys Thr Pro Thr Leu Ala Ser Arg
                165                 170                 175

Pro Asp Ala Leu Val Asn Leu Val His Tyr Glu Asp Ala Ala Ala Ala
            180                 185                 190

Cys Val Arg Ala Leu Ser Ala Gln Leu Glu Gly Ser Ser Glu Gly Gly
```

```
            195                 200                 205
Glu Ile Phe Leu Ala Thr Asp Gly Val Pro Val Thr Arg Glu Lys Met
    210                 215                 220

Val Glu Ala Cys Leu Ala Cys Pro Asp Ala Tyr Asp Asp Gly Ala Met
225                 230                 235                 240

Pro Glu Phe Ser Val Ser Asp Gly Pro Leu Gly Lys Ser Met Thr Asn
                245                 250                 255

Pro Gln Thr Arg Glu Lys Leu Gly Trp Glu Pro Val Tyr Pro Ser Phe
                260                 265                 270

Val Glu Phe Val Ala Ala Gly Ala Lys Asp Ser Phe Tyr Pro Pro Lys
            275                 280                 285

Lys Lys Asn Thr Trp Ser
            290

<210> SEQ ID NO 14
<211> LENGTH: 293
<212> TYPE: PRT
<213> ORGANISM: Micromonas pusilla

<400> SEQUENCE: 14

Met Ser Ser Cys Thr Phe Ala Thr Pro Arg Val Glu Val Ile Arg Ser
1               5                   10                  15

Arg Gly Ser Pro Leu Ser Ala Arg Ala Arg Ser Ser Ser Ser Ser Ser
            20                  25                  30

Lys Phe Pro Ala Ala Ser Val Ile Gly Gln Thr Asn Thr Asp Thr Ser
        35                  40                  45

His Glu Arg Leu Leu Ser Leu Gly Val Phe Pro Arg Leu Lys Glu Lys
    50                  55                  60

Ala Gly Asp Glu Gln Tyr Pro Phe Val Val Phe Ser Ala Pro Pro Ser
65                  70                  75                  80

Gly Ser Glu Asp Tyr Ala Ala Glu Val Glu Ala Ala Leu Lys Tyr Trp
                85                  90                  95

Asp Gly Ser Gly Ala Phe Val Phe Thr Ser Ser Thr Ala Val Tyr Ala
            100                 105                 110

Gly Lys Asp Gly Glu Pro Cys Asp Glu Ser Thr Pro Gln Phe Glu Ile
        115                 120                 125

Gly Glu Ser Pro Arg Ala Asp Arg Leu Leu Lys Ala Glu Ala Ala Val
    130                 135                 140

Leu Ala Ala Gly Gly Ser Val Val Arg Leu Ala Gly Leu Tyr His Ser
145                 150                 155                 160

Gln Arg Gly Ala His Met Tyr Phe Leu Lys Thr Pro Ser Leu Ala Ser
                165                 170                 175

Asn Ala Asp Gly Leu Val Asn Leu Ile His Tyr Glu Asp Ala Ala Ala
            180                 185                 190

Ala Cys Val Asp Val Leu Val Ala Gln Phe Glu Gly Arg Thr Gly Gly
        195                 200                 205

Gly Glu Val Phe Leu Ala Thr Asp Gly Val Pro Val Thr Arg Lys Glu
    210                 215                 220

Met Val Glu Cys Cys Leu Glu Ser Asp Ala Tyr Asp Gly Asn Met Pro
225                 230                 235                 240

Glu Phe Thr Glu Asp Asn Gly Pro Leu Gly Lys Ser Met Asn Asn Pro
                245                 250                 255

Gln Thr Arg Glu Lys Leu Gly Trp Val Pro Val His Ala Ser Phe Val
            260                 265                 270
```

```
Glu Phe Val Glu Ala Gly Ala Thr Asp Ser Phe Tyr Pro Lys Arg Arg
            275                 280                 285

Lys Ser Thr Trp Lys
    290

<210> SEQ ID NO 15
<211> LENGTH: 380
<212> TYPE: PRT
<213> ORGANISM: Chlamydomonas reinhardtii

<400> SEQUENCE: 15

Met Ser Pro Arg Ser Cys Leu Ser Ala Ser Pro Thr Ser Val Ala
1               5                   10                  15

Thr Arg Thr Thr Phe Thr Ser Thr Cys Ile Pro Arg Pro Arg Ala Ala
                20                  25                  30

Gly Val Gln Val Ser Ala Gln Leu Asn Ile Ser Arg Arg Ser Ala Ser
            35                  40                  45

Ala Ala Ala Ile Ala Ser Val Ala Pro Leu Gly Met Thr Phe Pro Gly
        50                  55                  60

Ser Ile Asp Gly Gly Ala Ala Arg Gly Ser Val Ala Ala Ala Ala Thr
65                  70                  75                  80

Ser Ser Leu Ala Gly Ala Val Ala Gly Ser Pro Ser Asn Leu Asp Leu
                85                  90                  95

Leu Val Val Gly Pro Gly Val Leu Gly Ser Val Leu Gly Arg Asp Trp
            100                 105                 110

Leu Ala Ser Val Gln Gly Gly Thr Ala Thr Gly Leu Thr Asn Thr Asp
        115                 120                 125

Arg Ser His Glu Arg Leu Arg Ala Met Gly Leu Thr Pro Ala Thr Arg
130                 135                 140

Ser Thr Leu Pro Pro Asn Lys Lys Tyr Ser Phe Val Ala Phe Ala Ala
145                 150                 155                 160

Pro Pro Ser Gly Ser Glu Asp Tyr Val Ala Asp Ile Lys Ser Ala Leu
                165                 170                 175

Ala Leu Trp Asp Gly Ser Gly Ser Phe Ile Phe Thr Ser Ser Met Ser
            180                 185                 190

Val Cys Ala Val Asp Asp Gly Gly Ser Ala Thr Asp Glu His Cys Pro
        195                 200                 205

Leu Val Pro Val Gly Ala Gly Pro Ser Thr Asp Lys Leu Arg Gly Ala
    210                 215                 220

Glu Glu Ala Val Leu Ala Ala Gly Gly Asn Val Leu Arg Leu Val Gly
225                 230                 235                 240

Leu Tyr His Lys Phe Arg Gly Ala His Thr Phe Ile Lys Gln Gly
                245                 250                 255

Thr Val Ala Arg Pro Gly Gly Tyr Val Val Asn Leu Leu His Tyr Glu
            260                 265                 270

Asp Ala Ala Ala Leu Ala Ala Ala Ile Leu Arg Gly Asp Gly Ser Gly
        275                 280                 285

Pro Phe Arg Gly Arg Ala Phe Leu Gly Thr Asp Gly His Pro Val Thr
    290                 295                 300

Phe Glu Asp Met Val Glu Tyr Cys Phe Ala Gly Gly Ala Phe Glu Arg
305                 310                 315                 320

Val Pro Val Ser Phe Thr Gly Thr Phe Pro Asp Gly Lys Thr Gly
                325                 330                 335

Arg Gly Lys Arg Val Asp Asn Ser Gly Thr Ser Gln Ala Leu Gly Gly
            340                 345                 350
```

```
Trp Lys Pro Lys Tyr Glu Ser Phe Gln Ser Phe Met Ala Ala Gly Gly
        355                 360                 365

Ala Asp Tyr Tyr Asn Thr Ser Gly Leu Lys Trp Asn
    370                 375                 380

<210> SEQ ID NO 16
<211> LENGTH: 292
<212> TYPE: PRT
<213> ORGANISM: Phaeodactylum tricornutum

<400> SEQUENCE: 16

Met Ala Thr Lys Thr Ser Ser Gly Cys Ala Val Ile Gly Val Gly Val
1               5                   10                  15

Leu Gly Thr Ser Leu Cys Gln Gln Ile Leu Ser Ala Pro Glu Phe Asp
            20                  25                  30

Gly Ile Lys Leu Thr Gly Ile Thr Lys Thr Thr Asn His Asn Ala
        35                  40                  45

Ile Arg Glu Lys Val Gly Met Asp Ser Glu Asp Arg Phe Gln Leu Leu
    50                  55                  60

Thr Thr Asp Glu Cys Glu Gly Thr Glu Thr Lys Phe Lys His Ile Val
65                  70                  75                  80

Phe Cys Ala Pro Pro Ser Gly Ser Glu Asp Tyr Pro Ala Asp Val Arg
                85                  90                  95

Lys Ser Ala Asp Thr Leu Trp Ala Gly Pro Glu Gly Gly Val Phe
            100                 105                 110

Val Phe Thr Ser Ser Gly Ala Val Tyr Gly Pro Gly Asp Ser Arg Thr
            115                 120                 125

Val Ser Glu Thr Ser Asp Ile Ala Asp Pro Glu Ser Ser Val Arg Val
    130                 135                 140

Gly Arg Leu Val Lys Ala Glu Lys Ala Ala Leu Asp Ala Gly Gly Cys
145                 150                 155                 160

Val Leu Arg Leu Ala Gly Leu Tyr Asn Leu Asp Arg Gly Ala His Asn
                165                 170                 175

Phe Trp Leu Thr Ser Gly Lys Pro Ile Ser Gly Leu Pro Glu Gly Ile
            180                 185                 190

Ile Asn Leu Leu His Tyr Glu Asp Ala Ala Ser Ala Cys Leu Ser Ala
        195                 200                 205

Leu Lys Ala Gly Ser Ser Val Cys Glu Gly Arg Ala Phe Ile Ile Ser
    210                 215                 220

Asp Gly His Pro Leu Thr Arg Lys Gln Ile Cys Glu Ser Ala Leu Gln
225                 230                 235                 240

Ala Lys Thr Tyr Lys Asp Cys Ala Met Pro Thr Phe Ala Ser Glu Asn
                245                 250                 255

Leu Asn Gly Met Ala Leu Gly Lys Val Tyr Asp Gly Ser Ser Ser Asn
            260                 265                 270

Lys Ala Leu Glu Trp Ser Pro Arg Phe Glu Ser Phe Asp Thr Phe Met
        275                 280                 285

Asn Ser Met Ala
    290

<210> SEQ ID NO 17
<211> LENGTH: 274
<212> TYPE: PRT
<213> ORGANISM: Thalassiosira pseudonana

<400> SEQUENCE: 17
```

```
Met Ala Val Leu Ser Leu Leu Thr Ala Leu Leu Val Leu Ser Pro Ala
1               5                   10                  15

Arg Ala Phe Ser Thr Pro Gln Pro Ile Thr Ser Asp Leu Ala Ile Val
            20                  25                  30

Gly Cys Gly Val Leu Gly Thr Ser Leu Cys Lys Gln Leu Leu Ser His
        35                  40                  45

Pro Asp Phe Ser Ser Arg Ser Ile Thr Ala Ile Thr Lys Thr Thr Gly
    50                  55                  60

Arg His Asp Ala Ile Arg Ala Glu Val Gly Asp Gly Asp Thr Asp
65                  70                  75                  80

Arg Phe Ala Val Leu Thr Met Asp Asp Val Leu Ala Gln Tyr Ser Gly
                85                  90                  95

Asn Ser Phe Lys Asp Val Val Phe Cys Ala Pro Pro Ser Gly Phe Asp
            100                 105                 110

Asp Tyr Pro Gln Ala Val Lys Asp Ala Ala Thr Gln Leu Trp Ser Gly
        115                 120                 125

Pro Ser Ser Gly Gly Ser Phe Val Phe Thr Ser Ser Gly Gly Val Tyr
    130                 135                 140

Glu Gly Leu Asp Gly Glu Thr Val Asn Glu Ser Ser Pro Thr Leu Asp
145                 150                 155                 160

Ala Glu Ala Asn Pro Arg Gln Gly Arg Leu Ile Asn Ala Glu Arg Glu
                165                 170                 175

Cys Ile Ala Leu Gly Gly Cys Ala Leu Arg Leu Ala Gly Leu Tyr Thr
            180                 185                 190

Leu Glu Arg Gly Ala His Asn Tyr Trp Leu Glu Lys Cys Thr Glu Gly
        195                 200                 205

Val Gln Gly Arg Glu Asp Gly Ile Val Asn Leu Leu His Tyr Asp Asp
    210                 215                 220

Ala Ala Ser Ala Cys Leu Ala Ala Leu Gln Val Gly Pro Asp Val Asn
225                 230                 235                 240

Ser Lys Gln Thr Tyr Leu Ile Ser Asp Gly Asn Pro Thr Thr Arg Lys
                245                 250                 255

Gly Ile Cys Glu Ser Ala Leu Lys Ser Ala Arg Trp Phe Glu Gly Glu
            260                 265                 270

Asn Leu
```

<210> SEQ ID NO 18
<211> LENGTH: 1397
<212> TYPE: DNA
<213> ORGANISM: Oryza sativa

<400> SEQUENCE: 18

```
ctgctccaat ccactctcct ccgtttgcct gatccgatcc cctcacctcc gtccctgctt    60
cctcccggcg accaccgccc gccgcgcgat gggcggcgcc gccgtctcca gcctgcttgc   120
cacccccaaca ccgacctctc gacctcgacc cgtctccacc accaccgccc ccttctccgt   180
caacctctcc accgcagctg cccgcgcacc tcgcctcctc ctcctctcgc gccgccctcg   240
ccctcgcccc gccgccgcgg ttctcggggt gtctgatgat acaggggtca agatggctgg   300
ctccgacatt gttggcaaga cgatttgct gattgttggc cctggagtgc ttggtcgact   360
ggtagctgag aaatggcagg aggaacatcc aggatgcaaa gtttttggcc agaccgcaag   420
cacagatcac cacaacgaat tgtcgaatat tggcatcatt ccctccttga agggatccac   480
ttttcctcag aaggttccat atgttatttt ctgtgctccc ccatctcgtt cggatgatta   540
```

```
cctgggat gtgagagtag ctgcctcaaa ttggactggt gaaggctctt tcgttttac      600
atcaagtact gctctgtacg attgtagtga caacgaattg tgcaatgagg attgcccatc    660
tgtgccaatt ggcagaagcc ctcgtactga cgtccttcta aaagcagaga atgttgttct    720
tgaggcagga ggctgtgtcc tcaggctagc aggactctat aaaatagata gaggtgctca    780
ttttttttgg ttgaggaaag gaactttgga cacacgacca gatcatatta tcaatcaaat    840
tcattatgag gatgctgctt cccttgcaat tgccataatg aaaaagggac acaggggtcg    900
aatcttttg ggctgtgaca ataagcctct ttccaggcaa gaaataatgg actctgttaa     960
cagaagtgga aaatttgaca cgaagttcca aggttttact ggtacagatg gtccactggg   1020
taagaagatg gagaattcga gaactcgttc tgagattggt tgggagccca agtatccaag   1080
cttcacagaa ttccttggtc ttgacagttg acatgcttgt gtatgcttgc aaaaatcttc   1140
aactctaaat gaacagcaac acgttgtgaa ccagttattt tgttttgttt ccattgcgtt   1200
tttttttaaaa gacgtaaata ctgtatatct tgttctgcta tgtgcttata tcagttagcg  1260
ttctaagtct gaccgttgta caatggtttc ggccagagaa atatttccac ccgtgtcatg   1320
ttggcctcgt tctggtccgt ccaacatcta tttgtctctt tgtaaccaca tttgttatga   1380
aaacttggtt tcctttc                                                   1397
```

```
<210> SEQ ID NO 19
<211> LENGTH: 1425
<212> TYPE: DNA
<213> ORGANISM: Sorghum bicolor
<400> SEQUENCE: 19
tactggaact cgatccactg tccatcttcc ccgtctactc tttcctcacc gtcacactgt     60
cgccgccgcc gccgcgaccg cgaccccgcc ggccgacgag atgagagccg ccgctgcggc    120
ctccttccat ctggcacccg ctacgaaccc ggcccatccc cgcggctcca cgacagactc    180
ctgttccctg aaacctgcac cgactgctca gccacctcgc ctccgttcgc tcgcccgccg    240
cgcgcctctc gtctgcgcct ctctcgggat atctcatgat aaagggtctg atatttccga    300
ccccaatgtt gttggccaga atgatttact gattgtgggc cctggtgttc ttggacgaat    360
tgtagctgag aagtggcaaa aggagcatcc aggttgcaaa gtttatggcc agactgcaag    420
caagaatcat cacagtgagt taacagatct tggcatcatc ccctcattga aaggcaccac    480
tattcatcag aaggttccac atgttatttt ctgcgctccc ccgtccagtt cagatgatta    540
tcctggggat gttagattgg cagcatcaaa ttggagtggt gaaggatctt tcctgtttac    600
atcaagtaca gctctgtatg actgcagtga caacagcatg tgcaacgagg attgttcgtc    660
agtgccaatt ggcaggagcc ctcgtactga tgtacttcta aaagtggaaa atgttgttct    720
tgaggcagga ggctgtgttc ttaggctagc tggactttat aagatagaca gaggtgctca    780
tgttttctgg ttgaggaaag gaacgttaga cacaagacca gatcatatca tcaatcagat    840
tcattatgag gatgccgctt cccttgcagt agcaatcatg aaaaagagac tgcggagtcg    900
gatatttttg ggctgtgaca acaagcccct ttccaggcaa gagataatgg atgctgttaa    960
caaaagtggg aaatttgaca cgaagtttga aggcttact ggtactgacg gtccattggg   1020
gaagagaatg gagaattcga aaactcgggc tgagatcggt tgggaaccga agtatccaag   1080
cttcaccgaa ttccttggta tcagcagtta acatccttgc atacttgtca gttactctga   1140
ctcagctgtg tagcaaccac gattagattg taccatcgtt tgaatttgat aatggtctca   1200
```

| | |
|---|---:|
| actggtgagg gtgcatatct tagtctactc cgggcctgtc ctcagtattt tttgattctc | 1260 |
| acacttttg tgttgtgaac cagactgatg caacccccacc cctccaggca acatatatat | 1320 |
| actgtcacgt gagtcgattt gtcgatcatg aacatatact ctgccgacta ccgtggtcgt | 1380 |
| ataactgcaa actagtttta aggtctggtc ctccggccag caagt | 1425 |

<210> SEQ ID NO 20
<211> LENGTH: 994
<212> TYPE: DNA
<213> ORGANISM: Sorghum bicolor

<400> SEQUENCE: 20

| | |
|---|---:|
| atgtccgccg ccgcagccga ctcctcctcc tcttcctcca tcggaatacc gcgtgatgcg | 60 |
| gcggttagct cgctctcgcc cgagagcgtc agcaacaacg atctgctcat cgttgggccg | 120 |
| ggcgtgctcg gccggatcgt cgccgagatg tggaaacagg aatatccagg ttgcaaggtt | 180 |
| tgtggccaga ctgcaaccac agatcatcac agtgaattaa ctgacattgg tatcattccc | 240 |
| tccttgaaga ggtccgtagc gggtcccaaa tttccaaatg ttattttctg tgctccacca | 300 |
| tatcgttctg aggattatgc tggagatctg agaatagcag cttcgaattg gaatggagaa | 360 |
| ggttctttcc tattcacctc gagtactgct gtgtatgact gcagtgacaa tggattctgc | 420 |
| ggtgaggatt ctccttgtgt atcgattggt cagagccctc gtactgatgt gcttctaaaa | 480 |
| gctgaaaatg ttgtccttga ggcagggggc tgtgttctta ggctagcagg actttacaaa | 540 |
| tcagatcgag gtcctcatgt ctattggttg tcaaaaggaa ccttggatgt gcgtcctgat | 600 |
| catatactca atctgataca ttatgaagat gcagcctctc ttgcaattgc catcatgaaa | 660 |
| aagagattac ggagccgcat ctttgtgggc tgtgacaatg agcctctgtc caggctagag | 720 |
| attatggacc gtgtcaacag aagcgggaaa tttgagacac agtttcaggg cttcactggg | 780 |
| actgatggtc cgctggggaa gaggatggag aactccaaaa ctcgggcaga gctcggatgg | 840 |
| cagcccaagt atccgagctt tacagagttc cttggtctca gcaatctcta actttcatgc | 900 |
| gttgtcgcta aatacttgtg attaaagatg aatatactgg tacatgaaag aaacaatgac | 960 |
| aaatttgaag tggaatgttg gttcctcata ctac | 994 |

<210> SEQ ID NO 21
<211> LENGTH: 1275
<212> TYPE: DNA
<213> ORGANISM: Zea mays

<400> SEQUENCE: 21

| | |
|---|---:|
| cacatcgccg ctgccgcgac ccgcgggccg acgagatgag agccgccgct gcggcctcct | 60 |
| tccatctggc acccgccacg aaaccggccc atcgccgcgg ctgcaccaca gagtcctgtt | 120 |
| ccctgaagcc tgcgccgact gctcggccac ctcgcctccg ctcgctcgcc ggccgggcgc | 180 |
| ctcttgtctg cgcctctctc gggatatctc atgataaagg gttcgacatt tctgaccca | 240 |
| atgttgttgg acagaatgat ttactgattg tgggccctgg tgttcttggg cgaatcatag | 300 |
| ctgagaagtg gaaaaggag catccaagtt gcaaagttta tggccagacc gcaagcaaaa | 360 |
| atcatcacaa cgagttaaca gatcttgca tcatcccctc attgaaaggc accactgttc | 420 |
| atcagaaggt tccacatgtt attttctgcg ctccccgtc tggttcagat gattaccta | 480 |
| gggatgtcag attggcagca tcaaattgga ctggtgaagg atctttcctg tttacatcaa | 540 |
| gtacagctct gtatgattgc agtgacaaca gcatgtgcaa cgaggattgt ctgtcagtgc | 600 |
| caattggcag gagccctcgt actgatattc ttctaaaagt ggaaaatgtt gttcttgagg | 660 |

```
caggaggctg tgttctcagg ctggctggac tttataagat agacagaggt gcacatgttt    720
tctggttgag gaaaggaact ttagacacac gaccagatca tatcatcaac cagattcatt    780
atgaggatgc tgcctccctt gctgtagcaa tcatgaaaaa gggactgcgg agtcgaatat    840
ttctgggttg tgacaacaag cccctttcca ggcaagaaat aatggatgct gttaacaata    900
gtggaaaatt tgacacgaag tttggaggct ttactggtac tgacggtcca ttggggaaga    960
gaatggagaa ttcaaaaact cgggctgaga tcggttggga accaaagtat ccaagcttca   1020
ccgaattcct tggtatcagc agttaacatc cttgcatact gttcagttag tctgactcag   1080
ctgagtagca accgtgatta gattgtacca tcgtttgaat ttttatggcc tgaaccggtg   1140
atggtgtaca tctcagccta ctttgggcct gtccccagta tttttgattt tcacactatt   1200
tgagctatga accagacaga tgccacccca tcccatcgga taatatatat tgtcacgtga   1260
gtggatttgt cgatc                                                    1275

<210> SEQ ID NO 22
<211> LENGTH: 1365
<212> TYPE: DNA
<213> ORGANISM: Zea mays

<400> SEQUENCE: 22
ctccaacgtc cacgagacgc cgccacgcca tcggcatggg cagggcagca gcaccacttc     60
taccgcgtcc cattattgcc cagttccatc tccatcccca ccatctcgtc caccagtcgt    120
gtcttcccta tctccacgct accgcacctg tcgccgccgc ctccgccctc tttgctcccg    180
gccccacttc aagcccaagc gtccgcgtct cccgcccgcg ccgccacgcc tcgatgtccg    240
ccgccgccga ttcctcctcc tccattgtag tatcgggtga tgcagcggtt agctcgctct    300
cgcccgagag catcgagcac aacgatctgc tcatagttgg gcctggcgtg ctcggccgaa    360
tcgtcgctga gatgtggaaa caggaatatc caggttgcaa ggtttatggc cagactgcaa    420
ccacagatca tcacagtgaa ttgactgata ttggtatcat tccctccttg aaggggtccg    480
taccgggtcc aaaatttcca tatgttatct tctgtgctcc tccatatcgt tctgaggatt    540
atgctggaga tctgagagta gcagcttcaa attggaatgg aaaaggctct ttcctattca    600
cctcgagtac tgctgtgtat gactgcagtg acaatggatt ctgcagtgag gattctcctt    660
gtgtacccat tggtcaaagc actcgtactg atgtgcttct aaaagctgaa aatgttgtcc    720
ttgaggcagg cggctgtgtt cttaggctag taggacttta taaatcagat cggggtcctc    780
atgtttactg gctgtcaaaa ggaaccttgg atgtgcgtcc tgatcatata ctcaatctga    840
tacattatga agatgcagcc tctcttgtaa tttccatcat gaaaaagaga ttacggagct    900
gcatctttgt gggttgtgac aacgagcctc tgtccaggct agagatcatg gaccgtgtca    960
acagaagcag gaaatttgac acacagtttc atggcttcac tgggactgat ggtccgctgg   1020
ggaagaggat ggacaactcc aaaactcggg caaagcttgg atggcagccc aagtatccga   1080
gctttacaga gttccttggt ctcagcaatc tctaactttc atgcgatgtc actaaatacc   1140
tgttattaaa gatgaatata ctgatacata aaagagatga tgacagattt ggaagtggaa   1200
tgttgtttgc ttataccgca gttttcgact atcttttgat ttcttctgtt agatcttgta   1260
aagcattgca gcatggtgtg gcatgtacct gtgttgcctt ctattcgctt ctgttaactc   1320
atgaaagcat tgacttcaat acctgttaat tgtttccatg gcttc                   1365

<210> SEQ ID NO 23
```

<211> LENGTH: 1294
<212> TYPE: DNA
<213> ORGANISM: Vitis vinifera

<400> SEQUENCE: 23

| | | | | | |
|---|---|---|---|---|---|
| atgggcactc | ttggttcgac | aaccactctc | tctccgtact | tctcctccaa | gctctccttt | 60 |
| tcctcttcgt | ttcatcggct | ccgcttcagc | gcctccagat | cgttcctctc | tatcttcaga | 120 |
| aaccctagct | ttcgtgcgaa | acgcagtgtt | caacagaca | ctcgtcttcg | agtcagcgcg | 180 |
| tcgtccacgc | ttggtgcacc | aaacgaagaa | atggagactt | cttcttttgg | tttggttgga | 240 |
| gagaatgacc | ttctgattgt | tggacctggt | gttcttgggc | gcttggtagc | ggaaaaatgg | 300 |
| cgggaggaac | atccaggatg | tcaaatttat | ggtcaaacta | tgactacaga | tcatcatgat | 360 |
| gaattggtta | aaattgggat | aaatccatct | ttgaagggag | tgaaaacaac | tcatcagttt | 420 |
| ccatatgtca | ttttctgtgc | tccaccctcc | cgcacctcag | actaccctgc | ggatgttagg | 480 |
| ttggctgcat | caaactggag | tggtgaaggt | tctttcctat | tcacatctag | ttctgcacca | 540 |
| tttgattgca | atgacaatgg | atcatgtgat | gaggatggtc | ctgtagtgcc | aattgggagg | 600 |
| agtcctagaa | cagatgtcct | tctaaatgca | gaaaaggag | tactggagtt | tggtggatgt | 660 |
| gttcttagat | tggcaggact | ttacaaagca | gatagaggtg | cacatgttta | ttggttgaag | 720 |
| aaagggactg | ttgaagcccg | ccctgatcac | atcctcaatc | ttatacacta | tgaggatgca | 780 |
| gcttctctag | cagttgcaat | tttgaagaag | aaacggcatg | gtcagatttt | cttgggttgt | 840 |
| gataatcatc | ccgtatccag | gcaggaatta | atggacttgg | ttaataaaag | cgggaaattc | 900 |
| agtaaaaagt | ttgaggcttt | tacaggaact | agtgatcctt | gggtaagag | attaaacaac | 960 |
| tcaaaaactc | gtgaggaaat | aggatggcag | cctaaatacc | caagcttctc | gcagttcctt | 1020 |
| gagagtatct | gagtaactgc | tgcttctatt | ttgtctttgg | atttaatcca | agtacggtgc | 1080 |
| aaaaagcaca | tggattgctt | gaagatggag | ttgctgacct | ttcttttctt | ggcttacatg | 1140 |
| gcaaaatcct | gctgcaacta | aaaatttgtc | aatagtcaac | atgtaaatgt | gatcacaagt | 1200 |
| tacctagtga | aaaaatatct | tttggcacac | atataattgt | cccatggaca | tttgcttgag | 1260 |
| ttcataattc | ttaccttgtc | tactatacgc | ttta | | | 1294 |

<210> SEQ ID NO 24
<211> LENGTH: 1214
<212> TYPE: DNA
<213> ORGANISM: Populus trichocarpa

<400> SEQUENCE: 24

| | | | | | |
|---|---|---|---|---|---|
| ctaacgttat | cttcaatggc | agcacctctt | caagtctcag | cgttctctac | tattggtgca | 60 |
| agaaatgagg | agttggggac | cgcaagttct | ggtcttgttg | gggagaatga | tttgctgatt | 120 |
| gttggtcctg | gtgttcttgg | tcgcttagtc | gctgagaaat | ggcgccagga | acatccgggt | 180 |
| tgtcaagttt | atggccagac | ggtgactaca | gatcaccatg | atgaattgat | taaaatgggt | 240 |
| atcaatccat | ctttgaaagg | gactaaagca | acacagcagt | atccttatgt | cattttctgt | 300 |
| gctccgcctt | ctcgaacttc | ggattaccct | ggtgatgtaa | gagaagctgc | cttgagctgg | 360 |
| aatggggatg | gttcttttcgt | gtttacatca | agctctgcac | cgtatgattg | ttttgacaat | 420 |
| ggacagtgca | atgaggactc | tccggtagtg | cccattggga | aagccccag | aacagatgtc | 480 |
| cttctgaaag | cagaaaaagt | ggtgctggag | agtggtggtt | gtgctattag | attggcagga | 540 |
| ctttatatat | ccttctcagt | ccttaattat | gtggatttca | taaacaatag | aggtgcgcat | 600 |
| gcttactggt | tggagaaggg | tactgttgaa | gttcgtccag | atcacatcct | gaatcttatt | 660 |

```
cactatgagg atgctgcttc ccttgctgtt gcaatcttga agaagaaact tcggagccgg    720
attttcttgg gttgtgacaa ccatccatta tctaggcaag aagttatgga cttggtcgct    780
aaaagcggga agtttagcaa aaagtttgtg gcctttacag ggacaagtga tcctttaggc    840
aagagattaa acaactctaa gactcgcgag gagataggct gggagccaga ataccctagc    900
ttcgctcatt ttcttggtgt ctcaaaatag atgctatgcc tgtcagcagt aatgtgatgg    960
catagagctg acgggaagtc cacggttgtg acggaaagga tgcttggtgc tggggcagct   1020
gatttctacg tacctcacat ttgaaggcaa caaaccacct ccattttcac tattttttggt   1080 tagcagctgc aatgagaacc ggaaacctga acatgtattt gatactactc tttatgaata   1140
acaagtcttt agaaacgttt agattgtgtc tttgatctct tgtcttgcaa ataaaataca   1200
ctttcatttg attc                                                     1214

<210> SEQ ID NO 25
<211> LENGTH: 1305
<212> TYPE: DNA
<213> ORGANISM: Arabidopsis thaliana

<400> SEQUENCE: 25
tctttcccca cgccaactca atcttttccg tcgtcaaaag ccaaagctttt ttgcttttttt     60 gtcttaatgg gtttcatctc ttgcatctca tttccgacga tcaattcaag aattctatcg    120
actcaccact tttccaagca ctcgacttca gcgtcttctt catattcact taagtttgct    180
ttgagacgtc aggaggataa acccaaagtc tcgttttttc ttccattaac gtcttcgtta    240
atggcgaccc ctattcaagc ctcttcttcc tccaccattg gtgagaccag tgatggcttg    300
aaggtccagt ctcatgtttc aattggagca aacgatctgc tgattgttgg accgggtgtt    360
cttggacgct tagttgcaga acagtggaga caggaacatc cagagtctca aatctttggg    420
cagacagtaa caacaaatca tcatggtgag ttggagaatt tgggtatcaa accatctctt    480
aaaggaaccg aatatggggg aaagttctcc tatgtgatct tttgtgctcc accatcacaa    540
agcgctgatt atgctggtga agtcaggaat gcagcatcaa actggaatgg cgaaggatca    600
ttcttattca catctagttc tgcaccttat gattgctttg ataacggaga atgcaacgag    660
gattctccag tagtgccact gggaaagagt ccaagaactg atgtgctttt gaaagctgaa    720
aaagtagtgt tggaatgtgg agggactgtc cttagactag cagggcttta cacagaaact    780
agaggtgcac atacttactg gttgagtaag gagacaattg atgctcgtcc tgatcatatt    840
ctaaatctca tacactatga ggatgcagca tcgctggcag ttgcaatcat gaagaagaaa    900
gccggtgctc ggattttctt gggttgtgac aaccatcctt tgtcaaggca agaggtgatg    960
gacctgatgg ctcaaagcgg aaaattttgat aagaagttca aaggtttttac aagcaccagt   1020 ggtcctttag ggaagaagct gaacaactct aagacacgag cggagatagg atgggagccg   1080
aagtatccaa gctttgccca ttttttttgga gtatcgacat aatattttta cttggattga   1140
ttaagaatgt ctctagcgct gaagaatcca ataatgtgaa gcattattta tgtttggtac   1200
aaacaaactc atgtatcctc ttgagtgatc aaacagctga aattttcaga attcttcata   1260
aagctccatg gttcatatat ataaatcata ttttgttaat ttact                   1305

<210> SEQ ID NO 26
<211> LENGTH: 864
<212> TYPE: DNA
<213> ORGANISM: Ricinus communis
```

<400> SEQUENCE: 26

```
atggctaacc cttttcaagt ttctgcttct tctacaatgg gtgcaacgaa tgaggaattg      60
gatgctgttt cttctagtct tgttggagag aatgatcttt tgattgttgg tcctggtgtt     120
cttggccgtt tagtagctga gaaatggcgt caagaacatc ctggttgtca agtttatggg     180
cagacattga ctacagatca ccatgacgag ttgatcaaaa tagggatcaa tccatctttg     240
aagggaacta aaccaattca tcagtttcct tatgtcatat tctgtgctcc tccctcgcga     300
acatctgact accctggtga tgtcagggaa gctgctttaa gctggaatgg agaaggttct     360
ttcttattta catcgagctc tgcaccatat gactgctatg acaacggaga ttgtgatgag     420
gactctccag tagtgccaat tgggcgaagc ccgaggacag acgtgcttct aaaggcagaa     480
aaagtagtgc tggagagtga tggctgtgtc tacaaagcag atagaggtgc acatgtttat     540
tggttgcaga aggggattgt agaagttcgt cctgatcaca tcttaaatct tatacactat     600
gaggatgcag cttctctctc cattgcaatc ttgaagaaga aattccatgg gcgaattttt     660
ttgggttgtg ataatcatcc attatccagg caggaagtga tggacttggt tgctaaaagt     720
gggaaattta gtaaaaagtt tgaggccttt actggaaccg tgatccttc aggcaagaga      780
ttgaacaact cgaaaactcg agaggaagta ggatgggagc caaattaccc tagctttgct     840
cattttcttg gggtgtctga ctaa                                            864
```

<210> SEQ ID NO 27
<211> LENGTH: 1225
<212> TYPE: DNA
<213> ORGANISM: Physcomitrella patens

<400> SEQUENCE: 27

```
agagcttggc gtagcgtcgt cggccatttt ggagtttctt accacgatct ctcactattt      60
gcagcggcgt cgcagctcgt tcaatcgatc gtgatttcgt tgccgagatt atcgtttgct     120
aggttgcgtt cagacgcgtc aggtgcggag cgaaaatgtc ggggaaggaa acggagttag     180
agtgtaacga agaaaggagt caaattacga ccaactccca tgctgatttg ctggttgttg     240
gacctggagt gcttggtagt cttgtaggcc gacgttggtt agagctgcat gaagggtgta     300
gagttgtggg acagacgaat accaccaacc gacatgaaga attgctgtcg ctcggcattt     360
ttccagtcac aaaggattct cattctggag acaaatttcc ttatgtgata ttctgcgctc     420
caccgtctgg tagtgagaat tacgcagcag aagtcagggc agcagctcag aggtggaatg     480
gggaggggtc attgttattc acatctagca gtttttgttta tgacgttcat gacaatggcc     540
attgtgatga gagtgcgccc ataactgaga aaggaacgag ccctcgtggg gatagattgc     600
tgaatgcgga ggaggaggtt ttgaaggtcg atggaaacgt tgtacgattg gcaggcctat     660
atgctcggga tcgtggagcg cacatgtact ggcttcaaaa aggaacagta gatgccaggc     720
ccgaccattt tttgaatctt attcattatg gggactcggc tgatttgtgc atcgaaattt     780
tgcggaaaaa tctacgtggt caaatcttca tgggttgtga taacacacct gtttctaggc     840
aggacattat ggacatcatg atgcacagtg gtaaatttgc aggaaatttc catggattca     900
ctaaaagtga tggtcctctc gggaaaaaga tgaataacag tcaaactagg gaaagacttg     960
ggtggcaacc aaagtacaat agcttcaagg attacgttag caccttgtga ggatgcggtc    1020
tgttatctca ttgtcgtcga ctttcattct gtagacattt taagacaatt ttctgcccta    1080
tttccgcatg gtgacttcgt taacctcatc acttggagaa ttttttgtagc atcttagaca    1140
gtgaattgat ttatcttatt tcatgtgtca tgggtgaatg tttttaaccat gccatgtcca    1200
```

```
gtttgtggta acgagcagt tattc                                          1225

<210> SEQ ID NO 28
<211> LENGTH: 1068
<212> TYPE: DNA
<213> ORGANISM: Ostreococcus tauri

<400> SEQUENCE: 28
atgtcgcacg ccttaatgag cgcccgcgcg cacgttacga acgtcatcca aacctcttcg     60
cgcattcgta agcgctcgtg cacttcaaag cactttccga gtttcagggc ggcggcggcg    120
gcgtcgacat cttccgccgt gtgcgcgtcg ttcacccctc cgggcgctcg cgagcacgac    180
cgggacttgc tcatcgtcgg tccaggggtt ctaggttcgc gaatcgcgag ggtatggttg    240
gagaagtacc caggggcggt cgttgtcggg cagacgaaca cgacgaacgc gcacgccggg    300
ttgacgtcca tcggggtgtc gcctcggacg aaggatttcg acgacgacga gccgagtgcg    360
aacaggatgt tcccgtacgt tattttcagc gcaccgccga gcgggagcga cgattacgcg    420
ggtgaggtag aggcggcgct gaggtattgg aacggcggag gggcgtttgc gtttacgagc    480
tcgagcgcgg tgtacaaaaa cgagagcggg gacgcgtgcg atgaggatag cgaaacgtac    540
gatttaggaa cgaacccgcg agtcgatcgc ttgctcaagg cagagcgcat cgttctcgac    600
gcgggcgggg ttgtttgccg attggccggt ctgtaccact cggaccgcgg ggcgcacaag    660
tacttcatca agacgccttc gatcgactct cgcgccgacg cgttggtgaa cttgatccac    720
tacgaggacg ccgccgatct gtgcgtcgcc gcgatgaaca acgggtcgaa gtctgcggtg    780
tacctcggta cggatggggt tccgatcacg cgaggcgata tcgctcgcgt cgccgtcgag    840
agcggcgcgt acggcgccga cgcgcgcgcg ccgtcgttca ccaaaaccga gggcccgatc    900
ggtcgcgtca tgtccaacga ccgaacgcga acggcgctcg gttgggcacc taaatacgtc    960
tctttcgaga cctttatgac gcgcgtcaac gctcgcgacg cgtactcggc gtcggagaag   1020
cgacccgtcg ggtgggcgcc aaagggcagc gcccacatcg cgacgtga                1068

<210> SEQ ID NO 29
<211> LENGTH: 1035
<212> TYPE: DNA
<213> ORGANISM: Ostreococcus tauri

<400> SEQUENCE: 29
atgcgcgctt cgagcgcgtc accgcgcgcg caccgcgcgt ttccctcgca caccgcgcga     60
aagacgtcgc gcgaaaaagc gtcgtctcgg tctcgcgcgg tggcggcggc gtcgacttcg    120
gacgcaccgg ggccgttcgg ggacgaccga aacctgctcg tcgtcggacc cggtgttttg    180
ggctcgcgca tcgcgcgcgt gtggctgtcg aacttccccg gggcggtggt ggtcggacag    240
acgaacaccg acgccgcgca cgacggcttg cgaagcgtcg gcgtgacgcc gcgaacgaag    300
gatttcggtg cggacgatcc cacggcgacg cggcggtttc cctacgtcgt tttcagcgcg    360
ccaccgagtg gcagtgagga ttacccgggc gaagtcgcgg cggcgttgaa gtattgggac    420
ggctcgggcg cgttcgcgtt tacgagctcg agcgccgtgt acaagaatga agccggcgag    480
gcgtgcgacg aggagagtga agtttatgaa ataggcacca atcctcgtgt cgatcggttg    540
ctgaaggcgg aaaaagtcgt gttagacgct ggtggtgtgg tgtgtcgatt agccgggctc    600
tatcactccg agcgaggcgc gcacaagtac ttcatcaaga cgtcctcgct cgattctcgc    660
gccgacgcct tggtgaattt aattcactac gaagacgccg ccgatctgtg cttcgccgcg    720
```

| | |
|---|---|
| atgacgaaag gagcaaagtc tcacatttat ctcggcaccg acggcgtccc gatcacccgc | 780 |
| gaggcgatcg cgcgcgtctc cgtggagtct ggcgtctacg gcgccgacgc cgccgcgccc | 840 |
| gccttcacca aaaccgacgg cccgctcggt cgcgccatgt ccaactcccg caccaagacc | 900 |
| gagctcgatt ggtcgcctcg gtacgaatct ttcgaatctt tcgcgttgcg tcagggcgcg | 960 |
| cgcgactcgt acgcgccctg gaacgcgccg acgcgttcgc gcgggtggac ccccgcgggc | 1020 |
| gcgcgtcacg tgtga | 1035 |

<210> SEQ ID NO 30
<211> LENGTH: 885
<212> TYPE: DNA
<213> ORGANISM: Micromonas pusilla

<400> SEQUENCE: 30

| | |
|---|---|
| atggcggcgg tatccgagag ctgctgtcgc gatctcctcg tcgtaggccc cggagttctc | 60 |
| ggcagtctcg tgtgccaacg atggctcaag acgttccccg cggcgacggt gatcggccag | 120 |
| acgaacacgg acgcgtcgca cgagcggttg gtcgccctcg gaatctcgcc gcgtttgaaa | 180 |
| gcggacgcgg gggagtctcg ccgattcccg ttcgtcgtct tcagcgcgcc gccgtccgga | 240 |
| agcgacgact acaccgccga ggtcgaagcc gcgctgaagc tgtgggacgg caccggtgga | 300 |
| ttcgtgttca cgagcagcac cgcggtgtac gcgggtaaag acggcgagga ctgcgacgag | 360 |
| accacggcgc agttccaaat cggtgagtcc ccgaggggcgg acaagttgct gaacgcggaa | 420 |
| gccgcggttc tgggcgccgg cgggtgcgtc gtgcgcctgt ccggtctgta tcactcccaa | 480 |
| cgcggggcac acatgtactt tttgaagacc ccgacgttgg cgtccagacc cgacgcgctg | 540 |
| gtgaacctcg tgcactacga agacgccgcg gccgcttgcg tgcgcgcgtt atccgcgcag | 600 |
| ctcgagggca gctcggaggg tggcgagata ttcctcgcca cggacggcgt gcccgttacg | 660 |
| cgagagaaga tggtcgaggc gtgtctggcg tgccccgacg cgtacgacga cggagcgatg | 720 |
| ccggagttta gcgtgagcga cgggccgctc gggaagagca tgacgaatcc gcaaacgcgc | 780 |
| gagaagctcg gctgggagcc ggtgtatccg agcttcgtcg agttcgtcgc tgcgggcgcg | 840 |
| aaagactcgt tctatcctcc gaagaagaag aacacgtgga gttag | 885 |

<210> SEQ ID NO 31
<211> LENGTH: 882
<212> TYPE: DNA
<213> ORGANISM: Micromonas pusilla

<400> SEQUENCE: 31

| | |
|---|---|
| atgtcgagct gcactttcgc cactccacgt gtcgaagtga ttaggtcgcg gggatctcct | 60 |
| ctcagcgcga gagccgcgcg ctcctcctcc tcgtccaaat ttccggcggc ttccgtgatc | 120 |
| ggtcagacaa ataccgacac ttcgcacgag aggctgctct ccctcggcgt gtttccccgg | 180 |
| ctgaaggaaa aggctgggga tgagcagtac cctttcgtcg tgttcagcgc gccgccttct | 240 |
| ggcagcgagg actacgccgc cgaggtcgag gcagccctga gtactgggga tggcagcggc | 300 |
| gcttttgtct tcaccagcag cacggcggtg tatgccggca aggacggaga gccttgcgat | 360 |
| gagagcacgc ctcagtttga gattgggag tcacctcgcg cggataggct gctgaaggcc | 420 |
| gaggcggcgg tgctggccgc gggtgggagc gtcgttcgtc tcgcgggact gtatcactca | 480 |
| cagcggggtg ctcacatgta ctttctgaaa accccctctc ttgcatccaa cgctgacggt | 540 |
| ctggtcaacc tgattcacta cgaggacgcg gcggcggcgt gtgtcgacgt gctcgttgcg | 600 |
| cagtttgagg gaaggacagg cggaggggag gttttcctgg ccacagacgg cgtgcccgtt | 660 |

```
accaggaagg aaatggtcga gtgctgcttg gagagcgatg cctacgacgg aaacatgccg      720
gaattcacgg aggacaatgg accctgggt aagagcatga caaccctca aactcgtgag       780 aaactcggct gggttccggt gcacgcgagc ttcgtcgagt ttgtcgaggc gggtgcgacg      840
gattcattct atcccaagcg caggaagagc acttggaagt ag                        882
```

<210> SEQ ID NO 32
<211> LENGTH: 1578
<212> TYPE: DNA
<213> ORGANISM: Chlamydomonas reinhardtii

<400> SEQUENCE: 32

```
agctgctcgt aatatctggg atcttgtgga gaggccagct cgggtcggtt ggagacgaca      60
tcatgtcgcc ccggagctgc ttgagcgctt cgcccaccag ctctgtcgct actcgcacta     120
cattcacatc tacctgtatt cctcgtcccc gagcggcggg agtccaagtc tcggcgcaac     180
tgaacatttc gcgtcgcagc gctagcgccg ctgctatcgc tagcgttgca ccgctgggga     240
tgaccttttc tggatcaatc gacggtggtg ccgcacgcgg ctctgtcgca gctgctgcaa     300
ccagctctct ggcgggagca gtggcggggt cgccgtccaa tctggaccta ctggtggtgg     360
ggccgggtgt gttgggcagc gtcctgggcc gcgactggct ggcgtctgtg cagggcggca     420
cagccaccgg cctcaccaac acggatcgca gccacgagcg gctgcgcgcc atggggctga     480
cgccggccac acgttccacc ctaccgccca acaagaaata cagcttcgtg gccttcgccg     540
cgccgccctc aggcagtgag gattacgttg ctgatatcaa gtcggctctg cattgtgggg     600
acggcagtgg ctcattcatc ttcacgtcgt ccatgtcggt gtgcgcagtg gacgacggtg     660
gctccgctac cgacgagcac tgcccgctgg tgcccgtggg cgcggggccc tccactgaca     720
agctgcgcgg ggcggaggag gctgtcctgg cggccggtgg caacgtgcta cgcctggtgg     780
gtctgtacca caagtttcgc ggcgcacaca ccttctttat caaacagggc actgtggccc     840 ggccagggggg ctatgtggtg aacctgctgc actacgagga cgctgcggca ctggctgcag     900
cgatcctgcg tggtgatggc tctgggcct tccgaggccg tgcgttcctg gcactgatg     960 gccacccagt aacgtttgag gacatggtgg agtactgctt tgctggtggt gcctttgagc    1020
gcgtaccagt gtcgttcacc ggcaccttcc ctgacggtgg caagaccggt cggggcaagc    1080
gtgtagacaa cagcggaaca agccaggcgc taggtggctg gaagcccaag tacgagtcat    1140
tccagtcctt tatggctgct ggcggggctg actactacaa cacttcgggg ctaaagtgga    1200
actaaagtgg gagtgtaagc caggtgcaca cgatgggtga actgttagac ttgcgacaag    1260
cgtgtgggct tgaggcaatg ccacacgact gcagtggtgt tggcacaaga caggagcacg    1320
gaaatcgtgg gagtgcaggg ggcagacttg tgtcagcag tagcagccac agaggttatg    1380 tcgaagggg tgctagcgaa ctgaagatag agggcttcat tagttgcgca actgtggcac    1440
aggcaggcca ggcagaaggc atgactggtg ctagggtggc tgagagcacg ttgggaacaa    1500
ccgttccctg gcttcgcaac cttcccctgg cttgacgtgc agtcacgaag ggcactgtaa    1560
gcacgtttga gtgtgtga                                                  1578
```

<210> SEQ ID NO 33
<211> LENGTH: 952
<212> TYPE: DNA
<213> ORGANISM: Phaeodactylum tricornutum

<400> SEQUENCE: 33

```
tcttcgactc ataaaatcgt ccatcgtttc tgtatcgatt gcacttgctt ctattttagc      60
atcggctttg gccatggcga cgaagacatc atcgggtgt gctgtcatcg gagttggcgt       120
tctaggtacc agtttatgcc aacagatctt gtctgcgcct gagtttgatg gaatcaagct      180
tacaggcatt acaaaaacta ccaccaatca caacgcgatc cgagaaaaag tcggaatgga      240
tagcgaagat cgtttccagc tattgaccac agatgaatgt gaaggaacgg aaaccaaatt      300
caagcatatc gtgttttgtg cgccgccttc gggttctgaa gactacccag ccgacgtacg      360
gaaatccgcc gatacgctat gggcaggacc ggaagaaggg ggcgttttcg tgtttacctc      420
cagcggtgca gtatacggac ctggggattc tagaacagta tcagaaacat ccgatattgc      480
tgatcctgaa tcgagtgtac gagtcggacg cctcgtgaag gccgaaaagg ctgctctaga      540
cgctggcgga tgcgtgttgc ggttggctgg tctctacaat ttagatcgcg gcgctcacaa      600 ttttggttg accagcggga agccaatatc cgggctaccc gaaggcatca tcaatctact        660
gcattacgag gatgccgcaa gtgcctgtct atcggcgctc aaagctggct ccagcgtctg      720
cgaaggtcga gcctttataa tcagtgatgg tcatcctctc acacgaaaac aaatctgcga      780
aagcgcgctg caagcaaaaa cctataaaga ttgtgcaatg cctacatttg catccgaaaa      840
tttgaatggc atggccttgg ggaaggtgta cgatggatcc tcaagtaaca aggcgttaga      900
gtggtctccg cgctttgaat cctttgacac atttatgaac agcatggcct aa              952

<210> SEQ ID NO 34
<211> LENGTH: 825
<212> TYPE: DNA
<213> ORGANISM: Thalassiosira pseudonana

<400> SEQUENCE: 34
atggcggtgc tctccctcct aaccgctctc ctcgtgctct caccagcacg agctttctcc      60
acgccccaac ccatcacttc cgacctagcc attgtaggat gtggcgtcct cggcacatcg      120
ctatgcaaac aactgctatc acatcctgac ttttcatctc ggtccatcac ggccattacc      180
aagaccactg gtcgtcatga tgccattcgt gccgaggttg gagacggcga tgacacggat      240
agattcgcag tgctgacaat ggatgatgtg ttggctcaat acagtggaaa ttccttcaag      300
gatgttgtat tttgtgcacc gccatcgggt tttgacgact atccccaggc agtcaaagat      360
gcagcgacac agttgtggtc ggggccttcg tccggtgggg cgttcgtatt cacttccagt      420
ggtggagtgt atgaagggtt agatggggag actgtgaatg aatcatcgcc tacgttggat      480
gcagaggcaa atccaagaca ggggaggtta atcaacgcgg aacgtgaatg tattgcgttg      540 gggggtgtg cactacgttt ggctgggctg tatactttgg aaagagggc acacaactac        600 tggcttgaaa aatgtaccga gggagttcaa gggagagaag acggtattgt gaacctattg      660
cattacgatg acgctgcgtc ggcgtgtctc gccgcgttgc aggtggggcc tgatgtgaac      720
tccaaacaga cgtacttgat tagtgacggg aatccaacta cgcgaaaggg gatctgcgag      780
agtgccttga agagtgcaag atggtttgaa ggggaaaatt tatga                      825

<210> SEQ ID NO 35
<211> LENGTH: 21
<212> TYPE: DNA
<213> ORGANISM: Synthetic

<400> SEQUENCE: 35
gtcgtgccat gacatctacc a                                                21
```

```
<210> SEQ ID NO 36
<211> LENGTH: 21
<212> TYPE: DNA
<213> ORGANISM: Synthetic

<400> SEQUENCE: 36
ctgctttatt gcctcacttg c                                              21

<210> SEQ ID NO 37
<211> LENGTH: 20
<212> TYPE: DNA
<213> ORGANISM: Synthetic

<400> SEQUENCE: 37
cgtcgtgctt cctgactcca                                                20

<210> SEQ ID NO 38
<211> LENGTH: 21
<212> TYPE: DNA
<213> ORGANISM: Synthetic

<400> SEQUENCE: 38
cctccaccaa catgctcctt c                                              21

<210> SEQ ID NO 39
<211> LENGTH: 24
<212> TYPE: DNA
<213> ORGANISM: Synthetic

<400> SEQUENCE: 39
acataaccta ccgaagaaga gtgg                                           24

<210> SEQ ID NO 40
<211> LENGTH: 22
<212> TYPE: DNA
<213> ORGANISM: Synthetic

<400> SEQUENCE: 40
tcacagcctg aagcacataa aa                                             22

<210> SEQ ID NO 41
<211> LENGTH: 21
<212> TYPE: DNA
<213> ORGANISM: Synthetic

<400> SEQUENCE: 41
ggatacggca ctggatcttg g                                              21

<210> SEQ ID NO 42
<211> LENGTH: 21
<212> TYPE: DNA
<213> ORGANISM: Synthetic

<400> SEQUENCE: 42
ttgaatggag ggtcgttgag c                                              21

<210> SEQ ID NO 43
<211> LENGTH: 22
<212> TYPE: DNA
<213> ORGANISM: Synthetic

<400> SEQUENCE: 43
tactgctccg atacttcaac cc                                             22
```

<210> SEQ ID NO 44
<211> LENGTH: 22
<212> TYPE: DNA
<213> ORGANISM: Synthetic

<400> SEQUENCE: 44
ccatccgcta gatcaacaac at                                            22

<210> SEQ ID NO 45
<211> LENGTH: 20
<212> TYPE: DNA
<213> ORGANISM: Synthetic

<400> SEQUENCE: 45
ccaagacgcc ctggtgatgc                                               20

<210> SEQ ID NO 46
<211> LENGTH: 24
<212> TYPE: DNA
<213> ORGANISM: Synthetic

<400> SEQUENCE: 46
ttcgctttcc agttgagttc cttc                                          24

<210> SEQ ID NO 47
<211> LENGTH: 21
<212> TYPE: DNA
<213> ORGANISM: Synthetic

<400> SEQUENCE: 47
tcgctactcc tgacattggt t                                             21

<210> SEQ ID NO 48
<211> LENGTH: 20
<212> TYPE: DNA
<213> ORGANISM: Synthetic

<400> SEQUENCE: 48
tgatcgccct aattctgctc                                               20

<210> SEQ ID NO 49
<211> LENGTH: 21
<212> TYPE: DNA
<213> ORGANISM: Synthetic

<400> SEQUENCE: 49
tggaacagga aagggaacat c                                             21

<210> SEQ ID NO 50
<211> LENGTH: 21
<212> TYPE: DNA
<213> ORGANISM: Synthetic

<400> SEQUENCE: 50
tcgtggacca ataaccaaag g                                             21

<210> SEQ ID NO 51
<211> LENGTH: 21
<212> TYPE: DNA
<213> ORGANISM: Synthetic

<400> SEQUENCE: 51
gccagaacaa acccatcaaa c                                             21

```
<210> SEQ ID NO 52
<211> LENGTH: 21
<212> TYPE: DNA
<213> ORGANISM: Synthetic

<400> SEQUENCE: 52
gtaactccag agccgaacca g                                             21

<210> SEQ ID NO 53
<211> LENGTH: 20
<212> TYPE: DNA
<213> ORGANISM: Synthetic

<400> SEQUENCE: 53
ataatctccg atggctgttc                                               20

<210> SEQ ID NO 54
<211> LENGTH: 22
<212> TYPE: DNA
<213> ORGANISM: Synthetic

<400> SEQUENCE: 54
tccagacctt atgtagtatc cc                                            22

<210> SEQ ID NO 55
<211> LENGTH: 19
<212> TYPE: DNA
<213> ORGANISM: Synthetic

<400> SEQUENCE: 55
gggccttcat ggatcaacc                                                19

<210> SEQ ID NO 56
<211> LENGTH: 20
<212> TYPE: DNA
<213> ORGANISM: Synthetic

<400> SEQUENCE: 56
ccgcttcaag catcctcatc                                               20

<210> SEQ ID NO 57
<211> LENGTH: 20
<212> TYPE: DNA
<213> ORGANISM: Synthetic

<400> SEQUENCE: 57
gcctgccctg gactacattg                                               20

<210> SEQ ID NO 58
<211> LENGTH: 24
<212> TYPE: DNA
<213> ORGANISM: Synthetic

<400> SEQUENCE: 58
gcaaacatat gtacacggtt ctgg                                          24

<210> SEQ ID NO 59
<211> LENGTH: 19
<212> TYPE: DNA
<213> ORGANISM: Synthetic

<400> SEQUENCE: 59
```
aacgtggctg ctccttgaa                                                19

<210> SEQ ID NO 60
<211> LENGTH: 20
<212> TYPE: DNA
<213> ORGANISM: Synthetic

<400> SEQUENCE: 60
ttggcaataa gccacacaca                                               20

<210> SEQ ID NO 61
<211> LENGTH: 19
<212> TYPE: DNA
<213> ORGANISM: Synthetic

<400> SEQUENCE: 61
tggccatgga agagttggc                                                19

<210> SEQ ID NO 62
<211> LENGTH: 19
<212> TYPE: DNA
<213> ORGANISM: Synthetic

<400> SEQUENCE: 62
cagaagcaac tgctccacc                                                19

<210> SEQ ID NO 63
<211> LENGTH: 20
<212> TYPE: DNA
<213> ORGANISM: Synthetic

<400> SEQUENCE: 63
gaagtccttg agccgtcctg                                               20

<210> SEQ ID NO 64
<211> LENGTH: 20
<212> TYPE: DNA
<213> ORGANISM: Synthetic

<400> SEQUENCE: 64
aagtcccttg atgccctcct                                               20

<210> SEQ ID NO 65
<211> LENGTH: 21
<212> TYPE: DNA
<213> ORGANISM: Synthetic

<400> SEQUENCE: 65
agaagggatc cagatgaaga a                                             21

<210> SEQ ID NO 66
<211> LENGTH: 22
<212> TYPE: DNA
<213> ORGANISM: Synthetic

<400> SEQUENCE: 66
aacaagaaac gagcaacata ga                                            22

<210> SEQ ID NO 67
<211> LENGTH: 20
<212> TYPE: DNA
<213> ORGANISM: Synthetic

<400> SEQUENCE: 67
gcctccatca tcatcttcca                                              20

<210> SEQ ID NO 68
<211> LENGTH: 20
<212> TYPE: DNA
<213> ORGANISM: Synthetic

<400> SEQUENCE: 68
attgttacat cccgagcacc                                              20

<210> SEQ ID NO 69
<211> LENGTH: 21
<212> TYPE: DNA
<213> ORGANISM: Synthetic

<400> SEQUENCE: 69
gccagaacaa acccatcaaa c                                            21

<210> SEQ ID NO 70
<211> LENGTH: 21
<212> TYPE: DNA
<213> ORGANISM: Synthetic

<400> SEQUENCE: 70
gtaactccag agccgaacca g                                            21

<210> SEQ ID NO 71
<211> LENGTH: 20
<212> TYPE: DNA
<213> ORGANISM: Synthetic

<400> SEQUENCE: 71
gcttccacat tgacccatac                                              20

<210> SEQ ID NO 72
<211> LENGTH: 20
<212> TYPE: DNA
<213> ORGANISM: Synthetic

<400> SEQUENCE: 72
cttgagggca tacagcatct                                              20

<210> SEQ ID NO 73
<211> LENGTH: 20
<212> TYPE: DNA
<213> ORGANISM: Synthetic

<400> SEQUENCE: 73
cacgacgcag tgatctgagg                                              20

<210> SEQ ID NO 74
<211> LENGTH: 20
<212> TYPE: DNA
<213> ORGANISM: Synthetic

<400> SEQUENCE: 74
gatgaaacgc agggaatacg                                              20

<210> SEQ ID NO 75
<211> LENGTH: 19
<212> TYPE: DNA
<213> ORGANISM: Synthetic

```
<400> SEQUENCE: 75
gacatcgtca agagggtcg                                                19

<210> SEQ ID NO 76
<211> LENGTH: 20
<212> TYPE: DNA
<213> ORGANISM: Synthetic

<400> SEQUENCE: 76
ccatccatga tccatcatcc                                               20
```

PLASTIDIAL NUCLEOTIDE SUGAR EPIMERASES

CROSS-REFERENCE

Figure 1:
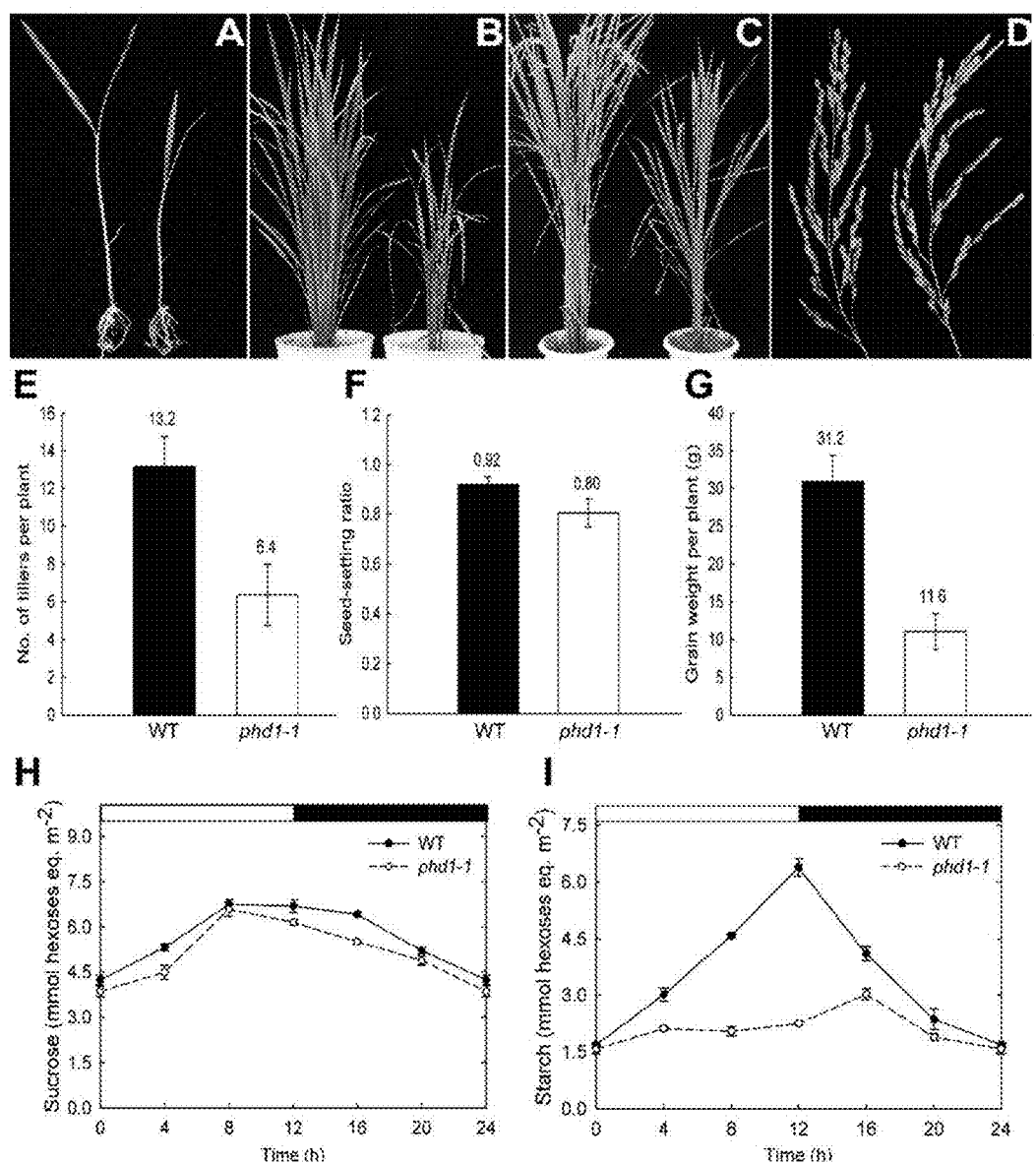

This utility application is a national phase application of application of PCT/CN2011/000852 filed May 16, 2011, which claims priority to CN patent application 201010178405.6 which was filed May 17, 2010, both of which are incorporated herein by reference.

FIELD

The field relates to plant breeding and genetics and, in particular, relates to recombinant DNA constructs useful in plants for conferring tolerance to drought and increase in yield.

BACKGROUND

Abiotic stress is the primary cause of crop loss worldwide, causing average yield losses of more than 50% for major crops (Boyer, J. S. (1982) Science 218:443-448; Bray, E. A. et al. (2000) In Biochemistry and Molecular Biology of Plants, Edited by Buchannan, B. B. et al., Amer. Soc. Plant Biol., pp. 1158-1249). Among the various abiotic stresses, drought is a major factor that limits crop yield worldwide. Exposure of plants to a water-limiting environment during various developmental stages appears to activate various physiological and developmental changes. Understanding of the basic biochemical and molecular mechanism for drought stress perception, transduction and tolerance is a major challenge in biology.

Photosynthetic reactions in higher plants depend on chloroplast thylakoid membrane system. Chloroplast thylakoid assembly and maintenance require a continuous supply of membrane constituents. Galactose-containing glycerolipids are predominant lipid components of photosynthetic membranes in plants, algae, and cyanobacteria. The two most common galactolipids are mono- and digalactosyldiacylglycerol (MGDG and DGDG), which account for about 50 and 25 mol % of total thylakoid lipids, respectively. About 80% of all plant lipids are associated with photosynthetic membranes, and MGDG is considered to be the most abundant membrane lipid on earth. Galactolipids play an important role in the organization of photosynthetic membranes and in their photosynthetic activities.

In plants, MGDG is synthesized in two unique steps: (i) the conversion of UDP-D-glucose (UDP-Glc) into UDP-D-galactose (UDP-Gal) by an UDP-glucose 4-epimerase (UGE), and (ii) the transfer of a galactosyl residue from UDP-Gal to diacylglycerol (DAG) for synthesis of the final product by MGDG synthase (MGD1). MGD1 is localized in the inner chloroplast envelope membrane and uses UDP-Gal as a substrate.

Plants possess a sophisticated sugar biosynthetic machinery comprising families of nucleotide sugars that can be modified at their glycosyl moieties by nucleotide sugar interconversion enzymes to generate different sugars. UDP-glucose 4-epimerase (also UDP-galactose 4-epimerase, UGE; EC 5.1.3.2) catalyzes the interconversion of UDP-Glc and UDP-Gal. UGEs identified from plants lack transmembrane motifs and signal peptides and appear to exist as soluble entities in the cytoplasm. Generally, plant UDP-Glc epimerase enzymes are localized to the cytosol, where their substrates UDP-Glc and UDP-Gal are present at high levels. As a precursor for the synthesis of the galactolipid MGDG in chloroplasts, UDP-Gal is generally thought to be mobilized from the cytosol, because the UDP-Gal concentration is relatively low within plastids and MGDG synthase (MGD1) is associated with the inner envelope membrane To gain insight into genes controlling photosynthetic activity and carbon assimilation in plants, a rice stunted growth mutant (phd1) with decreased photoassimilate and yield production was identified. A novel chloroplast-localized UDP-Glc epimerase involved in UDP-Gal supply for chloroplast galactolipid biosynthesis during photosynthetic membrane biogenesis is disclosed herein.

SUMMARY

Plastidial UDP glucose epimerase, its homologs and methods of use are disclosed. Transgenic expression of PHD1 increased photosynthetic activity and enhanced growth. Roles of PHD1, homologs, and functional fragments thereof in photosynthetic capability and carbon assimilate homeostasis are discussed herein.

The present disclosure includes:

In one embodiment, a plant comprising in its genome a recombinant DNA construct comprising a polynucleotide operably linked to at least one regulatory element, wherein said polynucleotide comprises a nucleotide sequence selected from the group consisting of: (a) a nucleotide sequence encoding a polypeptide with plastidial epimerase activity, wherein the polypeptide has an amino acid sequence of at least 60%, 80%, 85%, 90%, 95% or 100% sequence identity, based on the Clustal V method of alignment with pairwise alignment default parameters of KTUPLE=1, GAP PENALTY=3, WINDOW=5 and DIAGONALS SAVED=5, when compared to SEQ ID NO: 1-17 (b) a nucleotide sequence encoding a polypeptide with epimerase activity, wherein the nucleotide sequence is hybridizable under stringent conditions with a DNA molecule comprising the full complement of SEQ ID NO: 18-34 (c) a nucleotide sequence encoding a polypeptide with epimerase activity, wherein the nucleotide sequence is derived from SEQ ID NO: 18-34 by alteration of one or more nucleotides by at least one method selected from the group consisting of: deletion, substitution, addition and insertion; (d) a nucleotide sequence encoding a polypeptide wherein the amino acid sequence of the polypeptide comprises SEQ ID NO: 1 and (e) a nucleotide sequence comprising SEQ ID NO: 18 and wherein said plant exhibits increased drought tolerance when compared to a control plant not comprising said recombinant DNA construct. The plant may be a monocot or dicot.

In an embodiment, the PHD1 polypeptide does not have the N-terminal chloroplast transit peptide 1-62 amino acids of SEQ ID NO: 1 or the corresponding equivalent in other PHD1 homologs. For example, a nucleotide molecule substantially lacking the region encoding the chloroplast transit peptide is expressed in a plant cell, for example, in the plastids.

In an embodiment, the chloroplast transit peptide (1-62 amino acids of SEQ ID NO: 1 or a sequence that is substantially similar to the 62-amino acid N-terminal region of SEQ ID NO: 1) is fused to a heterologous peptide for transport of the expressed protein/peptide into the chloroplast.

In another embodiment, a plant comprising in its genome a recombinant DNA construct comprising a polynucleotide operably linked to at least one regulatory element, wherein said polynucleotide comprises a nucleotide sequence selected from the group consisting of: (a) a nucleotide sequence encoding a polypeptide with epimerase activity, wherein the polypeptide has an amino acid sequence of at least 60%, 80%, 85%, 90%, 95% or 100% sequence identity, based on the Clustal V method of alignment with pairwise alignment default parameters of KTUPLE=1, GAP PENALTY=3, WINDOW=5 and DIAGONALS SAVED=5, when compared to SEQ ID NO: 1-17 (b) a nucleotide sequence encoding a polypeptide with epimerase activity, wherein the nucleotide sequence is hybridizable under stringent conditions with a DNA molecule comprising the full complement of SEQ ID NO: 18-34 (c) a nucleotide sequence encoding a polypeptide with epimerase activity, wherein the nucleotide sequence is derived from SEQ ID NO: 18-34 by alteration of one or more nucleotides by at least one method selected from the group consisting of: deletion, substitution, addition and insertion; (d) a nucleotide sequence encoding a polypeptide wherein the amino acid sequence of the polypeptide comprises SEQ ID NO: 1 and (e) a nucleotide sequence comprising SEQ ID NO: 18 and wherein said plant exhibits an increase in yield when compared to a control plant not comprising said recombinant DNA construct. The plant may exhibit said increase in yield when compared, under water limiting conditions, to said control plant not comprising said recombinant DNA construct. The plant may be a monocot or dicot.

In another embodiment, a method of increasing drought tolerance in a plant, comprising: (a) introducing into a regenerable plant cell a recombinant DNA construct comprising a polynucleotide operably linked to at least one regulatory element, wherein said polynucleotide comprises a nucleotide sequence selected from the group consisting of: (i) a nucleotide sequence encoding a polypeptide with epimerase activity, wherein the polypeptide has an amino acid sequence of at least 60%, 80%, 85%, 90%, 95% or 100% sequence identity, based on the Clustal V method of alignment with pairwise alignment default parameters of KTUPLE=1, GAP PENALTY=3, WINDOW=5 and DIAGONALS SAVED=5, when compared to SEQ ID NO: 1-17 (ii) a nucleotide sequence encoding a polypeptide with epimerase activity, wherein the nucleotide sequence is hybridizable under stringent conditions with a DNA molecule comprising the full complement of SEQ ID NO: 18-34 (iii) a nucleotide sequence encoding a polypeptide with epimerase activity, wherein the nucleotide sequence is derived from SEQ ID NO: 18-34 by alteration of one or more nucleotides by at least one method selected from the group consisting of: deletion, substitution, addition and insertion; (iv) a nucleotide sequence encoding a polypeptide wherein the amino acid sequence of the polypeptide comprises SEQ ID NO: 1 and (v) a nucleotide sequence comprising SEQ ID NO: 18 and (b) regenerating a transgenic plant from the regenerable plant cell after step (a), wherein the transgenic plant comprises in its genome the recombinant DNA construct and exhibits increased drought tolerance when compared to a control plant not comprising the recombinant DNA construct. The method may further comprise: (c) obtaining a progeny plant derived from the transgenic plant, wherein said progeny plant comprises in its genome the recombinant DNA construct and exhibits increased drought tolerance when compared to a control plant not comprising the recombinant DNA construct.

In another embodiment, a method of evaluating drought tolerance in a plant, comprising: (a) obtaining a transgenic plant, wherein the transgenic plant comprises in its genome a recombinant DNA construct comprising a polynucleotide operably linked to at least one regulatory element, wherein said polynucleotide comprises a nucleotide sequence selected from the group consisting of: (i) a nucleotide sequence encoding a polypeptide with epimerase activity, wherein the polypeptide has an amino acid sequence of at least 60%, 80%, 85%, 90%, 95% or 100% sequence identity, based on the Clustal V method of alignment with pairwise alignment default parameters of KTUPLE=1, GAP PENALTY=3, WINDOW=5 and DIAGONALS SAVED=5, when compared to SEQ ID NO: 1-17 (ii) a nucleotide sequence encoding a polypeptide with epimerase activity, wherein the nucleotide sequence is hybridizable under stringent conditions with a DNA molecule comprising the full complement of SEQ ID NO: 18-34 (iii) a nucleotide sequence encoding a polypeptide with epimerase activity, wherein the nucleotide sequence is derived from SEQ ID NO: 18-34 by alteration of one or more nucleotides by at least one method selected from the group consisting of: deletion, substitution, addition and insertion; (iv) a nucleotide sequence encoding a polypeptide wherein the amino acid sequence of the polypeptide comprises SEQ ID NO: 1 and (v) a nucleotide sequence comprising SEQ ID NO: 18 and (b) obtaining a progeny plant derived from the transgenic plant of (a), wherein the progeny plant comprises in its genome the recombinant DNA construct; and (c) evaluating the progeny plant for drought tolerance compared to a control plant not comprising the recombinant DNA construct.

In another embodiment, a method of determining an alteration of an agronomic characteristic in a plant, comprising: (a) obtaining a transgenic plant, wherein the transgenic plant comprises in its genome a recombinant DNA construct comprising a polynucleotide operably linked to at least one regulatory element, wherein said polynucleotide comprises a nucleotide sequence selected from the group consisting of: (i) a nucleotide sequence encoding a polypeptide with epimerase activity, wherein the polypeptide has an amino acid sequence of at least 60%, 80%, 85%, 90%, 95% or 100% sequence identity, based on the Clustal V method of alignment with pairwise alignment default parameters of KTUPLE=1, GAP PENALTY=3, WINDOW=5 and DIAGONALS SAVED=5, when compared to SEQ ID NO: 1-17 (ii) a nucleotide sequence encoding a polypeptide with epimerase activity, wherein the nucleotide sequence is hybridizable under stringent conditions with a DNA molecule comprising the full complement of SEQ ID NO: 18-34 (iii) a nucleotide sequence encoding a polypeptide with epimerase activity, wherein the nucleotide sequence is derived from SEQ ID NO: 18-34 by alteration of one or more nucleotides by at least one method selected from the group consisting of: deletion, substitution, addition and insertion; (iv) a nucleotide sequence encoding a polypeptide wherein the amino acid sequence of the polypeptide comprises SEQ ID NO: 1 and (v) a nucleotide sequence comprising SEQ ID NO: 18 and (b) obtaining a progeny plant derived from the transgenic plant of step (a), wherein the progeny plant comprises in its genome the recombinant DNA construct; and (c) determining whether the progeny plant exhibits an alteration of at least one agronomic characteristic when compared to a control plant not comprising the recombinant DNA construct. Said determining step (c) may comprise determining whether the transgenic plant exhibits an alteration of at least one agronomic characteristic when compared, under water limiting conditions, to a control plant not comprising the recombinant DNA construct. Said at least one agronomic trait may be yield and furthermore may be an increase in yield.

In another embodiment, an isolated polynucleotide comprising a nucleotide sequence selected from the group consisting of: (a) a nucleotide sequence encoding a polypeptide with epimerase activity, wherein the polypeptide has an amino acid sequence of at least 60%, 80%, 85%, 90% or 95% sequence identity, based on the Clustal V method of alignment with pairwise alignment default parameters of KTUPLE=1, GAP PENALTY=3, WINDOW=5 and DIAGONALS SAVED=5, when compared to SEQ ID NO: 1-17 (b) a nucleotide sequence encoding a polypeptide with epimerase activity, wherein the nucleotide sequence is hybridizable under stringent conditions with a DNA molecule comprising the full complement of SEQ ID NO: 18-34 (c) a nucleotide sequence encoding a polypeptide with epimerase activity, wherein the nucleotide sequence is derived from SEQ ID NO: 18-34 by alteration of one or more nucleotides by at least one method selected from the group consisting of: deletion, substitution, addition and insertion; (d) a nucleotide sequence encoding a polypeptide wherein the amino acid sequence of the polypeptide comprises SEQ ID NO: 1 and (e) a nucleotide sequence comprising SEQ ID NO: 18.

In another embodiment, an isolated polynucleotide comprising the full complement of the nucleotide sequence of the disclosure, wherein the full complement and the nucleotide sequence of the disclosure consist of the same number of nucleotides and are 100% complementary.

In another embodiment, a recombinant DNA construct comprising the isolated polynucleotide of the disclosure operably linked to at least one regulatory element.

In another embodiment, a cell comprising the recombinant DNA construct of the disclosure, wherein the cell is selected from the group consisting of a bacterial cell, a yeast cell, and insect cell and a plant cell.

In another embodiment, a plant or a seed comprising the recombinant DNA construct of the disclosure. The plant or seed may be a monocot or a dicot plant or seed.

In another embodiment, a method for isolating a polypeptide encoded by the recombinant DNA construct of the disclosure, wherein the method comprises the following: (a) transforming a cell with the recombinant DNA construct of the disclosure; (b) growing the transformed cell of step (a) under conditions suitable for expression of the recombinant DNA construct; and (c) isolating the polypeptide from the transformed cell of step (b).

In another embodiment, a vector comprising the polynucleotide of the disclosure.

In another embodiment, a method for producing a transgenic plant comprising transforming a plant cell with the recombinant DNA construct of the disclosure and regenerating a transgenic plant from the transformed plant cell.

In another embodiment, the present disclosure includes any of the plants of the present disclosure wherein the plant is selected from the group consisting of: maize, soybean, sunflower, sorghum, canola, wheat, alfalfa, cotton, rice, barley, millet, sugarcane, switchgrass, tobacco, potato and sugar beet.

In another embodiment, the present disclosure includes any of the methods of the present disclosure wherein the plant is selected from the group consisting of: maize, soybean, sunflower, sorghum, canola, wheat, alfalfa, cotton, rice, barley, millet, sugarcane, switchgrass, tobacco, potato and sugar beet.

In another embodiment, the present disclosure includes seed of any of the plants of the present disclosure, wherein said seed comprises in its genome a recombinant DNA construct comprising a polynucleotide operably linked to at least one regulatory element, wherein said polynucleotide encodes a polypeptide having an amino acid sequence of at least 60% sequence identity, based on the Clustal V method of alignment, when compared to SEQ ID NO: 1, and wherein a plant produced from said seed exhibits either an increased drought tolerance, or an increase in yield, or both, when compared to a control plant not comprising said recombinant DNA construct.

BRIEF DESCRIPTION OF THE DRAWINGS AND SEQUENCE LISTING

The disclosure can be more fully understood from the following detailed description and the accompanying drawings and Sequence Listing which form a part of this application.

FIG. 1 shows phd1 mutant phenotypes. (A) Two-week-old seedlings grown on MS media. (B and C) Growth phenotype of 2-month-old (B) and 4-month-old (C) plants grown in a paddy field. (D) The harvested panicles showed a reduced seed-setting ratio for phd1-1. (A-D) wild type (left) and phd1-1 (right). (E-G) Quantification of the agricultural traits of tiller number (E), seed setting ration (F), and grain weight per plant (G). Each bar is the mean±SD from 30 replicate samples. (H, I) Diurnal changes in sucrose (H) and starch (I) content of phd1-1 and wild type. Mature leaves of individual wild type and phd1-1 plants at the anthesis stage were harvested and immediately frozen in liquid nitrogen. Each point is the mean±SD from ten replicate samples.

Figure 2:
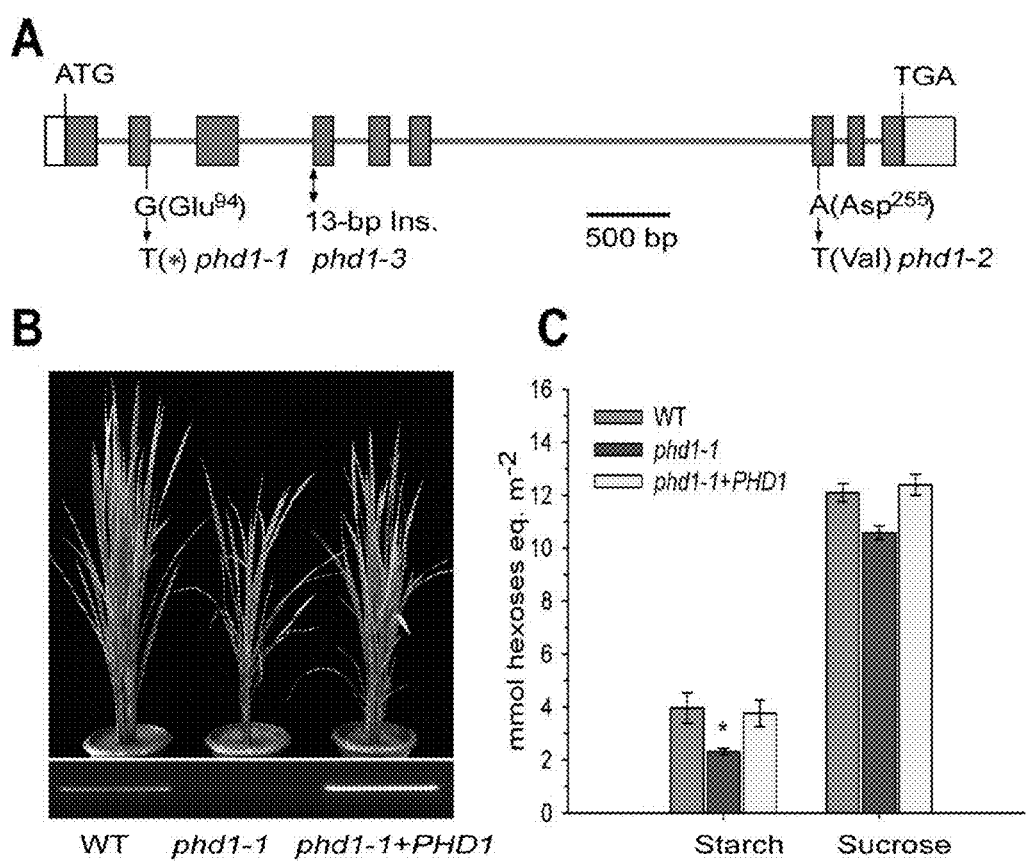

FIG. 2 shows the molecular identification of PHD1. (A) Structure of the PHD1 gene and its mutation sites in three phd1 alleles. The PHD1 gene consists of nine exons (green boxes) and eight introns (gray lines). Nucleotide insertion and substitutions in the three phd1 alleles are indicated. (B, C) Functional complementation of the phd1 mutant. (B) Phenotypes of wild type, phd1-1, and the complemented line phd1-1+PHD1 plants at the tillering stage. Expression level of PHD1 transcripts was detected by semi-quantitative RT-PCR. (C) Sucrose and starch content in flag leaves of wild type, phd1-1, and the complemented line phd1-1+PHD1 plants at noon of the day at the anthesis stage. Error bars represent SD of eight different individuals. *significant difference between phd1-1 mutant and wild type (P=0.05).

Figure 3:
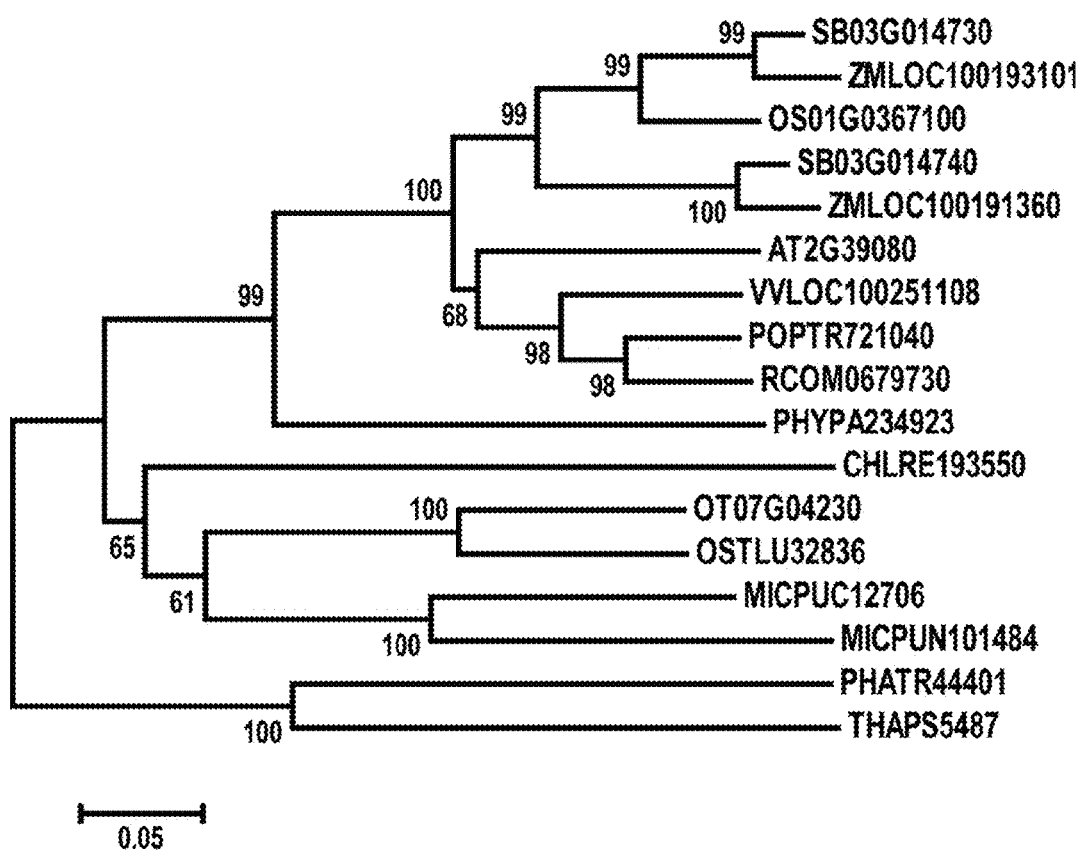

FIG. 3 shows the phylogenetic analysis of PHD1. MEGA4 Neighbor-Joining tree was inferred from the amino add sequences of the PHD1 (Os01g0367100) homologs among green plants. Bootstrap values are based on 1000 replications and are indicated in their respective nodes. The scale bar indicates genetic distance based on branch length. The alignment for the constructed tree is shown in Fig. S3.

Figure 4:
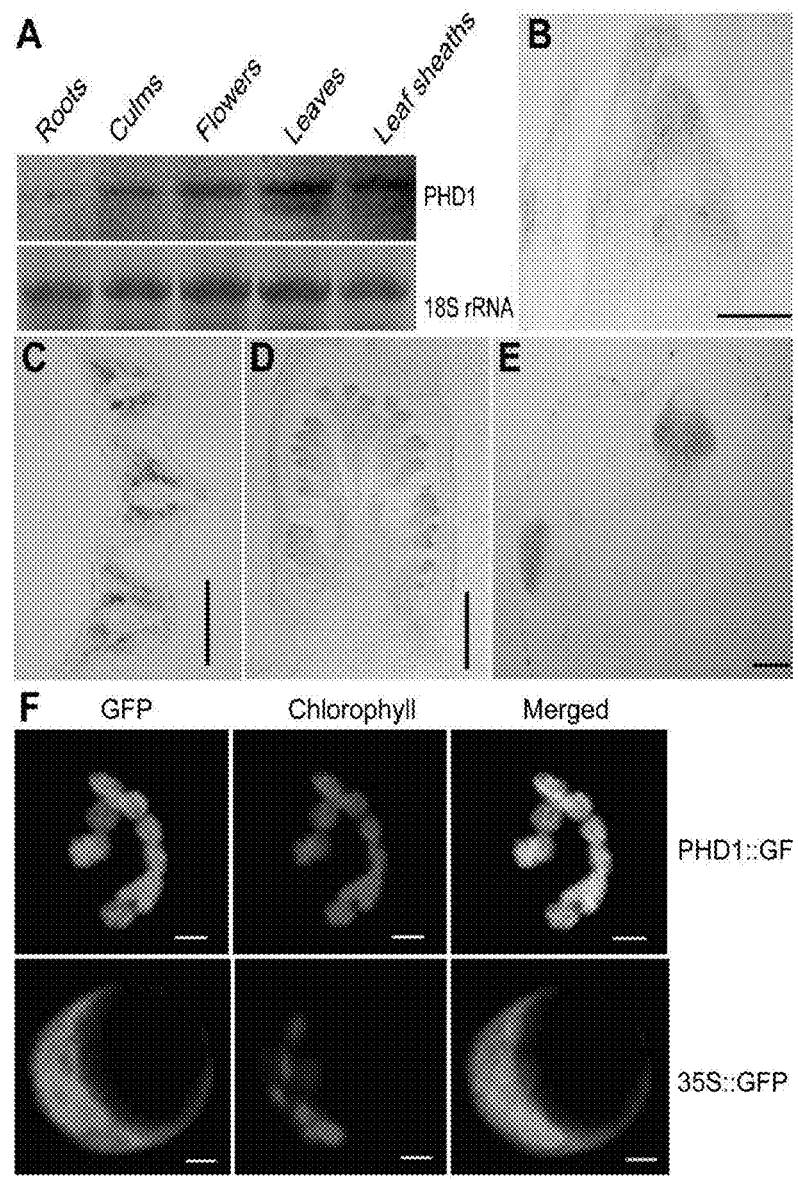

FIG. 4 shows PHD1 expression analysis and PHD1 protein subcellular localization. (A) RNA gel blot analysis of the PHD1 gene in roots, culms, flowers, leaf blades, and leaf sheaths just before the anthesis stage. (B-E) PHD1 expression patterns detected by mRNA in situ hybridization. The PHD1 signal was detected at the shoot apical meristem and young leaves (B), leaf mesophyll cells around vascular bundles (C), young inflorescences (D), and axillary buds (E). Bars=150 µm in (B), (C), and (E), and 500 µm in (D). (F) Rice protoplasts transformed with 35S::GFP (lower panel) and 35S::PHD1-GFP (upper panel) plasmids. Chlorophyll autofluorescence (middle); GFP fluorescence (left); merged images (right). Bars=5 µm.

Figure 5:
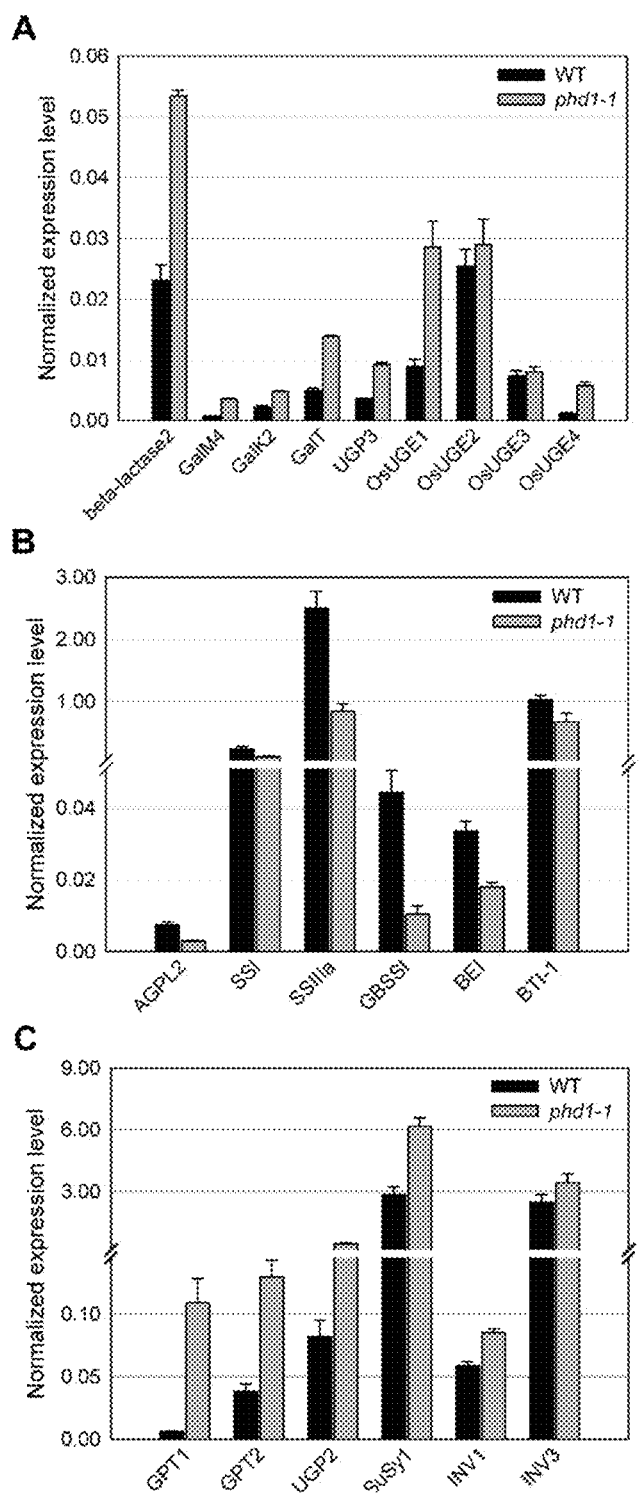

FIG. 5 shows the expression analysis of key genes involved in UDP-Gal biosynthesis and carbohydrate allocation in leaves of phd1-1 plants. (A) The expression of genes involved in the UDP-Gal biosynthesis pathway was upregulated in phd1-1. (B) The expression of starch biosynthesis genes was down-regulated in phd1-1. (C) The expression of sucrose cleavage genes was upregulated in phd1-1. Expression values are displayed as the ratio of expression to rice 18S RNA (mean±SE). All assays were carried out with three biological replicates.

Figure 6:
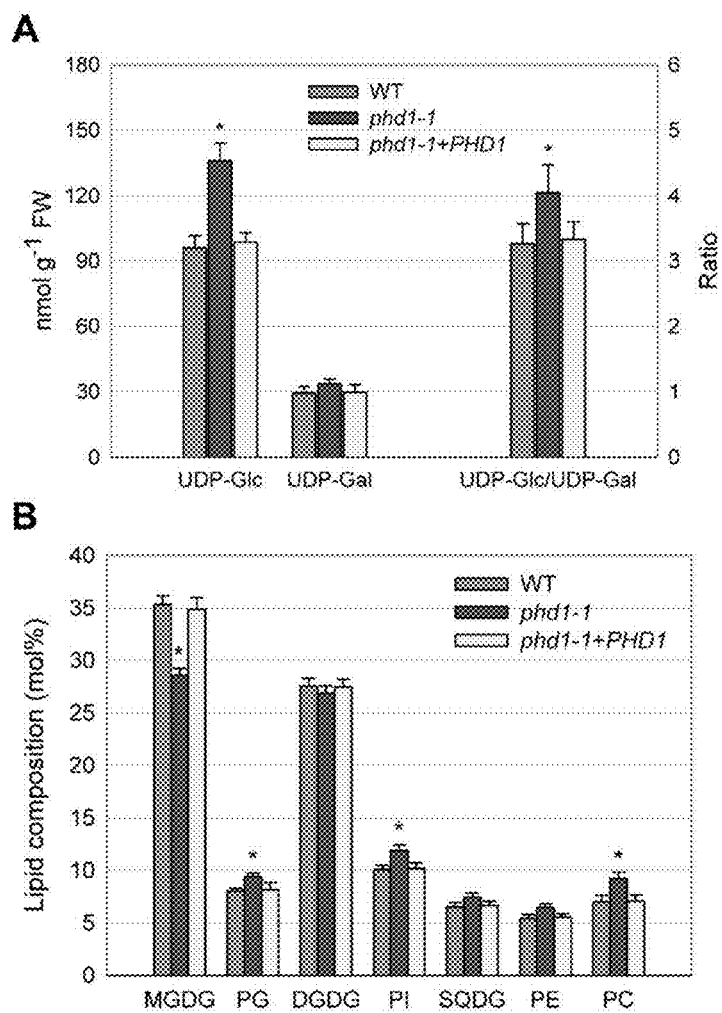

FIG. 6 shows UDP-sugar content and glycolipid composition in phd1 plants. (A) UDP-Glc and UDP-Gal content in leaves of wild type, phd1-1, and PHD1-complemented plants. The values represent the means±SE of six independent experiments. (B) Polar lipid composition in leaves of wild type, phd1-1, and PHD1-complemented plants grown in paddy fields. Glycerolipids were quantified by GC of leaf lipids separated by TLC. The bars show lipid composition in mol % and indicate means±SD of three measurements. UDP-Glc, UDP-glucose; UDP-Gal, UDP-galactose; FW, fresh weight; PC, phosphatidylcholine; PE, phosphatidylethanolamine; PG, phosphatidylglycerol; PI, phosphatidylinositol; SQDG, sulfoquinovosyldiacylglycerol.

Figure 7:
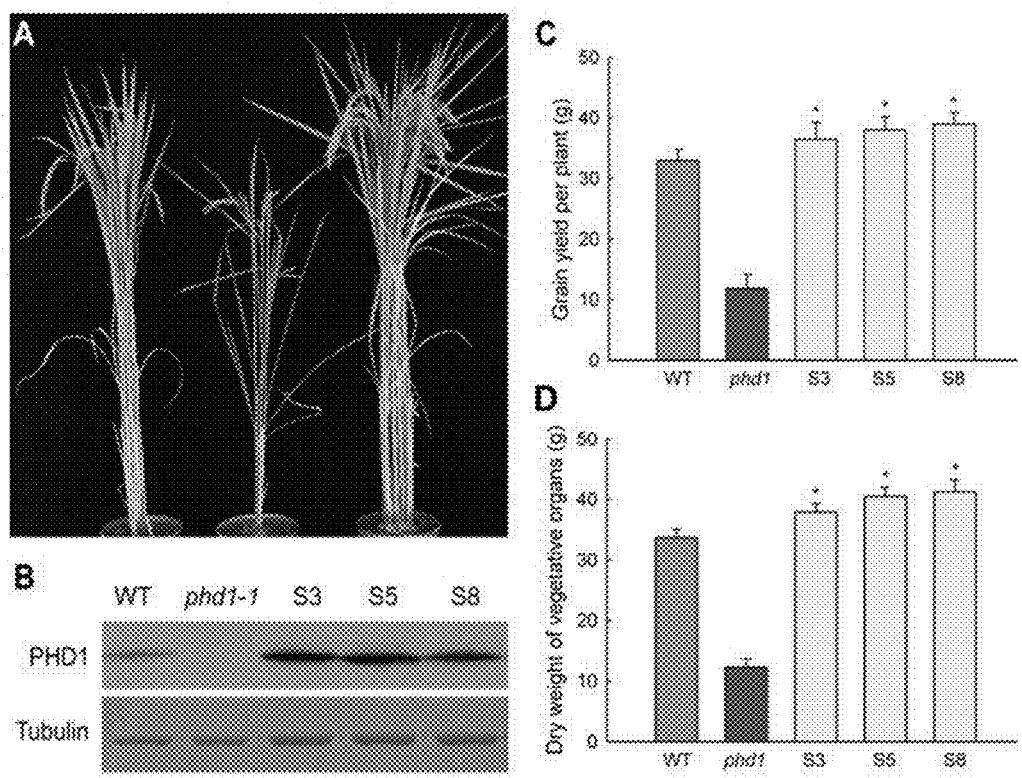

FIG. 7 shows the improved agricultural traits of transgenic rice overexpressing PHD1. (A) Phenotypic differences of wild type, phd1-1, and transgenic line S3 at the grain-filling stage grown in paddy fields. (B) Immunoblot analysis of PHD1 protein expression in wild type, phd1-1, and PHD1 overexpressing transgenic lines (S3, S5, and S8). Tubulin is shown as loading control. Increased accumulation of PHD1 protein was observed in transgenic lines. (C,D) Grain yield per plant (C) and dry weight of vegetative organs after harvesting (D) were increased in transgenic plants. Values are means±SD from at least 30 plants/line, *Significant difference (P<0.05).

Figure 8:
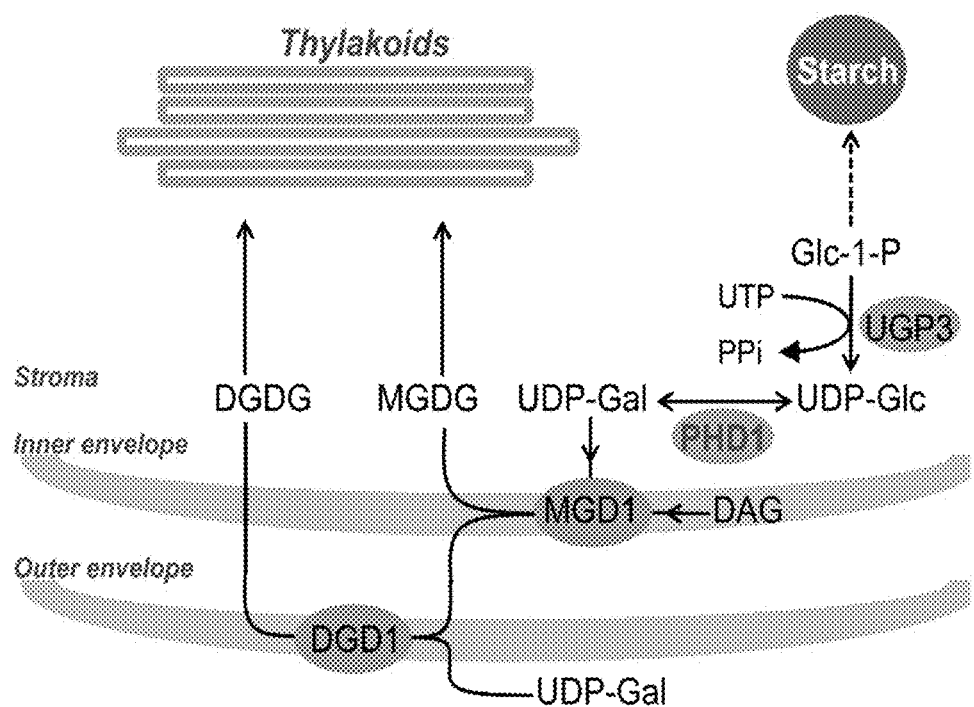

FIG. 8 shows a schematic model for the role of PHD1 in the galactolipid biosynthetic pathway for chloroplast membranes. Biosynthetic schemes for two glycoglycerolipids under normal growth conditions are indicated along with the pathway involving PHD1. Glc-1-P, glucose-1-phosphate; UGP, UDP-glucose pyrophosphorylase; DAG, diacylglycerol; UTP, uridine-5'-triphosphate; PPi, pyrophosphate.

Figure 9:
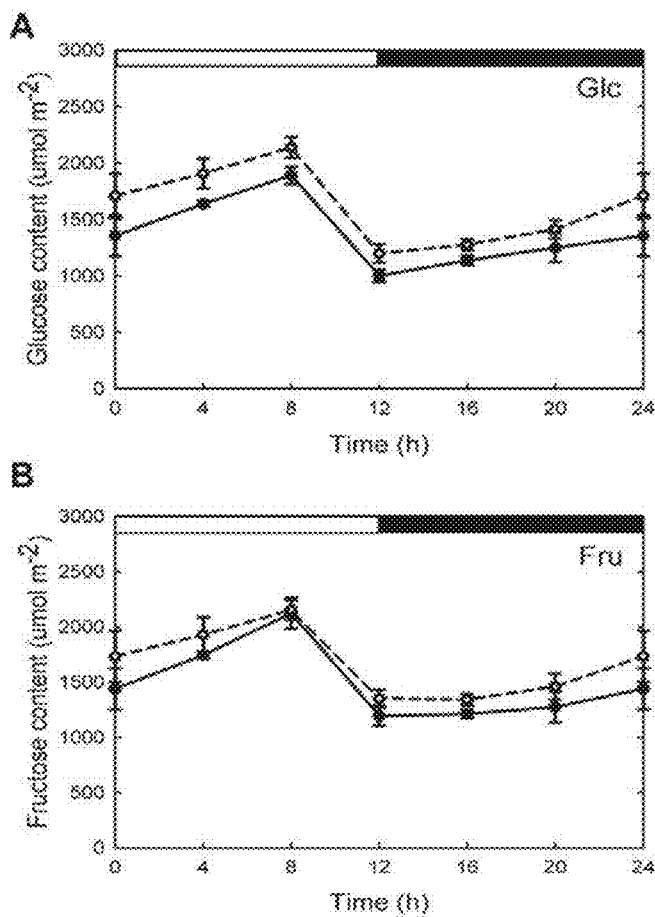

FIG. 9 shows the diurnal changes in hexose concentration of phd1-1 and WT. The mature leaves of individual wild type (● black symbols with solid lines) and phd1-1 (○ empty symbols with broken lines) plants were harvested and immediately frozen in liquid $N_2$. Each point is the mean±standard deviation from ten replicate samples.

Figure 10:
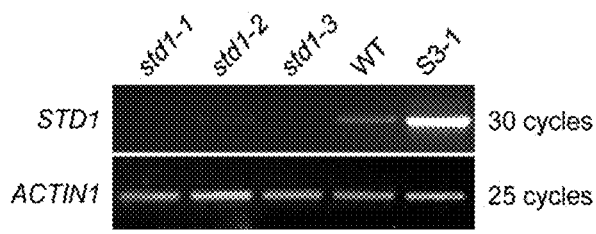

FIG. 10 shows PHD1 transcript level in wild type and three allelic phd1 mutants. The equal abundance of RNA among samples was confirmed by RT-PCR detection of ACTIN1 transcripts. phd1-1 to −3, three allelic phd1 mutant lines; S3-1, PHD1 overexpressing transgenic line.

Figure 11:
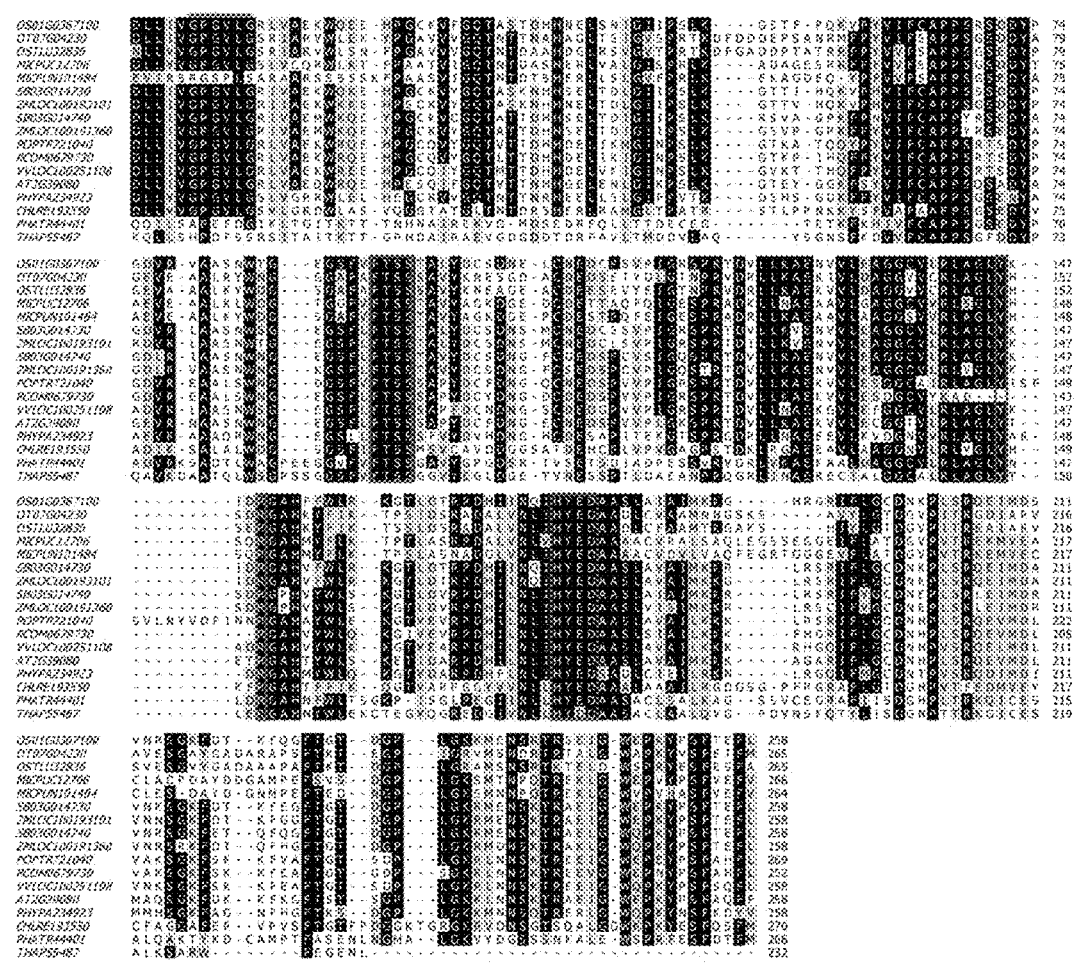

FIG. 11 is a comparison (SEQ ID NOS: 1, 11, 12, 13, 14, 2, 4, 3, 5, 7, 9, 6, 8, 10, 15, 16 and 17, consecutively) of the seventeen conserved regions from PHD1 and the green plant homolog sequences. The sequences were searched using BLASTP and aligned using CLUSTALW. Identical amino acid residues are boxed, and similar residues are shaded. The red bar indicates the conserved motif GXGXXG (NAD+-binding), and catalytic amino acid residues of the active site are boxed in red. PHD1: Os01g0367100.

Figure 12:
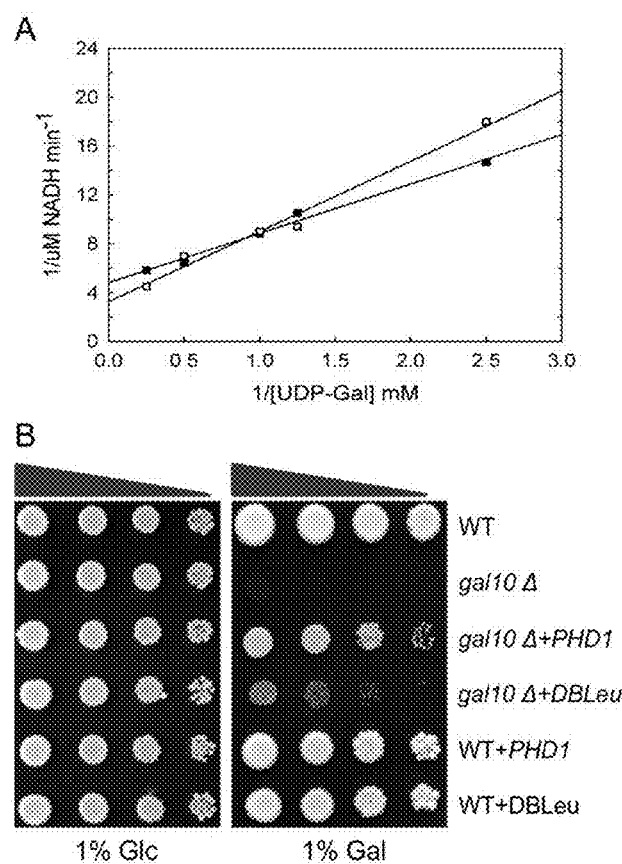

FIG. 12 shows biochemical function and genetic complement assay of PHD1. (A) UGE activity assay of PHD1 in vitro. Lineweaver-Burk plots of purified recombinant PHD1 UGE activity at 30° C. (■) and at 37° C. (□). (B) PHD1 can complement a S. cerevisiae gal10 mutant. A yeast gal1 0 mutant strain was transformed with plasmids containing PHD1 cDNAs, and grown on either glucose or galactose medium.

The sequence descriptions and Sequence Listing attached hereto comply with the rules governing nucleotide and/or amino acid sequence disclosures in patent applications as set forth in 37 C.F.R. §1.821-1.825.

The Sequence Listing contains the one letter code for nucleotide sequence characters and the three letter codes for amino acids as defined in conformity with the IUPAC-IUBMB standards described in *Nucleic Acids Res.* 13:3021-3030 (1985) and in the *Biochemical J.* 219 (No. 2):345-373 (1984) which are herein incorporated by reference. The symbols and format used for nucleotide and amino acid sequence data comply with the rules set forth in 37 C.F.R. §1.822.

DETAILED DESCRIPTION

PHD1 encodes a novel rice plastidial UGE involved in the biosynthesis of chloroplast galactolipids. A mutation in PHD1 lead to disturbed carbon assimilation homeostasis and impaired photosynthetic efficiency. PHD1 encodes for an active epimerase that is localized to chloroplasts, and therefore that the UDP-Gal substrate for MGDG biosynthesis can be generated in situ in chloroplasts (FIG. 8). This surprising result provides a genetic and biochemical framework to engineer the novel functional mechanism of this UGE in plastids, and to evaluate the role of galactolipids in photosynthetic activity of plants including rice.

MGD1 is considered to be the major isoform of MGDG synthases mostly important for thylakoid membrane biogenesis. In *Arabidopsis*, two more MGDG synthases, MGD2 and MGD3, are targeted to the outer chloroplast envelope where substrates can be recruited from the cytosol. MGDG generated by them can move from the outer to the inner envelope and to the thylakoids. Herein, it is shown that compared to wild type, the relative amount of the major galactolipid MGDG in phd1-1 was reduced by 19%, whereas that of DGDG was only slightly decreased by 2.5%. However, slight increases in the mol % amounts of several phospholipids were found to compensate for the approximately 7 mol % of galactolipids lost in the phd1-1 mutant. These results are consistent with the notion that the amounts of glycolipids and phospholipids are reciprocally controlled in plants to maintain proper balance of lipids in the thylakoid membrane.

Most galactolipids are restricted to plastid membranes during normal growth and development, however, DGDG can also be found in extraplastidic membranes following phosphate (Pi) starvation. In addition, x-ray crystallographic analyses of photosynthetic proteins in cyanobacteria revealed that MGDG is associated with the core of the reaction centers of both photosystems I and II (PSI and PSII) indicating that these lipids are required not only as bulk constituents of photosynthetic membranes, but also for the photosynthetic reaction itself. The effective quantum yield of photochemical energy conversion in photosystem II ($\phi_{PSII}$) was reduced in the phd1-1 mutant. Seedlings lacking MGDG were shown to have disrupted photosynthetic membranes, leading to a complete impairment of photosynthetic ability and photoautotrophic growth. A reduction of MGDG to 80% of wild type levels in the phd1-1 mutant led to the dramatic phenotype of retarded growth, reduced photosynthetic capability, and decreased photoassimilate accumulation. The stunted growth phenotype of phd1-1 mutants may be due to an insufficient provision of membrane building blocks to support chloroplast proliferation during plant growth, which is also consistent with the reduced size of chloroplasts in mutant plants. These effects may be due to a reduction of the absolute amount of MGDG or a reduced galactolipid to phospholipid ratio in chloroplast membranes.

In plants, starch acts as a depository for reduced carbon produced in leaves during the day, and as a supply of chemical energy and anabolic source molecules during the night. In the phd1-1 mutant, expression levels of starch biosynthesis genes such as AGP, SS, GBSS, and BE, were significantly downregulated in source leaves, leading to a sharp decrease of starch content. However, the reduced starch did not result in increased sucrose levels, because activation of sucrose cleavage genes SuSy1 and INV1/3 resulted in reduced sucrose and increased hexose-phosphate and UDP-Glc levels. Therefore, sucrose as the main transport form of photoassimilate produced in source organs was not able to export efficiently to the sink organs. Moreover, a large amount of UDP-Glc catalyzed by SuSy1 or UGP2 would be converted to UDP-Gal by cytosolic OsUGE1/4 and transported into chloroplast as galactosyl donors of chloroplast glycolipids to compensate for the loss of PHD1 activity in the phd1-1 mutant. In contrast, PHD1 overexpression in rice, which would enhance PHD1 activity in chloroplasts and may increase the relative amount of MGDG and increase the effective quantum yield of photochemical energy conversion in thylakoid membranes, resulted in increased photosynthetic efficiency and growth rate, implicating a key role of PHD1 for the photosynthetic system in plants including rice. These improvements of both biomass production and grain yield have significant economic implications in both traditional crop improvement and bioenergy crop production.

The disclosure of each reference set forth herein is hereby incorporated by reference in its entirety.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth.

As used herein:

"Epimerase activity" of a polypeptide indicates that peptide is capable of performing the catalysis of UDP-Gal to UDP-Glc.

The terms "monocot" and "monocotyledonous plant" are used interchangeably herein. A monocot of the current disclosure includes the Gramineae.

The terms "dicot" and "dicotyledonous plant" are used interchangeably herein. A dicot of the current disclosure includes the following families: Brassicaceae, Leguminosae, and Solanaceae.

The terms "full complement" and "full-length complement" are used interchangeably herein, and refer to a complement of a given nucleotide sequence, wherein the complement and the nucleotide sequence consist of the same number of nucleotides and are 100% complementary.

"*Arabidopsis*" and "*Arabidopsis thaliana*" are used interchangeably herein, unless otherwise indicated.

An "Expressed Sequence Tag" ("EST") is a DNA sequence derived from a cDNA library and therefore is a sequence which has been transcribed. An EST is typically obtained by a single sequencing pass of a cDNA insert. The sequence of an entire cDNA insert is termed the "Full-Insert Sequence" ("FIS"). A "Contig" sequence is a sequence assembled from two or more sequences that can be selected from, but not limited to, the group consisting of an EST, FIS and PCR sequence. A sequence encoding an entire or functional protein is termed a "Complete Gene Sequence" ("CGS") and can be derived from an FIS or a contig.

"Agronomic characteristic" is a measurable parameter including but not limited to, greenness, yield, growth rate, biomass, fresh weight at maturation, dry weight at maturation, fruit yield, seed yield, total plant nitrogen content, fruit nitrogen content, seed nitrogen content, nitrogen content in a vegetative tissue, total plant free amino acid content, fruit free amino acid content, seed free amino acid content, free amino acid content in a vegetative tissue, total plant protein content, fruit protein content, seed protein content, protein content in a vegetative tissue, drought tolerance, nitrogen uptake, root lodging, harvest index, stalk lodging, plant height, ear height, ear length, salt tolerance, early seedling vigor and seedling emergence under low temperature stress.

"Transgenic" refers to any cell, cell line, callus, tissue, plant part or plant, the genome of which has been altered by the presence of a heterologous nucleic acid, such as a recombinant DNA construct, including those initial transgenic events as well as those created by sexual crosses or asexual propagation from the initial transgenic event. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

"Genome" as it applies to plant cells encompasses not only chromosomal DNA found within the nucleus, but organelle DNA found within subcellular components (e.g., mitochondrial, plastid) of the cell.

"Plant" includes reference to whole plants, plant organs, plant tissues, seeds and plant cells and progeny of same. Plant cells include, without limitation, cells from seeds, suspension cultures, embryos, meristematic regions, callus tissue, leaves, roots, shoots, gametophytes, sporophytes, pollen, and microspores.

"Progeny" comprises any subsequent generation of a plant.

"Transgenic plant" includes reference to a plant which comprises within its genome a heterologous polynucleotide. For example, the heterologous polynucleotide is stably integrated within the genome such that the polynucleotide is passed on to successive generations. The heterologous polynucleotide may be integrated into the genome alone or as part of a recombinant DNA construct.

"Heterologous" with respect to sequence means a sequence that originates from a foreign species, or, if from the same species, is substantially modified from its native form in composition and/or genomic locus by deliberate human intervention.

"Polynucleotide", "nucleic acid sequence", "nucleotide sequence", or "nucleic acid fragment" are used interchangeably and is a polymer of RNA or DNA that is single- or double-stranded, optionally containing synthetic, non-natural or altered nucleotide bases. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

"Polypeptide", "peptide", "amino acid sequence" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The terms "polypeptide", "peptide", "amino acid sequence", and "protein" are also inclusive of modifications including, but not limited to, glycosylation, lipid attachment, sulfation, gamma-carboxylation of glutamic acid residues, hydroxylation and ADP-ribosylation.

"Messenger RNA (mRNA)" refers to the RNA that is without introns and that can be translated into protein by the cell.

"cDNA" refers to a DNA that is complementary to and synthesized from a mRNA template using the enzyme reverse transcriptase. The cDNA can be single-stranded or converted into the double-stranded form using the Klenow fragment of DNA polymerase I.

"Mature" protein refers to a post-translationally processed polypeptide; i.e., one from which any pre- or pro-peptides present in the primary translation product have been removed.

"Precursor" protein refers to the primary product of translation of mRNA; i.e., with pre- and pro-peptides still present. Pre- and pro-peptides may be and are not limited to intracellular localization signals.

"Isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

"Recombinant" refers to an artificial combination of two otherwise separated segments of sequence, e.g., by chemical synthesis or by the manipulation of isolated segments of nucleic acids by genetic engineering techniques. "Recombinant" also includes reference to a cell or vector, that has been modified by the introduction of a heterologous nucleic acid or a cell derived from a cell so modified, but does not encompass the alteration of the cell or vector by naturally occurring events (e.g., spontaneous mutation, natural transformation/transduction/transposition) such as those occurring without deliberate human intervention.

"Recombinant DNA construct" refers to a combination of nucleic acid fragments that are not normally found together in nature. Accordingly, a recombinant DNA construct may comprise regulatory sequences and coding sequences that are derived from different sources, or regulatory sequences and coding sequences derived from the same source, but arranged in a manner different than that normally found in nature.

The terms "entry clone" and "entry vector" are used interchangeably herein.

"Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences. The terms "regulatory sequence" and "regulatory element" are used interchangeably herein.

"Promoter" refers to a nucleic acid fragment capable of controlling transcription of another nucleic acid fragment.

"Promoter functional in a plant" is a promoter capable of controlling transcription in plant cells whether or not its origin is from a plant cell.

"Tissue-specific promoter" and "tissue-preferred promoter" are used interchangeably, and refer to a promoter that is expressed predominantly but not necessarily exclusively in one tissue or organ, but that may also be expressed in one specific cell.

"Developmentally regulated promoter" refers to a promoter whose activity is determined by developmental events.

"Operably linked" refers to the association of nucleic acid fragments in a single fragment so that the function of one is regulated by the other. For example, a promoter is operably linked with a nucleic acid fragment when it is capable of regulating the transcription of that nucleic acid fragment.

"Expression" refers to the production of a functional product. For example, expression of a nucleic acid fragment may refer to transcription of the nucleic acid fragment (e.g., transcription resulting in mRNA or functional RNA) and/or translation of mRNA into a precursor or mature protein.

"Phenotype" means the detectable characteristics of a cell or organism.

"Introduced" in the context of inserting a nucleic acid fragment (e.g., a recombinant DNA construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

A "transformed cell" is any cell into which a nucleic acid fragment (e.g., a recombinant DNA construct) has been introduced.

"Transformation" as used herein refers to both stable transformation and transient transformation.

"Stable transformation" refers to the introduction of a nucleic acid fragment into a genome of a host organism resulting in genetically stable inheritance. Once stably transformed, the nucleic acid fragment is stably integrated in the genome of the host organism and any subsequent generation.

"Transient transformation" refers to the introduction of a nucleic acid fragment into the nucleus, or DNA-containing organelle, of a host organism resulting in gene expression without genetically stable inheritance.

"Allele" is one of several alternative forms of a gene occupying a given locus on a chromosome. When the alleles present at a given locus on a pair of homologous chromosomes in a diploid plant are the same that plant is homozygous at that locus. If the alleles present at a given locus on a pair of homologous chromosomes in a diploid plant differ that plant is heterozygous at that locus. If a transgene is present on one of a pair of homologous chromosomes in a diploid plant that plant is hemizygous at that locus.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21-53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627-1632). A "mitochondrial signal peptide" is an amino acid sequence which directs a precursor protein into the mitochondria (Zhang and Glaser (2002) *Trends Plant Sci* 7:14-21).

The percent identity between two amino acid or nucleic acid sequences may be determined by visual inspection and mathematical calculation.

Alternatively, sequence alignments and percent identity calculations may be determined using a variety of comparison methods designed to detect homologous sequences including, but not limited to, the MEGALIGN® program of the LASERGENE® bioinformatics computing suite (DNASTAR® Inc., Madison, Wis.). Unless stated otherwise, multiple alignment of the sequences provided herein were performed using the Clustal V method of alignment (Higgins and Sharp (1989) CABIOS. 5:151 153) with the default parameters (GAP PENALTY=10, GAP LENGTH PENALTY=10). Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences, using the Clustal V program, it is possible to obtain "percent identity" and "divergence" values by viewing the "sequence distances" table on the same program; unless stated otherwise, percent identities and divergences provided and claimed herein were calculated in this manner.

Alternatively, the percent identity of two protein sequences may be determined by comparing sequence information based on the algorithm of Needleman, S. B. and Wunsch, C. D. (J. Mol. Biol., 48:443-453, 1970) and using the GAP computer program available from the University of Wisconsin Genetics Computer Group (UWGCG). The preferred default parameters for the GAP program include: (1) a scoring matrix, blosum62, as described by Henikoff, S, and Henikoff, J. G. (Proc. Natl. Acad. Sci. USA, 89:10915-10919, 1992); (2) a gap weight of 12; (3) a gap length weight of 4; and (4) no penalty for end gaps.

Other programs used by those skilled in the art of sequence comparison may also be used. The percent identity can be determined by comparing sequence information using, e.g., the BLAST program described by Altschul et al. (Nucl. Acids. Res., 25, p. 3389-3402, 1997). This program is available on the Internet at the web site of the National Center for Biotechnology Information (NCBI) or the DNA Data Bank of Japan (DDBJ). The details of various conditions (parameters) for identity search using the BLAST program are shown on these web sites, and default values are commonly used for search although part of the settings may be changed as appropriate. Alternatively, the percent identity of two amino acid sequences may be determined by using a program such as genetic information processing software GENETYX Ver.7 (Genetyx Corporation, Japan) or using an algorithm such as FASTA. In this case, default values may be used for search.

The percent identity between two nucleic acid sequences can be determined by visual inspection and mathematical calculation, or more preferably, the comparison is done by comparing sequence information using a computer program. An exemplary, preferred computer program is the Genetic Computer Group (GCG®; Madison, Wis.) WISCONSIN PACKAGE® version 10.0 program, "GAP" (Devereux et al., 1984, Nucl. Acids Res., 12:387). In addition to making a comparison between two nucleic acid sequences, this "GAP" program can be used for comparison between two amino acid sequences and between a nucleic acid sequence and an amino acid sequence. The preferred default parameters for the "GAP" program include: (1) the GCG® implementation of a unary comparison matrix (containing a value of 1 for identities and 0 for non-identities) for nucleotides, and the weighted amino acid comparison matrix of Gribskov and Burgess, Nucl. Acids Res., 14:6745, 1986, as described by Schwartz and Dayhoff, eds., "Atlas of Polypeptide Sequence and Structure," National Biomedical Research Foundation, pp. 353-358, 1979, or other comparable comparison matrices; (2) a penalty of 30 for each gap and an additional penalty of 1 for each symbol in each gap for amino acid sequences, or penalty of 50 for each gap and an additional penalty of 3 for each symbol in each gap for nucleotide sequences; (3) no penalty for end gaps; and (4) no maximum penalty for long gaps. Other programs used by those skilled in the art of sequence comparison can also be used, such as, for example, the BLASTN program version 2.2.7, available for use via the National Library of Medicine website, or the WU-BLAST 2.0 algorithm (Advanced Biocomputing, LLC). In addition, the BLAST algorithm uses the BLOSUM62 amino acid scoring matrix, and optional parameters that can be used are as follows: (A) inclusion of a filter to mask segments of the query sequence that have low compositional complexity (as determined by the SEG program of Wootton and Federhen (Computers and Chemistry, 1993); also see Wootton and Federhen, 1996, "Analysis of compositionally biased regions in sequence databases," Methods Enzymol., 266: 554-71) or segments consisting of short-periodicity internal repeats (as determined by the XNU program of Clayerie and States (Computers and Chemistry, 1993)), and (B) a statistical significance threshold for reporting matches against database sequences, or E-score (the expected probability of matches being found merely by chance, according to the stochastic model of Karlin and Altschul, 1990; if the statistical significance ascribed to a match is greater than this E-score threshold, the match will not be reported); preferred E-score threshold values are 0.5, or in order of increasing preference, 0.25, 0.1, 0.05, 0.01, 0.001, 0.0001, 1e-5, 1e-10, 1e-15, 1e-20, 1e-25, 1e-30, 1e-40, 1e-50, 1e-75, or 1e-100.

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Sambrook").

Turning now to the embodiments:

Embodiments include isolated polynucleotides and polypeptides, recombinant DNA constructs useful for conferring drought tolerance, compositions (such as plants or seeds) comprising these recombinant DNA constructs, and methods utilizing these recombinant DNA constructs.

Isolated Polynucleotides and Polypeptides:

The present disclosure includes the following isolated polynucleotides and polypeptides:

An isolated polynucleotide comprising: (i) a nucleic acid sequence encoding a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 1 or (ii) a full complement of the nucleic acid sequence of (i), wherein the full complement and the nucleic acid sequence of (i) consist of the same number of nucleotides and are 100% complementary. Any of the foregoing isolated polynucleotides may be utilized in any recombinant DNA constructs of the present disclosure. The polypeptide is preferably a PHD1 polypeptide.

An isolated polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 1. The polypeptide is preferably a PHD1 polypeptide.

An isolated polypeptide wherein the amino acid sequence is derived from SEQ ID NO: 1 by alteration of one or more amino acids by at least one method selected from the group consisting of: deletion, substitution, addition and insertion; and (c) a polypeptide wherein the amino acid sequence of the polypeptide comprises SEQ ID NO: 1. The polypeptide is preferably a PHD1 polypeptide.

An isolated polynucleotide comprising a nucleotide sequence encoding a polypeptide with epimerase activity, wherein the nucleotide sequence is hybridizable under stringent conditions with a DNA molecule comprising the full complement of SEQ ID NO: 18-34.

Site-directed mutagenesis may be accomplished, for example, as follows using a synthetic oligonucleotide primer that is complementary to single-stranded phage DNA to be mutated, except for having a specific mismatch (i.e., a desired mutation). Namely, the above synthetic oligonucleotide is used as a primer to cause synthesis of a complementary strand by phages, and the resulting duplex DNA is then used to transform host cells. The transformed bacterial culture is plated on agar, whereby plaques are allowed to form from phage-containing single cells. As a result, in theory, 50% of new colonies contain phages with the mutation as a single strand, while the remaining 50% have the original sequence. At a temperature which allows hybridization with DNA completely identical to one having the above desired mutation, but not with DNA having the original strand, the resulting plaques are allowed to hybridize with a synthetic probe labeled by kinase treatment. Subsequently, plaques hybridized with the probe are picked up and cultured for collection of their DNA.

The term "under stringent conditions" means that two sequences hybridize under moderately or highly stringent conditions. More specifically, moderately stringent conditions can be readily determined by those having ordinary skill in the art, e.g., depending on the length of DNA. The basic conditions are set forth by Sambrook et al., Molecular Cloning: A Laboratory Manual, third edition, chapters 6 and 7, Cold Spring Harbor Laboratory Press, 2001 and include the use of a prewashing solution for nitrocellulose filters 5×SSC, 0.5% SDS, 1.0 mM EDTA (pH 8.0), hybridization conditions of about 50% formamide, 2×SSC to 6×SSC at about 40-50° C. (or other similar hybridization solutions, such as Stark's solution, in about 50% formamide at about 42° C.) and washing conditions of, for example, about 40-60° C., 0.5-6×SSC, 0.1% SDS. Preferably, moderately stringent conditions include hybridization (and washing) at about 50° C. and 6×SSC. Highly stringent conditions can also be readily determined by those skilled in the art, e.g., depending on the length of DNA.

Generally, such conditions include hybridization and/or washing at higher temperature and/or lower salt concentration (such as hybridization at about 65° C., 6×SSC to 0.2×SSC, preferably 6×SSC, more preferably 2×SSC, most preferably 0.2×SSC), compared to the moderately stringent conditions. For example, highly stringent conditions may include hybridization as defined above, and washing at approximately 65-68° C., 0.2×SSC, 0.1% SDS. SSPE (1×SSPE is 0.15 M NaCl, 10 mM NaH2PO4, and 1.25 mM EDTA, pH 7.4) can be substituted for SSC (1×SSC is 0.15 M NaCl and 15 mM sodium citrate) in the hybridization and washing buffers; washing is performed for 15 minutes after hybridization is completed.

"Suppression DNA construct" is a recombinant DNA construct which when transformed or stably integrated into the genome of the plant, results in "silencing" of a target gene in the plant. The target gene may be endogenous or transgenic to the plant. "Silencing," as used herein with respect to the target gene, refers generally to the suppression of levels of mRNA or protein/enzyme expressed by the target gene, and/or the level of the enzyme activity or protein functionality. The terms "suppression", "suppressing" and "silencing", used interchangeably herein, include lowering, reducing, declining, decreasing, inhibiting, eliminating or preventing. "Silencing" or "gene silencing" does not specify mechanism and is inclusive, and not limited to, anti-sense, cosuppression, viral-suppression, hairpin suppression, stem-loop suppression, RNAi-based approaches, and small RNA-based approaches.

A suppression DNA construct may comprise a region derived from a target gene of interest and may comprise all or part of the nucleic acid sequence of the sense strand (or antisense strand) of the target gene of interest. Depending upon the approach to be utilized, the region may be 100% identical or less than 100% identical (e.g., at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical) to all or part of the sense strand (or antisense strand) of the gene of interest.

Suppression DNA constructs are well-known in the art, are readily constructed once the target gene of interest is selected, and include, without limitation, cosuppression constructs, antisense constructs, viral-suppression constructs, hairpin suppression constructs, stem-loop suppression constructs, double-stranded RNA-producing constructs, and more generally, RNAi (RNA interference) constructs and small RNA constructs such as sRNA (short interfering RNA) constructs and miRNA (microRNA) constructs.

"Antisense inhibition" refers to the production of antisense RNA transcripts capable of suppressing the expression of the target gene or gene product. "Antisense RNA" refers to an RNA transcript that is complementary to all or part of a target primary transcript or mRNA and that blocks the expression of a target isolated nucleic acid fragment (U.S. Pat. No. 5,107,065). The complementarity of an antisense RNA may be with any part of the specific gene transcript, i.e., at the 5' non-coding sequence, 3' non-coding sequence, introns, or the coding sequence.

"Cosuppression" refers to the production of sense RNA transcripts capable of suppressing the expression of the target gene or gene product. "Sense" RNA refers to RNA transcript that includes the mRNA and can be translated into protein within a cell or in vitro. Cosuppression constructs in plants have been previously designed by focusing on overexpression of a nucleic acid sequence having homology to a native mRNA, in the sense orientation, which results in the reduction of all RNA having homology to the overexpressed sequence (see Vaucheret et al., *Plant J.* 16:651-659 (1998); and Gura, *Nature* 404:804-808 (2000)).

Another variation describes the use of plant viral sequences to direct the suppression of proximal mRNA encoding sequences (PCT Publication No. WO 98/36083 published on Aug. 20, 1998).

Regulatory Sequences:

A recombinant DNA construct of the present disclosure may comprise at least one regulatory sequence. A regulatory sequence may be a promoter.

A number of promoters can be used in recombinant DNA constructs of the present disclosure. The promoters can be selected based on the desired outcome, and may include constitutive, tissue-specific, inducible, or other promoters for expression in the host organism. Promoters that cause a gene to be expressed in most cell types at most times are commonly referred to as "constitutive promoters".

High level, constitutive expression of the candidate gene under control of the 35S or UBI promoter may have pleiotropic effects, although candidate gene efficacy may be estimated when driven by a constitutive promoter. Use of tissue-specific and/or stress-specific promoters may eliminate undesirable effects but retain the ability to enhance drought tolerance. This effect has been observed in *Arabidopsis* (Kasuga et al. (1999) Nature Biotechnol. 17:287-91).

Suitable constitutive promoters for use in a plant host cell include, for example, the core promoter of the Rsyn7 promoter and other constitutive promoters disclosed in WO 99/43838 and U.S. Pat. No. 6,072,050; the core CaMV 35S promoter (Odell et al., Nature 313:810-812 (1985)); rice actin (McElroy et al., Plant Cell 2:163-171 (1990)); ubiquitin (Christensen et al., Plant Mol. Biol. 12:619-632 (1989) and Christensen et al., Plant Mol. Biol. 18:675-689 (1992)); pEMU (Last et al., Theor. Appl. Genet. 81:581-588 (1991)); MAS (Velten et al., EMBO J. 3:2723-2730 (1984)); ALS promoter (U.S. Pat. No. 5,659,026), and the like. Other constitutive promoters include, for example, those discussed in U.S. Pat. Nos. 5,608,149; 5,608,144; 5,604,121; 5,569,597; 5,466,785; 5,399,680; 5,268,463; 5,608,142; and 6,177,611.

In choosing a promoter to use in the methods of the disclosure, it may be desirable to use a tissue-specific or developmentally regulated promoter. A tissue-specific or developmentally regulated promoter is a DNA sequence which regulates the expression of a DNA sequence selectively in the cells/tissues of a plant critical to tassel development, seed set, or both, and limits the expression of such a DNA sequence to the period of tassel development or seed maturation in the plant. Any identifiable promoter may be used in the methods of the present disclosure which causes the desired temporal and spatial expression. A leaf specific promoter is suitable.

Inducible promoters selectively express an operably linked DNA sequence in response to the presence of an endogenous or exogenous stimulus, for example by chemical compounds (chemical inducers) or in response to environmental, hormonal, chemical, and/or developmental signals. Inducible or regulated promoters include, for example, promoters regulated by light, heat, stress, flooding or drought, phytohormones, wounding, or chemicals such as ethanol, jasmonate, salicylic acid, or safeners.

Promoters for use include the following: 1) the stress-inducible RD29A promoter (Kasuga et al. (1999) Nature Biotechnol. 17:287-91); 2) the barley promoter, B22E; expression of B22E is specific to the pedicel in developing maize kernels ("Primary Structure of a Novel Barley Gene Differentially Expressed in Immature Aleurone Layers". Klemsdal, S. S. et al., Mol. Gen. Genet. 228(1/2):9-16 (1991)); and 3) maize promoter, Zag2 ("Identification and molecular characterization of ZAG1, the maize homolog of the *Arabidopsis* floral homeotic gene AGAMOUS", Schmidt, R. J. et al., Plant Cell 5(7):729-737 (1993); "Structural characterization, chromosomal localization and phylogenetic evaluation of two pairs of AGAMOUS-like MADS-box genes from maize", Theissen et al. Gene 156(2):155-166 (1995); NCBI GenBank Accession No. X80206)). Zag2 transcripts can be detected 5 days prior to pollination to 7 to 8 days after pollination ("DAP"), and directs expression in the carpel of developing female inflorescences and Ciml which is specific to the nucleus of developing maize kernels. Ciml transcript is detected 4 to 5 days before pollination to 6 to 8 DAP. Other useful promoters include any promoter which can be derived from a gene whose expression is maternally associated with developing female florets.

Promoters may be derived in their entirety from a native gene, or be composed of different elements derived from different promoters found in nature, or even comprise synthetic DNA segments.

Recombinant DNA constructs of the present disclosure may also include other regulatory sequences, including but not limited to, translation leader sequences, introns, and polyadenylation recognition sequences. In another embodiment of the present disclosure, a recombinant DNA construct of the present disclosure further comprises an enhancer or silencer.

An intron sequence can be added to the 5' untranslated region, the protein-coding region or the 3' untranslated region to increase the amount of the mature message that accumulates in the cytosol. Inclusion of a spliceable intron in the transcription unit in both plant and animal expression constructs has been shown to increase gene expression at both the mRNA and protein levels up to 1000-fold. Buchman and Berg, *Mol. Cell Biol.* 8:4395-4405 (1988); Callis et al., *Genes Dev.* 1:1183-1200 (1987).

Any plant can be selected for the identification of regulatory sequences and PHD1 polypeptide genes to be used in recombinant DNA constructs of the present disclosure. Examples of suitable plant targets for the isolation of genes and regulatory sequences would include but are not limited to alfalfa, apple, apricot, *Arabidopsis*, artichoke, arugula, asparagus, avocado, banana, barley, beans, beet, blackberry, blueberry, broccoli, brussels sprouts, cabbage, canola, cantaloupe, carrot, cassava, castorbean, cauliflower, celery, cherry, chicory, cilantro, citrus, clementines, clover, coconut, coffee, corn, cotton, cranberry, cucumber, Douglas fir, eggplant, endive, escarole, eucalyptus, fennel, figs, garlic, gourd, grape, grapefruit, honey dew, jicama, kiwifruit, lettuce, leeks, lemon, lime, Loblolly pine, linseed, mango, melon, mushroom, nectarine, nut, oat, oil palm, oil seed rape, okra, olive, onion, orange, an ornamental plant, palm, papaya, parsley, parsnip, pea, peach, peanut, pear, pepper, persimmon, pine, pineapple, plantain, plum, pomegranate, poplar, potato, pumpkin, quince, radiata pine, radicchio, radish, rapeseed, raspberry, rice, rye, sorghum, Southern pine, soybean, spinach, squash, strawberry, sugarbeet, sugarcane, sunflower, sweet potato, sweetgum, tangerine, tea, tobacco, tomato, triticale, turf, turnip, a vine, watermelon, wheat, yams, and zucchini.

Compositions:

A composition of the present disclosure is a plant comprising in its genome any of the recombinant DNA constructs of the present disclosure (such as any of the constructs discussed above). Compositions also include any progeny of the plant, and any seed obtained from the plant or its progeny, wherein the progeny or seed comprises within its genome the recombinant DNA construct. Progeny includes subsequent generations obtained by self-pollination or out-crossing of a plant. Progeny also includes hybrids and inbreds.

In hybrid seed propagated crops, mature transgenic plants can be self-pollinated to produce a homozygous inbred plant. The inbred plant produces seed containing the newly introduced recombinant DNA construct. These seeds can be grown to produce plants that would exhibit an altered agronomic characteristic (e.g., an increased agronomic characteristic optionally under water limiting conditions), or used in a breeding program to produce hybrid seed, which can be grown to produce plants that would exhibit such an altered agronomic characteristic. The seeds may be maize seeds.

The plant may be a monocotyledonous or dicotyledonous plant, for example, a maize, rice or soybean plant, such as a maize hybrid plant or a maize inbred plant. The plant may also be sunflower, sorghum, canola, wheat, alfalfa, cotton, barley, millet, sugarcane, switchgrass, tobacco, potato and sugar beet.

The recombinant DNA construct may be stably integrated into the genome of the plant.

The PHD1 polypeptide may be from *Arabidopsis thaliana, Zea mays, Glycine max, Glycine tabacina, Glycine soja* or *Glycine tomentella*.

At least one agronomic characteristic may be selected from the group consisting of greenness, yield, growth rate, biomass, fresh weight at maturation, dry weight at maturation, fruit yield, seed yield, total plant nitrogen content, fruit nitrogen content, seed nitrogen content, nitrogen content in a vegetative tissue, total plant free amino acid content, fruit free amino acid content, seed free amino acid content, free amino acid content in a vegetative tissue, total plant protein content, fruit protein content, seed protein content, protein content in a vegetative tissue, drought tolerance, nitrogen uptake, root lodging, harvest index, stalk lodging, plant height, ear height, ear length, salt tolerance, early seedling vigor and seedling emergence under low temperature stress. For example, the alteration of at least one agronomic characteristic may be an increase in yield, greenness or biomass.

In any of the foregoing embodiments 1-8 or any other embodiments of the present disclosure, the plant may exhibit the alteration of at least one agronomic characteristic when compared, under water limiting conditions, to a control plant not comprising said recombinant DNA construct.

"Drought" refers to a decrease in water availability to a plant that, especially when prolonged, can cause damage to the plant or prevent its successful growth (e.g., limiting plant growth or seed yield).

"Drought tolerance" is a trait of a plant to survive under drought conditions over prolonged periods of time without exhibiting substantial physiological or physical deterioration.

"Increased drought tolerance" of a plant is measured relative to a reference or control plant, and is a trait of the plant to survive under drought conditions over prolonged periods of time, without exhibiting the same degree of physiological or physical deterioration relative to the reference or control plant grown under similar drought conditions. Typically, when a transgenic plant comprising a recombinant DNA construct in its genome exhibits increased drought tolerance relative to a reference or control plant, the reference or control plant does not comprise in its genome the recombinant DNA construct.

One of ordinary skill in the art is familiar with protocols for simulating drought conditions and for evaluating drought tolerance of plants that have been subjected to simulated or naturally-occurring drought conditions. For example, one can simulate drought conditions by giving plants less water than normally required or no water over a period of time, and one can evaluate drought tolerance by looking for differences in physiological and/or physical condition, including (but not limited to) vigor, growth, size, or root length, or in particular, leaf color or leaf area size. Other techniques for evaluating drought tolerance include measuring chlorophyll fluorescence, photosynthetic rates and gas exchange rates.

A drought stress experiment may involve a chronic stress (i.e., slow dry down) and/or may involve two acute stresses (i.e., abrupt removal of water) separated by a day or two of recovery. Chronic stress may last 8-10 days. Acute stress may last 3-5 days. The following variables may be measured during drought stress and well watered treatments of transgenic plants and relevant control plants:

The variable "% area chg_start chronic-acute2" is a measure of the percent change in total area determined by remote visible spectrum imaging between the first day of chronic stress and the day of the second acute stress The variable "% area chg_start chronic-end chronic" is a measure of the percent change in total area determined by remote visible spectrum imaging between the first day of chronic stress and the last day of chronic stress.

The variable "% area chg_start chronic-harvest" is a measure of the percent change in total area determined by remote visible spectrum imaging between the first day of chronic stress and the day of harvest.

The variable "% area chg_start chronic-recovery24 hr" is a measure of the percent change in total area determined by remote visible spectrum imaging between the first day of chronic stress and 24 hrs into the recovery (24 hrs after acute stress 2).

The variable "psii_acute1" is a measure of Photosystem II (PSII) efficiency at the end of the first acute stress period. It provides an estimate of the efficiency at which light is absorbed by PSII antennae and is directly related to carbon dioxide assimilation within the leaf.

The variable "psii_acute2" is a measure of Photosystem II (PSII) efficiency at the end of the second acute stress period. It provides an estimate of the efficiency at which light is absorbed by PSII antennae and is directly related to carbon dioxide assimilation within the leaf.

The variable "fv/fm_acute1" is a measure of the optimum quantum yield (Fv/Fm) at the end of the first acute stress–(variable fluorescence difference between the maximum and minimum fluorescence/maximum fluorescence).

The variable "fv/fm_acute2" is a measure of the optimum quantum yield (Fv/Fm) at the end of the second acute stress–(variable flourescence difference between the maximum and minimum fluorescence/maximum fluorescence).

The variable "leaf rolling_harvest" is a measure of the ratio of top image to side image on the day of harvest.

The variable "leaf rolling_recovery24 hr" is a measure of the ratio of top image to side image 24 hours into the recovery.

The variable "Specific Growth Rate (SGR)" represents the change in total plant surface area (as measured by Lemna Tec Instrument) over a single day ($Y(t)=Y0*e^{r*t}$). $Y(t)=Y0*e^{r*t}$ is equivalent to % change in $Y/\Delta t$ where the individual terms are as follows: $Y(t)$=Total surface area at t; $Y0$=Initial total surface area (estimated); $r$=Specific Growth Rate day$^{-1}$, and t=Days After Planting ("DAP").

The variable "shoot dry weight" is a measure of the shoot weight 96 hours after being placed into a 104° C. oven.

The variable "shoot fresh weight" is a measure of the shoot weight immediately after being cut from the plant.

The Examples below describe some representative protocols and techniques for simulating drought conditions and/or evaluating drought tolerance.

Methods include but are not limited to the following:

A method for transforming a cell comprising transforming a cell with any of the isolated polynucleotides of the present disclosure. The cell transformed by this method is also included. In particular embodiments, the cell is eukaryotic cell, e.g., a yeast, insect or plant cell, or prokaryotic, e.g., a bacterial cell.

A method for producing a transgenic plant comprising transforming a plant cell with any of the isolated polynucleotides or recombinant DNA constructs of the present disclosure and regenerating a transgenic plant from the transformed plant cell. The disclosure is also directed to the transgenic plant produced by this method, and transgenic seed obtained from this transgenic plant.

A method for isolating a polypeptide of the disclosure from a cell or culture medium of the cell, wherein the cell comprises a recombinant DNA construct comprising a polynucleotide of the disclosure operably linked to at least one regulatory sequence, and wherein the transformed host cell is grown under conditions that are suitable for expression of the recombinant DNA construct.

A method of altering the level of expression of a polypeptide of the disclosure in a host cell comprising: (a) transforming a host cell with a recombinant DNA construct of the present disclosure; and (b) growing the transformed host cell under conditions that are suitable for expression of the recombinant DNA construct wherein expression of the recombinant DNA construct results in production of altered levels of the polypeptide of the disclosure in the transformed host cell.

A method of increasing yield and/or drought tolerance in a plant, comprising: (a) introducing into a regenerable plant cell a recombinant DNA construct comprising a polynucleotide operably linked to at least one regulatory sequence (for example, a promoter functional in a plant), wherein the polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 1 and (b) regenerating a transgenic plant from the regenerable plant cell after step (a), wherein the transgenic plant comprises in its genome the recombinant DNA construct and exhibits increased drought tolerance when compared to a control plant not comprising the recombinant DNA construct. The method may further comprise (c) obtaining a progeny plant derived from the transgenic plant, wherein said progeny plant comprises in its genome the recombinant DNA construct and exhibits increased drought tolerance when compared to a control plant not comprising the recombinant DNA construct.

EXAMPLES

The present disclosure is further illustrated in the following Examples, in which parts and percentages are by weight and degrees are Celsius, unless otherwise stated. It should be understood that these Examples, while indicating preferred embodiments of the disclosure, are given by way of illustration only. From the above discussion and these Examples, one skilled in the art can ascertain the essential characteristics of this disclosure, and without departing from the spirit and scope thereof, can make various changes and modifications of the disclosure to adapt it to various usages and conditions. Thus, various modifications of the disclosure in addition to those shown and described herein will be apparent to those skilled in the art from the foregoing description. Such modifications are also intended to fall within the scope of the appended claims.

Example 1

Isolation and Characterization of the Phd1 Mutant

Of 480 mutant lines with altered carbohydrate levels in vegetative organs, photoassimilate defective1 (phd1) with both low carbohydrate contents and stunted growth was selected for further characterization (FIG. 1). Compared to wild type, mature leaves of the mutant had low starch levels at all time-points taken during the light/dark cycle (FIG. 11). Scanning electron micrograph of culms demonstrated that fewer starch granules were deposited in parenchyma cells of the phd1 mutants. During the young seedling stage, both the shoots and primary roots of the mutant were shorter and lighter than those of the wild type (FIG. 1A). After internode elongation, the phd1 mutant exhibited a semi-dwarf, less tillering, retarded vegetative growth, later flowering, and less grain-filling phenotype (FIG. 1B-E). In addition, although the grain number per panicle was not altered between the mutant and wild type, the seed-setting ratio of the phd1 mutant was significantly decreased, which finally led to a significant reduction of grain yield (FIG. 1F, G).

Example 2

PHD1 Encodes a Functional Chloroplastic UDP-Glc Epimerase

Genetic analysis indicated that the phd1 phenotype was controlled by a single recessive gene that did not co-segregate with the T-DNA insertion, and hence map-based cloning was carried out. The PHD1 locus was physically delimited to a 72-kb region on the short arm of chromosome 1. This region contains six annotated genes, and sequencing of these genes from phd1-1 identified a single nucleotide transition (G-to-T) in exon 2 of Os01g0367100, leading to a premature translational termination. The identity of Os01g0367100 as PHD1 was confirmed by analysis of two other phd1 alleles isolated from the same genetic screen. A single nucleotide substitution (A-to-T) in exon 7 of phd1-2 and a 13-bp insertion between exon 3 and exon 4 of phd1-3 were found (FIG. 2A). Almost no PHD1 mRNA was detected in any of the three allelic mutants (Figure S2). The phd1 phenotype was fully complemented by transgenic expression of wild type Os01g0367100 in the phd1-1 mutant background (FIG. 2B, C), confirming that the nonsense mutation of Os01g0367100 was responsible for the presumed null mutant phenotype.

PHD1 has similarity to proteins from *Thalassiosira pseudonana* (XP_002290295), *Phaeodactylum tricornutum* (XP_002178225), *Chlamydomonas reinhardtii* (XP_001699105), *Micromonas pusilla* (EEH60780), *Ostreococcus tauri* (CAL54696), *Physcomitrella patens* (XP_001767242), *Ricinus communis* (XP_002516868), Arabidopsis thaliana (AT2G39080), Populus trichocarpa (XP_002311843), Vitis vinifera (XP_002276706), Zea mays (NP_001131736), and Sorghum bicolor (XP_002457832), incorporated herein by reference, with 27 to 75% amino acid identity (Figure S3). Phylogenetic analysis between PHD1 and its 16 structurally similar proteins indicated that PHD1 is closely related to Sb03g014730 from sorghum and LOC100193101 from maize (FIG. 3). PHD1 homologs/orthologs are only found in the plant kingdom, indicating that these proteins are evolutionarily conserved across plant species. Analysis of the conserved domain demonstrated that PHD1 and its homologs contain the consensus WcaG domain, featured in nucleoside-diphosphate sugar epimerases (FIG. 11A). UDP-Glc epimerase (UGE), a sugar epimerase catalyzes the interconversion of UDP-Glc and UDP-Gal. PHD1 and its homologs may function as novel plant specific UGEs.

To understand the PHD1's biochemical function as an UDP-Glc epimerase, the mature PHD1 protein lacking the putative N-terminal 62-aa transit peptide was expressed in E. coli and UGE activity was examined. The result showed that PHD1 could catalyze the conversion of UDP-Gal to UDP-Glc, and curve fitting indicated that UDP-Gal binding followed a simple Michaelis-Menten kinetics with a $K_m$ value of 0.84 mM at 30° C. (FIG. 12A). To examine whether PHD1 had UDP-Glc epimerase activity in vivo, the mature PHD1 was expressed from the yeast glyceraldehyde-3-phosphate dehydrogenase promoter to complement the auxotrophic phenotype of a yeast gal10Δ mutant, which cannot grow on a medium containing D-galactose as sole carbon source. The complementation results demonstrated that PHD1 also had UDP-Glc epimerase activity in vivo (FIG. 12B).

RNA gel blot analysis revealed that PHD1 was present in all green tissues, with highest abundance in leaf blades and sheaths, then flowers and culms, but only at very low levels in roots (FIG. 4A). mRNA in situ hybridization revealed that PHD1 was expressed predominantly in leaf primodia and shoot apical meristems (FIG. 4B), the mesophyll cells surrounding the vascular bundles of young leaves (FIG. 4C), inflorescence primodia (FIG. 4D), and axillary buds (FIG. 4E). PHD1 encodes a 340 aa protein with a putative 62-aa chloroplast transit peptide at the N-terminus. To confirm chloroplast localization of PHD1, the full-length PHD1 was fused to the green fluorescent protein (GFP) reporter gene under the control of the cauliflower mosaic virus (CaMV) 35S promoter and subsequently transformed into rice shoot protoplasts. FIG. 4F shows that GFP fluorescence co-localized with the red chlorophyll autofluorescence, confirming that PHD1 was a chloroplast-localized protein and that the predicted transit peptide was functional.

Example 3

PHD1 Influences the Homeostasis of Nucleotide Sugars and Carbon Assimilation in Leaves UDP-Gal is the activated form of galactose in biosynthetic reactions, but a galactose salvage pathway exists in eukaryotic organisms. To assess expression of genes involved in the Leloir salvage pathway, the expression levels of three key genes of this pathway, GalM, GalK, and GalT, were analyzed in both phd1-1 and wild type. The expression of all three genes was significantly upregulated in the phd1-1 mutant, suggesting an activation of the whole salvage pathway (FIG. 5A). β-Lactase is involved in the generation of free β-D-Gal from polysaccharide breakdown, and UDP-Glc pyrophosphorylase (UGP) catalyzes the formation of UDP-Glc from Glc-1-P. The expression levels of genes encoding β-lactase and UGP3 were also upregulated in phd1-1. Surprisingly, the expression levels of OsUGE1 and OsUGE4 encoding for putative cytoplasmic isoforms of UGE in rice were more than two-fold higher in phd1-1 than in wild type plants, indicating an upregulation of de novo UDP-Gal biosynthesis in the cytoplasm. These results suggested that PHD1 is likely responsible for a majority of the UGE function in chloroplasts, and appears to be involved in the generation of UDP-Gal from UDP-Glc to supply building blocks for galactolipid biosynthesis required for proper chloroplast membrane composition.

To determine whether impairment of UGE activity in phd1-1 had an effect on galactose-containing compounds, the intermediates of galactose metabolism were analyzed. The amount of UDP-Gal was found to be slightly higher in leaves of phd1-1 than in wild type, but the UDP-Glc amount was significantly higher (FIG. 6A). Hence, the ratio of UDP-Glc to UDP-Gal in phd1-1 was also higher than in wild type leaves. These results suggested that PHD1 dysfunction may trigger the accumulation of substrates and disturb the balance of interconversion between the two sugar nucleotides.

Because the phd1-1 mutant exhibited a significant decrease of carbon assimilate levels, it was determined whether transcript levels of several key genes involved in the synthesis, transport, and cleavage of starch and sucrose were altered in mature leaves of wild type and phd1-1 plants. Interestingly, while the expression of genes in starch biosynthesis such as AGPL2, SSI, SSIIIa, GBSS, BE, and BT1, was suppressed in the phd1-1 mutant (FIG. 5B), expression levels of genes participating in sucrose cleavage, such as INV1/3 and SuSy1, were all increased (FIG. 5C). Meanwhile, the GPT gene encoding a glucose-6-phosphate/phosphate translocator was upregulated in phd1-1, indicating an enhanced export of hexose-phosphates from chloroplasts to the cytosol. In addition, increased expression level of UGP2, a gene involved in UDP-Glc synthesis, was correlated with increased UDP-Glc accumulation and a higher UDP-Glc/UDP-Gal ration in the phd1-1 mutant.

Example 4

PHD1 Dysfunction Affects the Photosynthetic Membrane System

Chloroplast membranes contain high levels of glycolipids, and UDP-Gal is a dominant substrate for glycolipid biosynthesis. To examine the effect of PHD1 dysfunction on membrane lipid homeostasis, the composition of total lipids extracted from phd1-1, wild type, and PHD1-complemented plants was analyzed (FIG. 6B). In the phd1-1 mutant, the mol % amount of MGDG was reduced by 19% compared to wild type and the complemented plants, indicating that PHD1 is involved in MGDG biosynthesis. In contrast, only a slight decrease (2.5%) in DGDG content was observed in the phd1-1 mutant, demonstrating that PHD1 may not be required for DGDG synthesis and suggesting that the UDP-Gal substrate for DGDG formation was presumably supplied from the cytosol. Reduced abundance of MGDG in phd1-1 was accompanied by an increased abundance of other major membrane lipids such as phosphatidylcholine (PC), phosphoinositol (PI), and phosphatidylglycerol (PG), while the mol % levels of sulfoquinovosyldiacylglycerol (SQDG) and phosphatidyl ethanolamine (PE) were only slightly but not significantly higher in the phd1-1 mutant (FIG. 6B). Because PC, PI, and PG are also components of thylakoid membranes, these results demonstrated that the mutant thylakoid membranes had an increased mol % amount of phospholipids.

Noninvasive chlorophyll fluorescence measurements indicated that the maximum quantum yields for photosystem II photochemistry ($F_v/F_m$) were similar for phd1-1 and wild type (Table 1). The effective quantum yield of photochemical energy conversion in photosystem II ($\phi_{PSII}$) was slightly but significantly reduced in the mutant (Table 1). Pigment content was also reduced in the phd1-1 mutant (Table 1). Interestingly, in 2-month-old plants chloroplasts were significantly smaller in phd1-1 mutant than wild type plants (wild type, 5.0±0.4 μm; phd1-1, 3.0±0.5 μm), and starch grains were also either absent or reduced in size and/or number in the mutant. These data indicated that a reduced amount of galactolipids in chloroplasts might reduce photosynthetic capability of higher plants.

TABLE 1

Pigment content (mg·g$^{-1}$ fresh weight) and photosynthetic parameters of wild type, phd1-1, and the PHD1-complemented plants.

|  | Wild type | phd1-1 | phd1-1 + PHD1 |
|---|---|---|---|
| Chlorophyll a | 2.50 ± 0.34 | 1.86 ± 0.36* | 2.48 ± 0.37 |
| Chlorophyll b | 0.96 ± 0.13 | 0.67 ± 0.12* | 0.93 ± 0.18 |
| Chlorophyll a + b | 3.46 ± 0.42 | 2.53 ± 0.43* | 3.41 ± 0.52 |
| Chlorophyll a/b | 2.62 ± 0.37 | 2.77 ± 0.41 | 2.66 ± 0.55 |
| Carotenoids | 0.33 ± 0.04 | 0.28 ± 0.05 | 0.34 ± 0.07 |
| $F_v/F_m$ | 0.84 ± 0.01 | 0.79 ± 0.01 | 0.83 ± 0.02 |
| $\phi_{PSII}$ | 0.72 ± 0.01 | 0.58 ± 0.02* | 0.70 ± 0.02 |

Samples were collected from fully-expanded leaves of 4-month-old plants grown in paddy fields.
Values represent means (±SD) of six to ten independent determinations.
*Significant difference between mutant and wild type (P < 0.05).

Example 5

Expression of PHD1 Increases Growth Rate and Grain Yield

It was investigated whether biomass and grain yield could be improved by PHD1 overexpression. Transgenic rice plants overexpressing PHD1 showed a significant increase in tillering (branching) and photosynthetic rate when grown in paddy fields (FIG. 7A, Table 2). The growth rate of transgenic plants accelerated at the seedling stage and dry material accumulation was enhanced 12.5% to 22.4% at the mature stage compared to non-transgenic plants (FIG. 7D, Table 2). In addition, compared to non-transgenic control plants, grain yield per plant of transgenic lines S3, S5, and S8 increased 10.7, 15.5, and 18.3%, respectively (FIG. 7C). These results demonstrated that PHD1 overexpression in rice is positively correlated with an increase in biomass production and grain yield.

TABLE 2

Characterization of biomass and photosynthetic rate of PHD1-overexpressing plants and wild type (Nipponbare).

|  | WT | S3 | S5 | S8 |
|---|---|---|---|---|
| Shoot height (cm)[a] | 15.32 ± 0.15 | 18.64 ± 0.18* | 19.21 ± 0.33* | 19.64 ± 0.37* |
| Shoot mass (mg)[a] | 54.73 ± 1.02 | 63.45 ± 1.13* | 66.55 ± 1.17* | 65.91 ± 1.20* |
| NPR (500 μmol · m$^{-2}$ · s$^{-1}$)[b] | 8.31 ± 0.24 | 9.65 ± 0.53* | 10.12 ± 0.37* | 10.39 ± 0.59* |
| NPR (2000 μmol · m$^{-2}$ · s$^{-1}$)[b] | 14.50 ± 0.99 | 15.78 ± 0.86 | 16.12 ± 1.28 | 16.36 ± 1.36 |

S3, S5, and S8 represent three independent PHD1-overexpressing transgenic lines.
[a] 20-day-old rice seedlings;
[b] NPR, rate of net photosynthesis (μmol · $CO_2$ · m$^{-2}$ · s$^{-1}$) measured at the heading stage;
Values are means ± SD from at least 30 plants/line,
*Significant difference (P < 0.05).

TABLE 3

Oligonucleotides (SEQ ID NOS: 35-52, consecutive) used for galactose metabolism analysis.

| Name | Sequence (5'-3') |
|---|---|
| β-lactase2 | GTCGTGCCATGACATCTACCA<br>CTGCTTTATTGCCTCACTTGC |
| GalM4 | CGTCGTGCTTCCTGACTCCA<br>CCTCCACCAACATGCTCCTTC |
| GalK2 | ACATAACCTACCGAAGAAGAGTGG<br>TCACAGCCTGAAGCACATAAAA |
| GalT | GGATACGGCACTGGATCTTGG<br>TTGAATGGAGGGTCGTTGAGC |
| OsUGE1 | TACTGCTCCGATACTTCAACCC<br>CCATCCGCTAGATCAACAACAT |
| OsUGE2 | CCAAGACGCCCTGGTGATGC<br>TTCGCTTTCCAGTTGAGTTCCTTC |
| OsUGE3 | TCGCTACTCCTGACATTGGTT<br>TGATCGCCCTAATTCTGCTC |
| OsUGE4 | TGGAACAGGAAAGGGAACATC<br>TCGTGGACCAATAACCAAAGG |
| UGP3 | GCCAGAACAAACCCATCAAAC<br>GTAACTCCAGAGCCGAACCAG |

TABLE 4

Oligonucleotides (SEQ ID NOS: 53-76, consecutive) used for carbohydrate metabolism analysis.

| Name | Sequence (5'-3') |
|---|---|
| AGPL2 | ATAATCTCCGATGGCTGTTC<br>TCCAGACCTTATGTAGTATCCC |
| SSI | GGGCCTTCATGGATCAACC<br>CCGCTTCAAGCATCCTCATC |
| SSIIIa | GCCTGCCCTGGACTACATTG<br>GCAAACATATGTACACGGTTCTGG |
| GBSSI | AACGTGGCTGCTCCTTGAA<br>TTGGCAATAAGCCACACACA |
| BEI | TGGCCATGGAAGAGTTGGC<br>CAGAAGCAACTGCTCCACC |

TABLE 4-continued

Oligonucleotides (SEQ ID NOS: 53-76, consecutive) used for carbohydrate metabolism analysis.

| Name | Sequence (5'-3') |
| --- | --- |
| BTI-1 | GAAGTCCTTGAGCCGTCCTG |
|  | AAGTCCCTTGATGCCCTCCT |
| GPT1 | AGAAGGGATCCAGATGAAGAA |
|  | AACAAGAAACGAGCAACATAGA |
| GPT2 | GCCTCCATCATCATCTTCCA |
|  | ATTGTTACATCCCGAGCACC |
| UGP2 | GCCAGAACAAACCCATCAAAC |
|  | GTAACTCCAGAGCCGAACCAG |
| SuSy1 | GCTTCCACATTGACCCATAC |
|  | CTTGAGGGCATACAGCATCT |
| INV1 | CACGACGCAGTGATCTGAGG |
|  | GATGAAACGCAGGGAATACG |
| INV3 | GACATCGTCAAGAGGGTCG |
|  | CCATCCATGATCCATCATCC |

Example 9

Electroporation of *Agrobacterium tumefaciens* LBA4404

Electroporation competent cells (40 µL), such as *Agrobacterium tumefaciens* LBA4404 containing PHP10523 ("pSB1"; Komari et al., *Plant J.* 10:165-174 (1996); NCBI General Identifier No. 59797027), are thawed on ice (20-30 min). PHP10523 contains VIR genes for T-DNA transfer, an *Agrobacterium* low copy number plasmid origin of replication, a tetracycline resistance gene, and a Cos site for in vivo DNA bimolecular recombination. Meanwhile the electroporation cuvette is chilled on ice. The electroporator settings are adjusted to 2.1 kV. A DNA aliquot (0.5 µL parental DNA at a concentration of 0.2 µg-1.0 µg in low salt buffer or twice distilled $H_2O$) is mixed with the thawed *Agrobacterium tumefaciens* LBA4404 cells while still on ice. The mixture is transferred to the bottom of electroporation cuvette and kept at rest on ice for 1-2 min. The cells are electroporated (Eppendorf electroporator 2510) by pushing the "pulse" button twice (ideally achieving a 4.0 millisecond pulse). Subsequently, 0.5 mL of room temperature 2×YT medium (or SOC medium) are added to the cuvette and transferred to a 15 mL snap-cap tube (e.g., FALCON™ tube). The cells are incubated at 28-30° C., 200-250 rpm for 3 h.

Aliquots of 250 µL are spread onto plates containing YM medium and 50 µg/mL spectinomycin and incubated three days at 28-30° C. To increase the number of transformants one of two optional steps can be performed:

Option 1: Overlay plates with 30 µL of 15 mg/mL rifampicin. LBA4404 has a chromosomal resistance gene for rifampicin. This additional selection eliminates some contaminating colonies observed when using poorer preparations of LBA4404 competent cells.

Option 2: Perform two replicates of the electroporation to compensate for poorer electrocompetent cells.

Identification of Transformants:

Four independent colonies are picked and streaked on plates containing AB minimal medium and 50 µg/mL spectinomycin for isolation of single colonies. The plates are incubated at 28° C. for two to three days. A single colony for each putative co-integrate is picked and inoculated with 4 mL of 10 g/L bactopeptone, 10 g/L yeast extract, 5 g/L sodium chloride and 50 mg/L spectinomycin. The mixture is incubated for 24 h at 28° C. with shaking. Plasmid DNA from 4 mL of culture is isolated using QIAGEN® Miniprep and an optional Buffer PB wash. The DNA is eluted in 30 µL. Aliquots of 2 µL are used to electroporate 20 µL of DH10b+20 µL of twice distilled $H_2O$ as per above. Optionally a 15 µL aliquot can be used to transform 75-100 µL of INVITROGEN™ Library Efficiency DH5α. The cells are spread on plates containing LB medium and 50 µg/mL spectinomycin and incubated at 37° C. overnight.

Three to four independent colonies are picked for each putative co-integrate and inoculated 4 mL of 2×YT medium (10 g/L bactopeptone, 10 g/L yeast extract, 5 g/L sodium chloride) with 50 µg/mL spectinomycin. The cells are incubated at 37° C. overnight with shaking. Next, isolate the plasmid DNA from 4 mL of culture using QIAPREP® Miniprep with optional Buffer PB wash (elute in 50 µL). Use 8 µL for digestion with SalI (using parental DNA and PHP10523 as controls). Three more digestions using restriction enzymes BamHI, EcoRI, and HindIII are performed for 4 plasmids that represent 2 putative co-integrates with correct SalI digestion pattern (using parental DNA and PHP10523 as controls). Electronic gels are recommended for comparison.

Example 11

Transformation of Maize Using *Agrobacterium*

*Agrobacterium*-mediated transformation of maize is performed essentially as described by Zhao et al. in *Meth. Mol. Biol.* 318:315-323 (2006) (see also Zhao et al., *Mol. Breed.* 8:323-333 (2001) and U.S. Pat. No. 5,981,840 issued Nov. 9, 1999, incorporated herein by reference). The transformation process involves bacterium inoculation, co-cultivation, resting, selection and plant regeneration.

1. Immature Embryo Preparation:

Immature maize embryos are dissected from caryopses and placed in a 2 mL microtube containing 2 mL PHI-A medium.

2. *Agrobacterium* Infection and Co-Cultivation of Immature Embryos:

2.1 Infection Step:

PHI-A medium of (1) is removed with 1 mL micropipettor, and 1 mL of *Agrobacterium* suspension is added. The tube is gently inverted to mix. The mixture is incubated for 5 min at room temperature.

2.2 Co-culture Step:

The *Agrobacterium* suspension is removed from the infection step with a 1 mL micropipettor. Using a sterile spatula the embryos are scraped from the tube and transferred to a plate of PHI-B medium in a 100×15 mm Petri dish. The embryos are oriented with the embryonic axis down on the surface of the medium. Plates with the embryos are cultured at 20° C., in darkness, for three days. L-Cysteine can be used in the co-cultivation phase. With the standard binary vector, the co-cultivation medium supplied with 100-400 mg/L L-cysteine is critical for recovering stable transgenic events.

3. Selection of Putative Transgenic Events:

To each plate of PHI-D medium in a 100×15 mm Petri dish, 10 embryos are transferred, maintaining orientation and the dishes are sealed with PARAFILM®. The plates are incubated in darkness at 28° C. Actively growing putative events, as pale yellow embryonic tissue, are expected to be visible in six to eight weeks. Embryos that produce no events may be brown and necrotic, and little friable tissue growth is evident. Putative transgenic embryonic tissue is subcultured to fresh PHI-D plates at two-three week intervals, depending on growth rate. The events are recorded.

4. Regeneration of T0 Plants:

Embryonic tissue propagated on PHI-D medium is subcultured to PHI-E medium (somatic embryo maturation medium), in 100×25 mm Petri dishes and incubated at 28° C., in darkness, until somatic embryos mature, for about ten to eighteen days. Individual, matured somatic embryos with well-defined scutellum and coleoptile are transferred to PHI-F embryo germination medium and incubated at 28° C. in the light (about 80 µE from cool white or equivalent fluorescent lamps). In seven to ten days, regenerated plants, about 10 cm tall, are potted in horticultural mix and hardened-off using standard horticultural methods.

Media for Plant Transformation:
1. PHI-A: 4 g/L CHU basal salts, 1.0 mL/L 1000× Eriksson's vitamin mix, 0.5 mg/L thiamin HCl, 1.5 mg/L 2,4-D, 0.69 g/L L-proline, 68.5 g/L sucrose, 36 g/L glucose, pH 5.2. Add 100 µM acetosyringone (filter-sterilized).
2. PHI-B: PHI-A without glucose, increase 2,4-D to 2 mg/L, reduce sucrose to 30 g/L and supplemented with 0.85 mg/L silver nitrate (filter-sterilized), 3.0 g/L GELRITE®, 100 µM acetosyringone (filter-sterilized), pH 5.8.
3. PHI-C: PHI-B without GELRITE® and acetosyringonee, reduce 2,4-D to 1.5 mg/L and supplemented with 8.0 g/L agar, 0.5 g/L 2-[N-morpholino]ethanesulfonic acid (MES) buffer, 100 mg/L carbenicillin (filter-sterilized).
4. PHI-D: PHI-C supplemented with 3 mg/L bialaphos (filter-sterilized).
5. PHI-E: 4.3 g/L of Murashige and Skoog (MS) salts, (Gibco, BRL 11117-074), 0.5 mg/L nicotinic acid, 0.1 mg/L thiamine HCl, 0.5 mg/L pyridoxine HCl, 2.0 mg/L glycine, 0.1 g/L myo-inositol, 0.5 mg/L zeatin (Sigma, Cat. No. Z-0164), 1 mg/L indole acetic acid (IAA), 26.4 µg/L abscisic acid (ABA), 60 g/L sucrose, 3 mg/L bialaphos (filter-sterilized), 100 mg/L carbenicillin (filter-sterilized), 8 g/L agar, pH 5.6.
6. PHI-F: PHI-E without zeatin, IAA, ABA; reduce sucrose to 40 g/L; replacing agar with 1.5 g/L GELRITE®; pH 5.6.

Plants can be regenerated from the transgenic callus by first transferring clusters of tissue to N6 medium supplemented with 0.2 mg per liter of 2,4-D. After two weeks the tissue can be transferred to regeneration medium (Fromm et al., Bio/Technology 8:833-839 (1990)).

Transgenic T0 plants can be regenerated and their phenotype determined. T1 seed can be collected. T1 plants, and/or their progeny, can be grown and their phenotype determined.

Example 15

Yield Analysis of Maize Lines Transformed with PHD1 Gene

A recombinant DNA construct containing PHD1 gene can be introduced into an elite maize inbred line either by direct transformation or introgression from a separately transformed line.

Transgenic plants, either inbred or hybrid, can undergo more vigorous field-based experiments to study yield enhancement and/or stability under well-watered and water-limiting conditions.

Subsequent yield analysis can be done to determine whether plants that contain the validated drought tolerant lead gene have an improvement in yield performance under water-limiting conditions, when compared to the control plants that do not contain the validated drought tolerant lead gene. Specifically, drought conditions can be imposed during the flowering and/or grain fill period for plants that contain the validated drought tolerant lead gene and the control plants. Reduction in yield can be measured for both. Plants containing the validated drought tolerant lead gene have less yield loss relative to the control plants, for example, at least 25% less yield loss, under water limiting conditions, or would have increased yield relative to the control plants under water non-limiting conditions.

The above method may be used to select transgenic plants with increased yield, under water-limiting conditions and/or well-watered conditions, when compared to a control plant not comprising said recombinant DNA construct.

The invention claimed is:

1. A method of increasing the production of UDP-galactose in situ in the chloroplast for mono-galactosyldiacylglycerol (MGDG) biosynthesis in a plant, the method comprising expressing from a DNA construct comprising a nucleic acid encoding a chloroplast UDP-glucose epimerase under the control of at least one regulatory promoter element in the plant, wherein the chloroplast UDP-glucose epimerase comprises a chloroplast transit peptide, and wherein the UDP-glucose epimerase is a monocot polypeptide comprising an amino acid sequence that is at least 95% identical to SEQ ID NO: 1.

2. The method of claim 1, wherein the plant is selected from the group consisting of maize, rice, sugarcane, and wheat.

3. The method of claim 1, wherein the carbon partitioning in the plant is altered.

4. The method of claim 1, wherein the photosynthetic efficiency of the plant is increased.

5. The method of claim 1, wherein the drought tolerance of the plant is increased.

6. A method of increasing yield of a plant, the method comprising expressing a recombinant chloroplast UDP-glucose epimerase operably linked to at least one regulatory element, wherein the chloroplast UDP-glucose epimerase is localized in the chloroplast, and wherein the UDP-glucose epimerase is a monocot polypeptide comprising an amino acid sequence that is at least 95% identical to SEQ ID NO: 1.

7. The method of claim 6, wherein the plant is selected from the group consisting of maize, rice, sugarcane, and wheat.

8. The method of claim 6, wherein the carbon partitioning in the plant is altered.

9. The method of claim 6, wherein the photosynthetic efficiency of the plant is increased.

10. The method of claim 6, wherein the drought tolerance of the plant is increased.

11. The method of claim 1, wherein the UDP-glucose epimerase is a monocot polypeptide comprising an amino acid sequence that is at least 98% identical to SEQ ID NO: 1.

12. The method of claim 6, wherein the UDP-glucose epimerase is a monocot polypeptide comprising an amino acid sequence that is at least 98% identical to SEQ ID NO: 1.

* * * * *